(12) United States Patent
Ebisawa

(10) Patent No.: US 9,514,538 B2
(45) Date of Patent: Dec. 6, 2016

(54) PUPIL DETECTION METHOD, CORNEAL REFLEX DETECTION METHOD, FACIAL POSTURE DETECTION METHOD, AND PUPIL TRACKING METHOD

(71) Applicant: National University Corporation Shizuoka University, Shizuoka-shi, Shizuoka (JP)

(72) Inventor: Yoshinobu Ebisawa, Hamamatsu (JP)

(73) Assignee: NATIONAL UNIVERSITY CORPORATION SHIZUOKA UNIVERSITY (JP)

( * ) Notice: Subject to any disclaimer, the term of this patent is extended or adjusted under 35 U.S.C. 154(b) by 179 days.

(21) Appl. No.: 14/402,952

(22) PCT Filed: May 24, 2013

(86) PCT No.: PCT/JP2013/064511
§ 371 (c)(1),
(2) Date: Apr. 2, 2015

(87) PCT Pub. No.: WO2013/176265
PCT Pub. Date: Nov. 28, 2013

(65) Prior Publication Data
US 2015/0287206 A1    Oct. 8, 2015

(30) Foreign Application Priority Data
May 25, 2012   (JP) ............................... P2012-120312

(51) Int. Cl.
G06K 9/00       (2006.01)
G06T 7/00       (2006.01)
(Continued)

(52) U.S. Cl.
CPC .............. G06T 7/0075 (2013.01); A61B 3/111 (2013.01); A61B 3/113 (2013.01); G06F 3/0346 (2013.01);
(Continued)

(58) Field of Classification Search
USPC ....................................................... 382/117
See application file for complete search history.

(56) References Cited

U.S. PATENT DOCUMENTS

| | | | | |
|---|---|---|---|---|
| 5,859,921 A * | 1/1999 | Suzuki | ............... | G06K 9/00268 382/118 |
| 2005/0031173 A1* | 2/2005 | Hwang | .............. | G06K 9/00597 382/118 |

(Continued)

FOREIGN PATENT DOCUMENTS

| | | |
|---|---|---|
| JP | 2007-058507 | 3/2007 |
| JP | 2009-267729 | 11/2009 |

(Continued)

OTHER PUBLICATIONS

PCT/IB/338 Notification of Transmittal of Translation of the International Preliminary Report on Patentability in counterpart International Application No. PCT/JP2013/064511 in English dated Dec. 4, 2014 (6 pages).

(Continued)

*Primary Examiner* — John Strege
(74) *Attorney, Agent, or Firm* — Ostrolenk Faber LLP

(57) ABSTRACT

A pupil detection method includes a step of acquiring images by taking a facial image of a subject using each of a left camera and a right camera, a step of extracting one or more image candidate points serving as candidates for pupils from the images, a step of extracting points corresponding to a combination of image candidate points corresponding to the same point in a three-dimensional space as space candidate points, a step of selecting a pair of two space candidate points from the extracted space candidate points and calculating a distance between the selected pair, a step of excluding a pair of space candidate points where the calculated distance is not within a specified range, and a step of determining one or more pairs of space candidate points from the pairs not excluded and determining that a pair of pupils of the subject exist at the positions.

13 Claims, 28 Drawing Sheets

(51) Int. Cl.
*A61B 3/11* (2006.01)
*A61B 3/113* (2006.01)
*G06F 3/0346* (2013.01)
*A61B 3/15* (2006.01)

(52) U.S. Cl.
CPC ....... *G06K 9/00281* (2013.01); *G06K 9/00604* (2013.01); *G06K 9/00617* (2013.01); *G06T 7/0042* (2013.01); *G06T 7/0044* (2013.01); *A61B 3/158* (2013.01); *G06T 2207/10012* (2013.01); *G06T 2207/30041* (2013.01); *G06T 2207/30201* (2013.01)

(56) References Cited

U.S. PATENT DOCUMENTS

| | | | | |
|---|---|---|---|---|
| 2005/0175218 | A1* | 8/2005 | Vertegaal | A61B 3/113 382/103 |
| 2005/0180611 | A1* | 8/2005 | Oohashi | G06K 9/00234 382/118 |
| 2006/0147094 | A1* | 7/2006 | Yoo | G06K 9/00604 382/117 |
| 2007/0201729 | A1* | 8/2007 | Yuasa | G06K 9/00281 382/118 |
| 2008/0069410 | A1* | 3/2008 | Ko | G06K 9/0061 382/117 |
| 2009/0304232 | A1* | 12/2009 | Tsukizawa | A61B 3/113 382/103 |
| 2014/0055342 | A1* | 2/2014 | Kamimura | G06F 3/013 345/156 |
| 2016/0026847 | A1* | 1/2016 | Vugdelija | G06K 9/6218 382/103 |

FOREIGN PATENT DOCUMENTS

| | | |
|---|---|---|
| JP | 2010-067104 | 3/2010 |
| JP | 4431749 | 3/2010 |
| JP | 4452832 | 4/2010 |
| JP | 4452836 | 4/2010 |
| JP | 4517049 | 8/2010 |
| JP | 4568836 | 10/2010 |
| JP | 4765008 | 9/2011 |
| JP | 4839432 | 12/2011 |
| JP | 4899059 | 3/2012 |
| WO | WO 2010/010926 A1 | 1/2010 |
| WO | WO 2012/020760 A1 | 2/2012 |

OTHER PUBLICATIONS

Extended European Search Report dated Aug. 18, 2016 for corresponding EP Patent Application 13793886.6.

Ebisawa Y. "Realtime 3D position detection of human pupil", Virtual Environment, Jul. 12, 2004, p. 8-12, XP010773354.

Fiora Pirri et al. "A general method for the point of regard estimation in 3D space", Computer Vision and Pattern Recognition, Jun. 20, 2011, p. 921-928, XP032038136.

Stefan Kohlbecher et al., "Calibration-free eye tracking by reconstruction of the pupil ellipse in 3D space ", ETRA '08 Proceedings of the Symposium on eye Tracking Research & Applications, Jan. 1, 2008, p. 135-138, XP055182771.

Ebisawa Y. et al., "Face Dose estimation based on 3D detection of pupils and nostrils", Virtual Environments, Jul. 18, 2005, p. 92-97, XP010873748.

\* cited by examiner (a)　　　　　　　　　　(b)

*Fig.28*
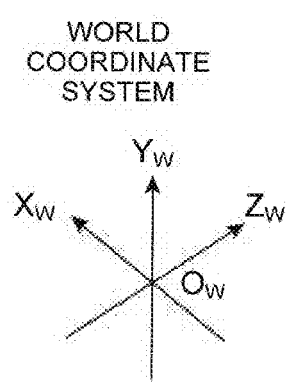
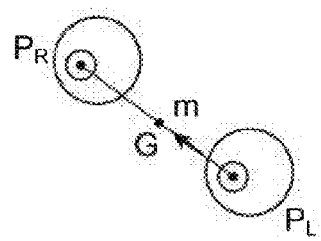
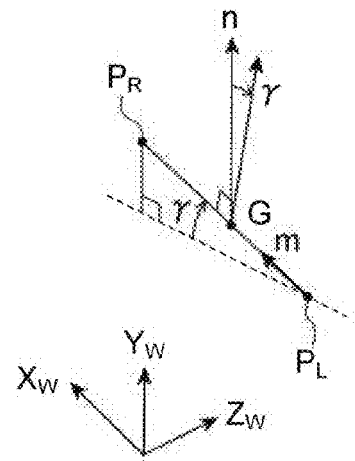
(a)　　　　　　　　　　　　　(b)
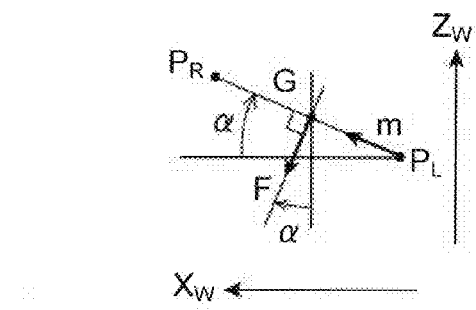
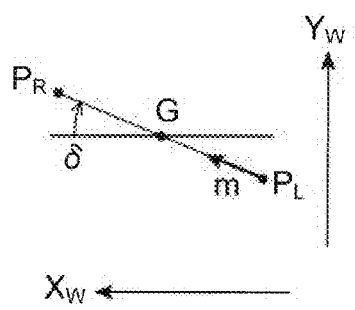
(c)　　　　　　　　　　　　　(d)

PUPIL DETECTION METHOD, CORNEAL REFLEX DETECTION METHOD, FACIAL POSTURE DETECTION METHOD, AND PUPIL TRACKING METHOD

CROSS-REFERENCE TO RELATED APPLICATIONS

The present application is a 35 U.S.C. §§371 national phase conversion of PCT/JP2013/064511, filed May 24, 2013, which claims priority to Japanese Patent Application No. 2012-120312, filed May 25, 2012, the contents of both of which are incorporated herein by reference. The PCT International Application was published in the Japanese language.

TECHNICAL FIELD

The present invention relates to a pupil detection method, a corneal reflection detection method and a facial posture detection method for detecting the pupils, corneal reflection and facial posture of a subject by images taken, and a pupil tracking method for tracking the pupils of a subject.

BACKGROUND ART

A technique for detecting the pupils of a subject can be used for detection of line of sight for medical testing or man-machine interface (see Patent Literature 1 below), drowsiness detection for a subject driving a vehicle (see Patent Literature 2 below), face orientation detection (see Patent Literature 3, 4 below), a pupil mouse for input to a computer or a game machine by the motion of the pupils of a subject without using a finger (see Patent Literature 5 below) and the like, for example. The present inventor has developed a technique to detect the pupils from images taken by a camera.

In the techniques disclosed in Patent Literatures 1 to 5, a method that distinguishes a pupil part from the surrounding image by subtraction between a light pupil image and a dark pupil image taken by a camera is used for detection of pupils. When placing a light source such as a near-infrared light source near the aperture of a camera and emitting light to the face of a subject along the light axis of the camera and taking an image, the light reaches the retina through the pupil and is reflected, then passes through the crystalline lens and the cornea and returns to the aperture of the camera. The pupil appears light in the image, and this image is referred to as a light pupil image. On the other hand, when emitting light from a light source away from the aperture of a camera to the face of a subject and taking an image, the light reflected from the retina does not substantially enter the aperture of the camera, and therefore the pupil appears dark in the image, and this image is referred to as a dark pupil image. The size of the pupil changes depending on the lightness of the surrounding, and it becomes small in a light place, which makes it difficult to be detected. Further, when the subject wears glasses, reflections occur in a part of the glasses near the pupil, and the glasses reflection appears in the image, and therefore it is difficult to detect the pupil from a single image even with use of any of the light pupil image and the dark pupil image. However, if subtraction of the dark pupil image from the light pupil image is performed, because the surrounding part other than the pupil part has almost the same lightness between both images, they cancel out each other, and only the pupil part having a difference in lightness is clearly shown. It is thereby possible to easily detect the pupil.

However, when using a common camera, there is a difference between the time to acquire a light pupil image and the time to acquire a dark pupil image. Therefore, when a face moves quickly during acquisition of the two images, a displacement occurs between the positions of the light pupil image and the dark pupil image, and the effect of image subtraction cannot be sufficiently obtained. Particularly, such a phenomenon is significant when a subject wears glasses, and glasses reflection, which is an image of light that is reflected on the lens or frame of the glasses, is likely to remain after the subtraction of the images, and the remaining glasses reflection image and the pupils cannot be easily distinguishable in some cases.

Thus, in order to prevent misdetection of a pupil caused by the above-described glasses reflection, a technique is introduced that, after detecting a pupil, applies an analysis window to a small region including the detected pupil in the image taken after that, and then tracks the pupil by searching for the pupil only in the small region, thereby reducing the pupil misdetection rate (for example, see Patent Literature 6).

Further, as a measure against the problem that the position of the pupil is displaced due to a difference in acquisition time of a light pupil image and a dark pupil image and it becomes difficult to detect position of the pupil, a subtraction position correction method using the amount of movement of nostrils (for example, see Patent Literature 7) and a subtraction position correction method using the amount of movement of corneal reflection (for example, see Patent Literature 8) are proposed, and their effectiveness is shown.

Furthermore, in the subtraction position correction method using the amount of movement of nostrils, when the head of a subject rotates around the axis penetrating the subject's head front to rear, the amount of movement of nostrils and the amount of movement of the pupils are not always the same, and the pupil detection accuracy is not high enough in some cases. In view of this, the present inventor has proposed a subtraction position correction method using a facial posture (for example, see Patent Literature 9).

CITATION LIST

Patent Literature

PTL1: Japanese Patent No. 4517049
PTL2: Japanese Patent No. 4899059
PTL3: Japanese Patent No. 4431749
PTL4: Japanese Patent No. 4765008
PTL5: Japanese Patent No. 4839432
PTL6: Japanese Patent No. 4568836
PTL7: Japanese Patent No. 4452832
PTL8: Japanese Patent No. 4452836
PTL9: International Publication No. 2010/010926

SUMMARY OF INVENTION

Technical Problem

However, the above-described techniques are based on the assumption that the nostrils of a subject appear in the camera image. Human nostrils generally point downwards on the human face. Accordingly, it is preferable to place the camera below the face of a subject. Further, placing the camera below the face is preferable also to prevent glasses reflection from entering the image.

On the other hand, in the case of detecting the line of sight or the point of regard based on the relative position between pupil and corneal reflection, the detection range of the line of sight or the point of regard is limited to about 0 to 30 degrees around the camera. Accordingly, when detecting the point of regard or the like over a wide range in front of a subject, it is not possible to place the camera significantly down below the subject's face. Therefore, in the case of detecting the line of sight or the point of regard, it is difficult to detect nostrils and glasses reflection is likely to appear because the camera cannot be placed down below.

Further, in the field of application such as a pupil mouse where a user rotates the head widely, the situation where nostrils cannot be detected or the situation where glasses lens reflection overlaps pupils are likely to occur depending on the direction of the user's head.

Furthermore, when pupils disappear from an image while a subject is blinking, if a glasses reflection image exists in the image, the glasses reflection image is misdetected as pupils in some cases. Once the misdetection is done, the misdetected glasses reflection image is tracked after that, and it is not possible to correctly detect pupils.

The present invention has been accomplished to solve the above problems and an object of the present invention is thus to provide a pupil detection method and tracking method that can improve robustness and accuracy without imposing restrictions on the rotation of a user's head and the positions of cameras.

Solution to Problem

To solve the above problems, a pupil detection method according to one aspect of the present invention includes a first step of acquiring a first image by taking a facial image of a subject using a first camera, a second step of acquiring a second image by taking a facial image of the subject using a second camera, a third step of extracting one or more first image candidate points serving as candidates for a pupil of the subject from the first image, a fourth step of extracting one or more second image candidate points serving as candidates for a pupil of the subject from the second image, a fifth step of determining whether a combination of one of the first image candidate points and one of the second image candidate points corresponds to the same point in a three-dimensional space, a sixth step of extracting two or more space candidate points by setting the point in the three-dimensional space corresponding to the combination of the first image candidate point and the second image candidate point determined as corresponding to the same point in three-dimensional coordinates as the space candidate point, a seventh step of selecting a pair of two space candidate points among the extracted space candidate points and calculating a distance between the selected pair of two space candidate points for a plurality of pairs of space candidate points, an eighth step of excluding a pair of space candidate points where the calculated distance between the pair of space candidate points is not within a specified range, and a ninth step of determining one or more pairs of space candidate points among the pairs of space candidate points having not been excluded and determining that a pair of pupils of the subject exist at positions of the determined one or more pair of space candidate points.

In the pupil detection method according to one aspect of the present invention, a first image and a second image are acquired respectively by a first camera and a second camera, and first image candidate points are extracted from the first image, and second image candidate points are extracted from the second image. Then, for a combination of the first image candidate point and the second image candidate point, it is determined whether the combination corresponds to the same point in a three-dimensional space, and the point in the three-dimensional space corresponding to the combination of the first image candidate point and the second image candidate point that is determined to correspond to the same point is set as the space candidate point. Further, a pair of two space candidate points are selected among the extracted space candidate points, and a distance between the selected pair is calculated, and a pair where the calculated distance is not within a specified range is excluded, and one or more pairs of space candidate points are selected among the pairs having not been excluded. Thus, because pupils can be detected if the pupils appear in the images acquired by the two cameras, it is thereby possible to improve robustness and accuracy without imposing restrictions on the rotation of a user's head and the positions of cameras.

A corneal reflection detection method according to one aspect of the present invention includes a nineteenth step of detecting pupils of a subject by the above-described pupil detection method, a twentieth step of extracting one or more first image corneal reflection candidate points serving as candidates for corneal reflection of the subject from the first image, a twenty-first step of extracting one or more second image corneal reflection candidate points serving as candidates for corneal reflection of the subject from the second image, a twenty-second step of selecting one from each of the extracted first image corneal reflection candidate points and second image corneal reflection candidate points, a twenty-third step of calculating three-dimensional coordinates corresponding to a combination of the selected first image corneal reflection candidate point and second image corneal reflection candidate point based on image coordinates of the selected first image corneal reflection candidate point in the first image and image coordinates of the selected second image corneal reflection candidate point in the second image, and a twenty-fourth step of determining the calculated three-dimensional coordinates as corneal reflection of the subject when positions of the calculated three-dimensional coordinates and the detected three-dimensional coordinates of the pupil are within a specified range.

A facial posture detection method according to one aspect of the present invention detects a facial posture of a subject based on three-dimensional coordinates of one pair of pupils of a subject detected by the above-described pupil detection method.

A pupil tracking method according to one aspect of the present invention includes a twenty-fifth step of detecting one pupil pair of a subject by the above-described pupil detection method, a twenty-sixth step of acquiring images by taking a facial image of a subject using each of the first camera and the second camera, a twenty-seventh step of detecting one pupil pair of the subject at a first time after the step of detecting one pupil pair is performed and at a second time later than the first time, a twenty-eighth step of calculating absolute positions and relative positions of the one pupil pair detected at the first time and the second time, a twenty-ninth step of estimating absolute positions and relative positions of the one pupil pair at a third time later than the second time based on the calculated absolute positions and relative positions of the one pupil pair at the first time and the second time, a thirties step of estimating image coordinates of each pupil of the one pupil pair at the third time based on the estimated absolute positions and relative positions of the one pupil pair at the third time, a thirty-first step of setting a small region around the estimated image coordinates of the pupil in each of the images taken by the first camera and the second camera at the third time, and a thirty-second step of determining a position of a pupil by specified image processing in the set small region and calculating image coordinates of the pupil at the third time in each of the images taken by the first camera and the second camera at the third time.

Advantageous Effects of Invention

According to the present invention, it is possible to provide a pupil detection method and tracking method that can improve robustness and accuracy without imposing restrictions on the rotation of a user's head and the positions of cameras.

BRIEF DESCRIPTION OF DRAWINGS

FIG. 28 is a view showing a facial posture detection method according to this embodiment.

DESCRIPTION OF EMBODIMENTS

Figure 1:
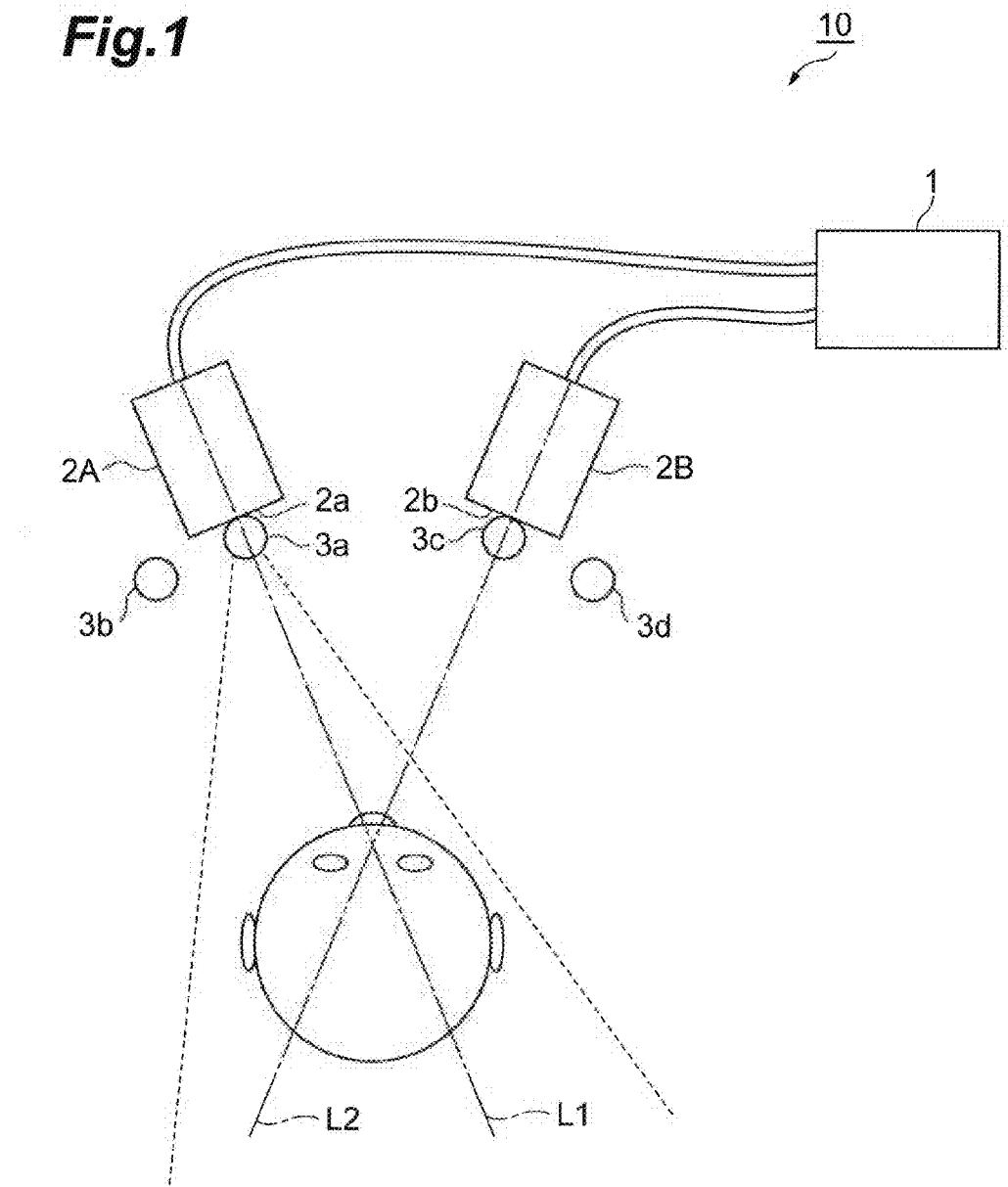
FIG. 1 is a plan view showing a pupil detection device to implement a preferred embodiment of the present invention.

A preferred embodiment of a pupil detection method according to the present invention will be described hereinafter in detail with reference to the drawings. Note that, in the description of the drawings, the same or equivalent elements are denoted by the same reference numerals and repeated explanation thereof is omitted.

(Pupil Detection Device for Performing Pupil Detection Method)

First, the configuration of a pupil detection device for performing a pupil detection method according to the present invention is described hereinafter with reference to the drawings. The pupil detection device is used as a pointing device that moves a cursor on a monitor screen of a personal computer by detecting pupil movement, a drowsiness detection system that detects the drowsiness of a driver by monitoring the motion of pupils and the like.

FIG. 1 is a plan view showing a pupil detection device 10 according to one preferred embodiment of the present invention. As shown in FIG. 1, the pupil detection device 10 includes a left camera 2A and a right camera 2B, which are two cameras for taking a head image of a subject A, a light source 3a placed in close proximity to an imaging lens on a front face 2a of the left camera 2A, a light source 3b placed at a distance from the front face 2a of the left camera 2A, a light source 3c placed in close proximity to an imaging lens on a front face 2b of the right camera 2B, a light source 3d placed at a distance from the front face 2b of the right camera 2B, and an image processing device 1 that is connected with the left camera 2A, the right camera 2B and the light sources 3a to 3d.

Although the left camera 2A and the right camera 2B are not limited to those of a particular type as long as they are imaging means capable of generating a facial image of the subject A, a digital camera having an imaging device such as CCD or CMOS is used because it can process image data in real time. One of the left camera 2A and the right camera 2B functions as a first camera and acquires a first image. The other one of the left camera 2A and the right camera 2B functions as a second camera and acquires a second image.

The light source 3a is configured to be able to emit illumination light having a near infrared component along a light axis L1 of the left camera 2A toward a range that covers the subject A on the light axis L1. The light source 3b is fixed at the position farther from the light axis L1 than the light source 3a and configured to be able to emit illumination light having a near infrared component along the light axis L1 toward a range that covers the subject A. The illumination light emitted from the two light sources 3a and 3b may have the same wavelength component, or more preferably, have different wavelength components so that the illumination light emitted from the light source 3a makes the pupils lighter than the illumination light emitted from the light source 3b (for example, the center wavelength of the light source 3a is 850 nm and the center wavelength of the light source 3b is 950 nm), and the light source 3b may be fixed at the position that is the same distance from the light axis L1 as the light source 3a. In this case, it is possible to simplify the configuration of and reduce the size of the light sources, allowing a difference in lightness to be produced in the pupil part. The positional relationship of the light sources 3c and 3d with the right camera 2B and the light axis L2 is the same as the positional relationship of the light sources 3a and 3b with the left camera 2A and the light axis L1.

Note that the left camera 2A, the right camera 2B and the light sources 3a to 3d are preferably placed at the lower position than the height of the face of the subject A (for example, the position where the angle of inclination of the light axis L1 or the light axis L2 with respect to the horizontal plane is 20 to 35 degrees, and the light axis L1 or the light axis L2 is pointing in the direction of the subject A) for the purpose of more easily preventing reflected light from appearing in the facial image when the subject A wears glasses.

The image processing device 1 controls the imaging by the left camera 2A and the right camera 2B and the emission of illumination light by the light sources 3a to 3d, and performs processing of detecting and tracking the pupils of the subject A based on the head images of the subject A acquired by the left camera 2A and the right camera 2B (which is described in detail later).

(Pupil Detection Method and Pupil Tracking Method)

Hereinafter, the operation of the above-described pupil detection device 10 is described, and further a pupil detection method and a pupil tracking method using the pupil detection device 10 are described.

(World Coordinate System and Camera Coordinate System)

Figure 2:
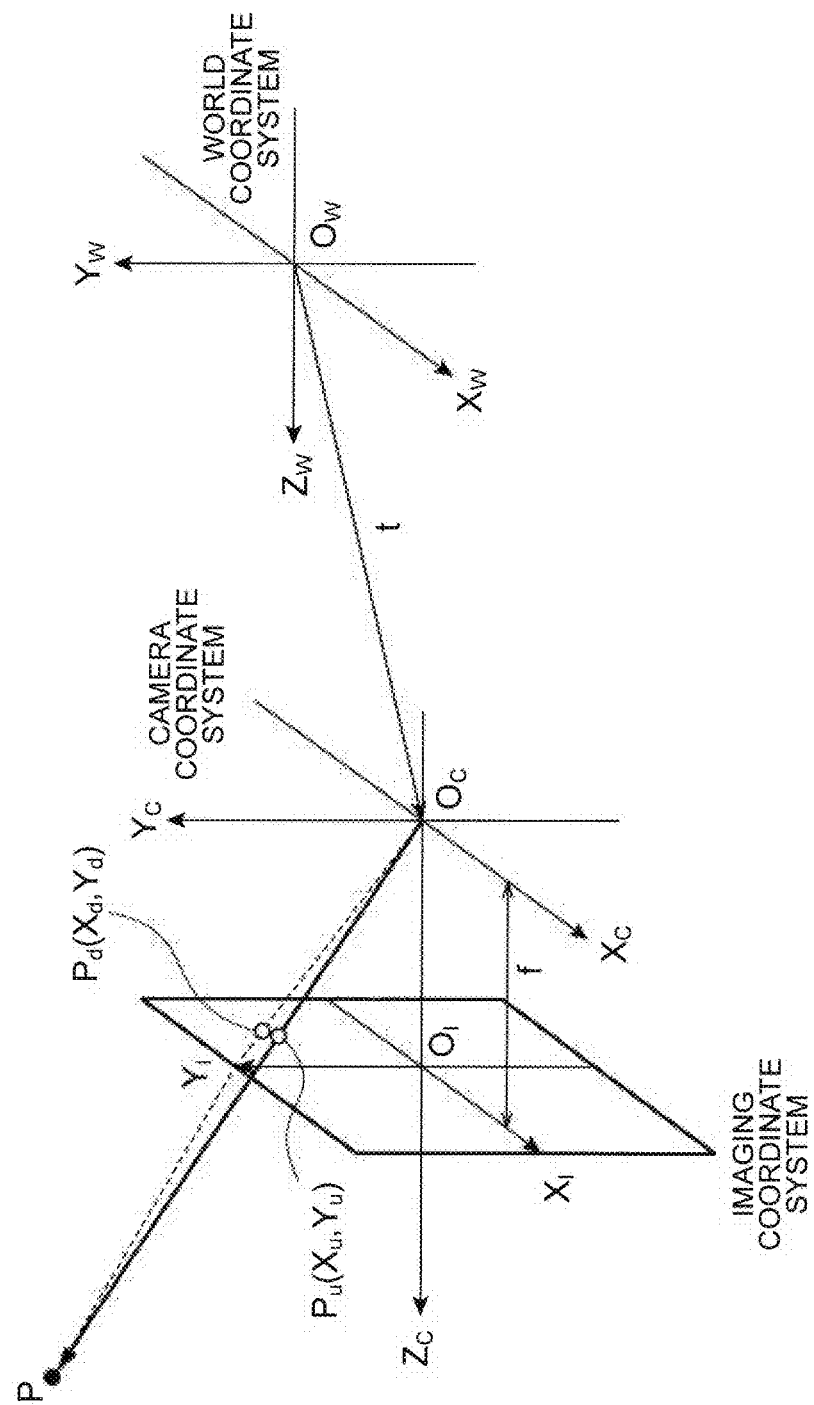
FIG. 2 is a view showing the relationship of a world coordinate system, a camera coordinate system and an imaging coordinate system.

First, the coordinate systems used in this embodiment are described. As shown in FIG. 2, consider the case where there is one camera in the world coordinate system. Although the camera coordinate system and the world coordinate system are parallel in this figure, those coordinate systems are not necessarily parallel.

When the vector from the origin point of the world coordinate system to the origin point of the camera coordinate system is t, and a 3×3 rotation matrix indicating the relative rotation of the coordinate system is R*, the coordinates and the vector C in each camera coordinate system can be transformed into the coordinates and the vector W in the world coordinate system by the following Equation (1).

[Math1]
$$W = R^* \cdot C + t \quad (1)$$

On the other hand, in the Tsai camera calibration method, a 3×3 rotation matrix R and a 3×1 translation vector T in the following Equation (2) are obtained as camera parameters.

[Math2]
$$C = R \cdot W + T \quad (2)$$

The rotation matrix R and the translation vector T are called external parameters that indicate the posture of the camera. In addition, in the Tsai camera calibration method, internal parameters that indicate the distortion of the camera or the like are obtained.

When the inverse matrix of the rotation matrix R is $R^{-1}$, the following Equation (3) is obtained from the above Equation (2).

[Math3]
$$W = R^{-1} \cdot [C - T] \quad (3)$$

T and $R^{-1}$ are as represented by the following Equations (4) and (5), respectively.

[Math4]
$$T = -R \cdot t \quad (4)$$

[Math5]
$$R^{-1} = R^* \quad (5)$$

Then, the following Equation (6) is obtained from Equation (3).

[Math6]
$$W = R^{-1} \cdot [C + R \cdot t] = R^{-1} \cdot C + t = R^* \cdot C + t \quad (6)$$

This Equation (6) is the same as Equation (1).

The camera coordinate system shown in FIG. 2 is the orthogonal coordinate system, and its origin point is $O_C$. Further, the X axis, the Y axis and the Z axis of the camera coordinate system are represented as the $X_C$ axis, the $Y_C$ axis and the $Z_C$ axis, respectively. In this pinhole model, it is assumed that the origin point $O_C$ is a pinhole position, the $Z_C$ axis is the light axis of the camera, and the imaging plane is located at the position at a focal length f from the origin point. The X axis of the imaging coordinate system is represented as the $X_I$ axis, and the Y axis is represented as the $Y_I$ axis. The $X_I$ axis and the $Y_I$ axis of the imaging coordinate system are respectively parallel to the $X_C$ axis and the $Y_C$ axis of the camera coordinate system. Further, the origin point $O_I$ of the imaging coordinate system is on the light axis of the camera coordinate system, which is on the $Z_C$ axis.

In this pinhole model, an object P to be imaged in the three-dimensional space that is taken by the camera is projected onto the intersection point $P_u(X_u, Y_u, f)$ between a straight line $PO_C$ connecting the object P to be imaged and the origin point $O_C$ of the camera coordinate system and the imaging plane. The position of $P_u$ corresponds to $(X_u, Y_u)$ in the imaging coordinate system.

Note that, in practice, image distortion occurs in the camera. Due to the image distortion, in the imaging coordinate system, P is projected not onto an ideal position $P_u(X_u, Y_u)$ but onto a point $P_d(X_d, Y_d)$ that is different from $P_u$. Note that, however, it is possible to correct $P_d(X_d, Y_d)$ using a distortion value obtained by the Tsai camera calibration and thereby calculate $P_u(X_u, Y_u)$. The correction of distortion of the camera is described later.

Figure 3:
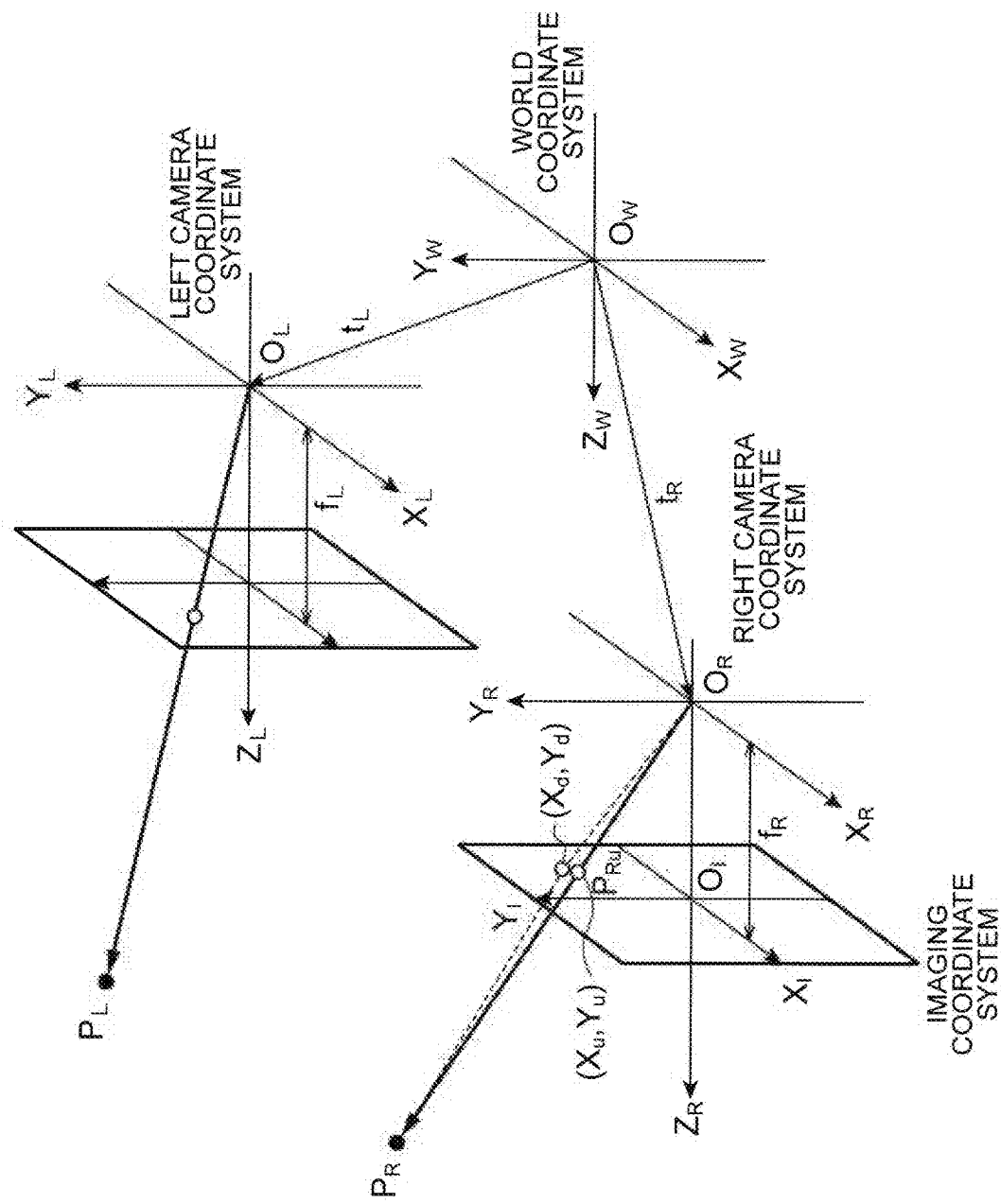
FIG. 3 is a view showing the relationship of a world coordinate system, a left camera coordinate system, a right camera coordinate system, and an imaging coordinate system.

Next, consider the case where there are two cameras. FIG. 3 shows the relationship of the coordinate systems when there are two cameras. In the case of representation in the world coordinate system, symbols have a superscript "W". Symbols having no superscript "W" are those of the right camera coordinate system or the left camera coordinate system.

From Equation (2), the origin point $O_R$ of the right camera coordinate system in FIG. 2 is represented by the following Equation (7) using the origin point $O_R^W$ of the right camera coordinate system in the world coordinate system.

[Math7]
$$O_R = R_R \cdot O_R^W + T_R = \begin{pmatrix} 0 \\ 0 \\ 0 \end{pmatrix} \quad (7)$$

$R_R$ is the rotation matrix when transforming the world coordinate system into the right camera coordinate system. $T_R$ is the translation vector when transforming the world coordinate system into the right camera coordinate system. The coordinates $P_{Ru}$ of the projected point can be also transformed into the world coordinate system in the same manner by the following Equation (8).

[Math8]
$$P_{Ru} = R_R \cdot P_{Ru}^W + T_R \quad (8)$$

Accordingly, the vector $O_R P_R$ from the origin point $O_R$ of the right camera to the projected point $P_{Ru}$ of the imaging plane is represented by the following Equation (9) using the vector $O_R^W P_{Ru}^W$ of the world coordinate system from the above Equations (3) and (4).

[Math9]
$$O_R P_{Ru} = P_{Ru} - O_R = R_R \cdot [P_{Ru}^W - O_R^W] = R_R \cdot O_R^W P_{Ru}^W \quad (9)$$

Thus, $O_R^W P_{Ru}^W$ is represented by the following Equation (10) from Equation (9).

[Math10]
$$O_R^W P_{Ru}^W = R_R^{-1} \cdot O_R P_{Ru} \quad (10)$$

Likewise, for the left camera, $O_L^W P_{Lu}^W$ is represented by the following Equation (11).

[Math11]
$$O_L^W P_{Lu}^W = R_L^{-1} \cdot O_L P_{Lu} \quad (11)$$

On the other hand, from Equation (3), the following Equation (12) holds for the right camera, and the following Equation (13) holds for the left camera.

[Math12]
$$O_R^W = R_R^{-1} \cdot [O_R - T_R] = -R_R^{-1} \cdot T_R \quad (12)$$

[Math13]
$$O_L^W = R_L^{-1} \cdot [O_L - T_L] = -R_L^{-1} \cdot T_L \quad (13)$$

From Equations (12) and (13), the vector $O_L^W O_R^W$ from the origin point $O_L^W$ of the left camera coordinate system to the origin point $O_R^W$ of the right camera coordinate system in the world coordinate system is obtained by the following Equation (14).

[Math14]
$$O_L^W O_R^W = -R_R^{-1} \cdot T_R + R_L^{-1} \cdot T_L \quad (14)$$

From Equation (4) and Equation (5), the first and second terms of Equation (14) correspond to the vectors $t_R$ and $t_L$ from the origin point of the world coordinate system to the origin point of each camera coordinate system in FIG. 3, respectively, and Equation (15) and Equation (16) are established.

[Math15]
$$t_R = -R_R^{-1} \cdot T_R \quad (15)$$

[Math16]
$$t_L = -R_L^{-1} \cdot T_L \quad (16)$$

Accordingly, from Equation (15) and Equation (16), Equation (14) can be represented as the following Equation (17).

[Math17]
$$O_L^W O_R^W = t_R - t_L \quad (17)$$

(Pupil Detection Method)

A pupil detection method according to this embodiment is described hereinafter. The pupil detection method according to this embodiment includes a first step of acquiring a first image by taking a facial image of a subject using a first camera, a second step of acquiring a second image by taking a facial image of a subject using a second camera, a third step of extracting one or more first image candidate points that are candidates for the pupil of the subject from the first image, a fourth step of extracting one or more second image candidate points that are candidates for the pupil of the subject from the second image, a fifth step of determining whether a combination of one of the first image candidate points and one of the second image candidate points corresponds to the same point in the three-dimensional space, a sixth step of extracting two or more space candidate points by setting the points in the three-dimensional space corresponding to the combination of the first image candidate point and the second image candidate point determined as corresponding to the same point in three-dimensional coordinates as the space candidate point, a seventh step of selecting a pair of two space candidate points among the extracted space candidate points and calculating the distance between the selected pair of two space candidate points for a plurality of pairs of space candidate points, an eighth step of excluding a pair of space candidate points where the calculated distance between the pair of space candidate points is not within a specified range, and a ninth step of determining one or more pairs of space candidate points among the pairs of space candidate points that have not been excluded and determining that a pair of pupils of the subject exist at positions of the determined one or more pairs of space candidate points.

Among the above steps, the third step of extracting first image candidate points from the first image can be performed by using a difference image obtained by calculating a difference between the pixel values of a light pupil image and a dark pupil image as the first image and selecting a point with a large pixel value in the difference image as the first image candidate point. Note that, however, the third step may be performed by another technique as long as a point that serves as a candidate for the pupil can be extracted based on image features such as a size and lightness specific to the pupil and the like in the first image. This is the same for the fourth step of extracting second image candidate points from the second image.

Hereinafter, the fifth step of determining whether a combination of one of the first image candidate points and one of the second image candidate points corresponds to the same point in the three-dimensional space and the sixth step of extracting two or more space candidate points by setting the point in the three-dimensional space corresponding to the combination of the first image candidate point and the second image candidate point determined to correspond to the same point in the three-dimensional coordinates as the space candidate point are described. Although three methods are described below as the processing method of the fifth step and the sixth step, some of the three methods may be performed in combination or all of the three methods may be performed in combination as appropriate in the pupil detection process.

The term "stereo matching" which is used in the following description is as follows. Generally, when obtaining the three-dimensional coordinates of an imaging object point using two cameras after camera calibration, which point in the image taken by each camera corresponds to the imaging object point is determined for each camera. The determined point in the image is referred to as an image candidate point. Then, the image candidate points in the images that are respectively taken by two cameras are associated with each other. The association of the image candidate points by two cameras is referred to as stereo matching. Accordingly, when both of the image candidate points obtained by two cameras correspond to the same imaging object point, stereo matching is done correctly.

(Extraction of Space Candidate Points)

Figure 4:
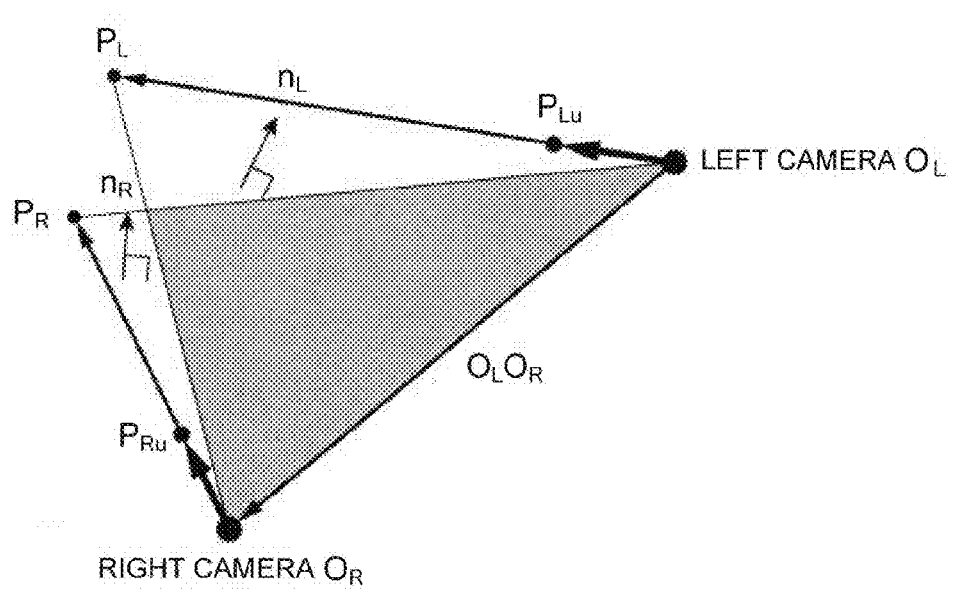
FIG. 4 is a view showing the positional relationship of left and right cameras and an object taken by the cameras.

A first method of extracting space candidate points is described with reference to FIG. 4. FIG. 4 is a simplified version of FIG. 3. It is assumed that all are represented in the world coordinate system. When the positions of objects appearing in the left and right camera images are $P_L$ and $P_R$, the vectors $O_L P_{Lu}$ and $O_R P_{Ru}$ in the same direction as the vectors $O_L P_L$ and $O_R P_R$ from the origin points of the respective cameras to those objects are obtained.

By the outer product of the vector $O_L P_{Lu}$ obtained by Equation (11) and the vector $O_L{}^W O_R{}^W$ obtained by Equation (17), the normal vector $n_L$ of the triangle $O_L P_L O_R$ is obtained by the following Equation (19).

[Math18]

$$n_L = O_L P_{Lu} \times O_L O_R \quad (18)$$

Likewise, the normal vector $n_R$ of the triangle $O_L P_R O_R$ is obtained by the following Equation (19).

[Math19]

$$n_R = -O_L P_{Ru} \times O_L O_R \quad (19)$$

When $P_L = P_R$, that is, when the same object is taken by the left and right cameras, $n_L = n_R$. When different objects are taken by the left and right cameras, $n_L \neq n_R$. To determine whether the left and right cameras take the same object, the angle $\theta$ between the plane $O_L P_L O_R$ and the plane $O_L P_R O_R$ is obtained by the following Equation (20) using the inner product of $n_L$ and $n_R$.

[Math20]

$$\cos \theta = \frac{n_L \cdot n_R}{|n_L||n_R|} \quad (20)$$

In practice, however, even when the left and right cameras take the same object, $P_L \neq P_R$ and $n_L \neq n_R$ due to limitations of the accuracy of object coordinate calculation from a camera image, the accuracy of camera calibration and the like. Therefore, in practice, using a threshold Th, it is determined that the left and right cameras take the same object when the following Equation (21) is satisfied.

[Math21]

$$Th < \cos \theta (\leq 1) \quad (21)$$

The value of Th is preferably 0.9995, for example. In this case, it corresponds to the range of $\theta = \pm 1.812°$ and the displacement of 25.31 mm for the object at a distance of 80.00 cm.

This first method is highly sensitive to the displacement of $P_L$ and $P_R$ around the axis being the straight line connecting the two cameras. So, the method is particularly effective.

However, on the contrary, even when the $n_L = n_R$ and the plane $O_L P_L O_R$ and the plane $O_L P_R O_R$ are parallel, $P_L = P_R$ is not always satisfied. An example of this case is shown in FIGS. 5(a) and 5(b). In this example, the plane $O_L P_L O_R$ and the plane $O_L P_R O_R$ are parallel. However, $P_L = P_R$ is not satisfied. Therefore, if the cameras are horizontally arranged, the displacement of $P_L$ and $P_R$ in the lengthwise direction can be detected; however, the displacement of $P_L$ and $P_R$ in the crosswise direction cannot be detected. Note that, however, the displacement in the crosswise direction is reflected as the displacement in the depth direction (Z direction) as a result of stereo matching between $P_L$ and $P_R$.

Figure 5:
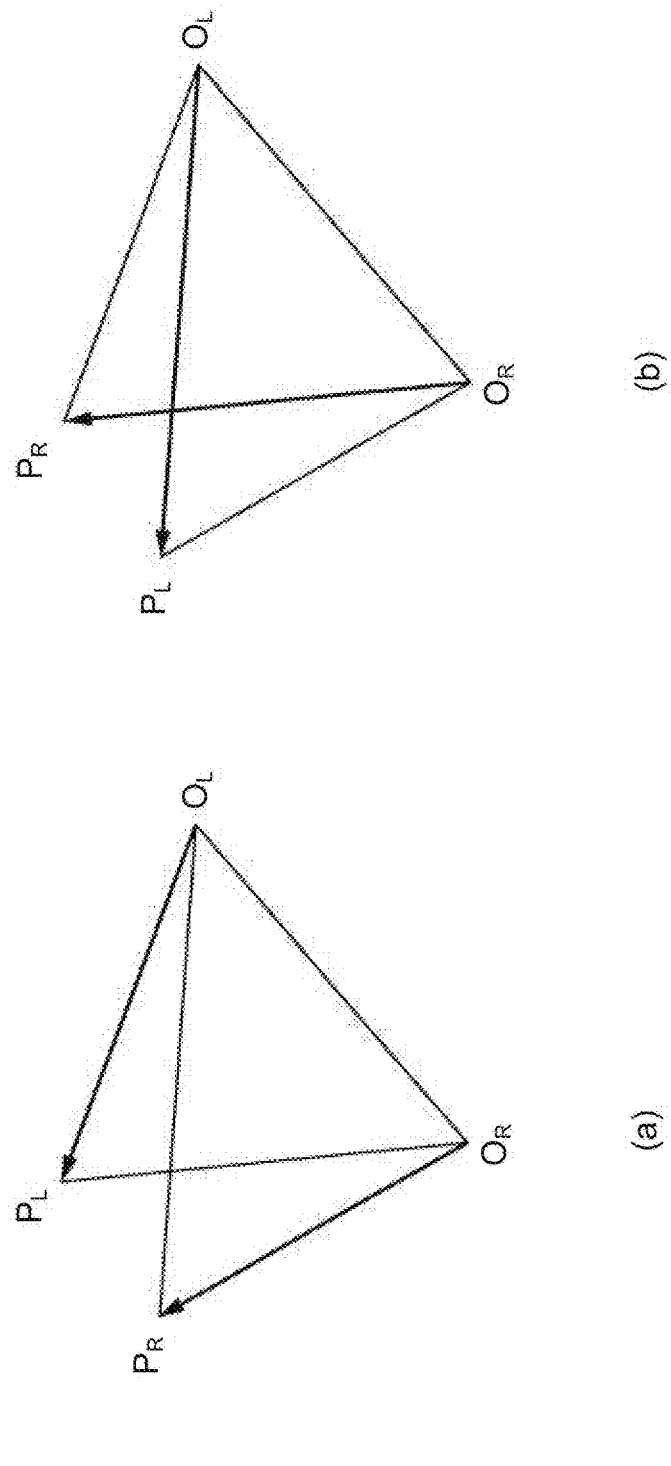
FIG. 5 is a view showing the positional relationship of left and right cameras and an object taken by the cameras.
Figure 6:
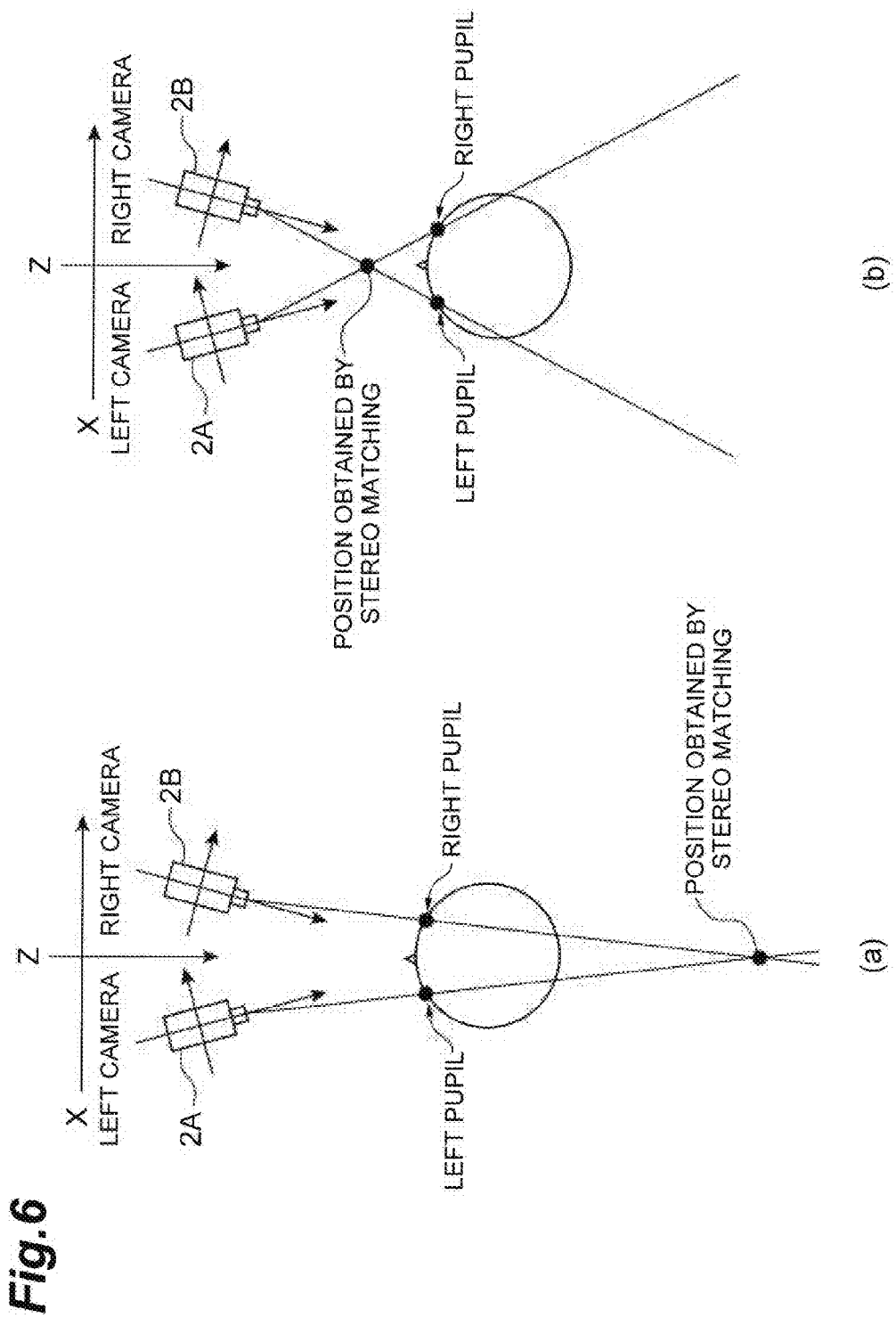
FIG. 6 is a view showing the positional relationship when images of different pupils are taken by left and right cameras.

FIG. 6 shows another representation of FIG. 5. FIG. 6(a) corresponds to FIG. 5(a), and FIG. 6(b) corresponds to FIG. 5(b). FIG. 5(a) and FIG. 6(a) show the case where the left camera 2A detects the left pupil $P_L$ and the right camera 2B detects the right pupil $P_R$. If stereo matching is performed on them, the three-dimensional coordinates of an object to be calculated are expected to be misdetected on far back of the subject's face. FIG. 5(b) and FIG. 6(b) show the case where the left camera 2A detects the right pupil $P_R$ and the right camera 2B detects the left pupil $P_L$. In this case, the three-dimensional coordinates of an object to be calculated are expected to be misdetected in far front of the subject's face. However, the displacement of the coordinates in the depth direction cannot be detected only by the above first method.

However, the above-described first method has an advantage that calculation after obtaining the coordinates of an object in the image in the imaging coordinate system is easy. Thus, when there are a large number of image candidate points detected by the left camera 2A and the right camera 2B, the first method is effective to exclude the image candidate points that do not correspond to the subject's pupil.

To be specific, the numbers of image candidate points obtained by the left and right cameras are $N_L$ and $N_R$, respectively. For those image candidate points, a series of calculations by the above-described first method are performed by combining them on a round-robin system. The number of combinations is $N_L \times N_R$. The combinations of image candidate points that are determined not to take the same object as a result of the calculations are excluded. Then, the coordinates of the image candidate points in the combinations that remain without being excluded are stored as the coordinates on the images of both cameras as valid candidates.

Next, a second method of extracting space candidate points is described.

Generally, a method of calculating the three-dimensional coordinates of an imaging object point from the coordinates of image candidate points obtained by stereo matching is as follows. This method is a method (3D reconstruction) using the rotation matrix R and the translation vector T (Equation (2)) calculated by the Tsai camera calibration.

The Z axis of the world coordinate system is set along the depth direction viewed from the camera. Further, R and T are represented by the following Equation (22) and (23), respectively,

[Math22]

$$R = \begin{pmatrix} r_1 & r_2 & r_3 \\ r_4 & r_5 & r_6 \\ r_7 & r_8 & r_9 \end{pmatrix} \quad (22)$$

[Math23]

$$T = \begin{pmatrix} T_x \\ T_y \\ T_z \end{pmatrix} \quad (23)$$

Generally, when the coordinates of an object P in the camera coordinate system are represented by $(X_C, Y_C, Z_C)$ (see FIG. 1), the following Equation (24) is established as a basic equation of the pinhole camera model.

[Math24]

$$X_u = f \frac{X_C}{Z_C} \quad (24)$$
$$Y_u = f \frac{Y_C}{Z_C}$$

On the basis of the above, when the coordinates of the object P in the world coordinate system are M, and M is transformed to apply to the equation of A·M=B, the following two equations are obtained for one camera. Note that the transformation of the equation in progress is not described.

[Math25]

$$\{X_u[r_7 r_8 r_9] - f[r_1 r_2 r_3]\} M = -T_z X_u + f T_x$$
$$\{Y_u[r_7 r_8 r_9] - f[r_4 r_5 r_6]\} M = -T_z Y_u + f T_y \quad (25)$$

One of the first image candidate points extracted from the first image acquired by the first camera is selected. Further, one of the second image candidate points extracted from the second image acquired by the second camera is selected. Then, two Equations that are the same as Equation (25) are obtained for each of the selected first image candidate point and second image candidate point. Thus, four equations (surplus equation) in three unknowns for M are obtained. Therefore, the value of M is obtained by the least-squares method as follows. If A is a square matrix, it is obtained by multiplying both sides of A·M=B by the inverse matrix $A^{-1}$ of A; however, because A is not a square matrix, there is no inverse matrix of A. Thus, M is obtained by the following equation (26) using $A^+$ by calculating $A^+ = (A^T A)^{-1} A^T$, which is the generalized inverse matrix (pseudo-inverse matrix) of A.

[Math26]

$$M = A^+ B = (A^T A)^{-1} A^T B \quad (26)$$

According to the second method, the three-dimensional coordinates of an object candidate point are specifically obtained. In the first method, even when there is an incorrect combination of image candidate points of the left and right cameras, this incorrect combination cannot be excluded in some cases. If the three-dimensional coordinates of an object point are obtained by the second method based on such an incorrect combination, the case where the left and right pupils are mixed up as shown in FIG. 5 can be determined by determining whether the distance from the relevant camera in the depth direction is within an appropriate range, which is, by determining whether the Z coordinate is within an appropriate range. This can be achieved by giving a range where the pupil of a subject exists as a threshold as in the following Equation (27).

[Math27]

$$Th_{Min} < (Z \text{ coordinate of } M) < Th_{max} \quad (27)$$

Further, the orientations of the two cameras are preferably set so that their light axes intersect with each other at one appropriate point, and when the intersection point is S, and the positions of the two cameras are $O_R$ and $O_L$, the orthogonal coordinate system where the Z axis is a axis connecting the midpoint of $O_R$ and $O_L$ and S may be defined, the coordinates of M in the coordinate system may be obtained, and then Equation (27) may be applied.

Particularly, because glasses reflection is a reflected image, it is not actually present at one point in the three-dimensional space. Accordingly, when viewed from the two cameras, the same imaging object point does not exist and it looks existing in different points. Therefore, if the three-dimensional coordinates of an object point are calculated by performing the second method when glasses reflection is the image candidate point, the value of the Z coordinate is not within an appropriate range, which tells that the glasses reflection is not the pupil. Therefore, when the calculated three-dimensional coordinate value is not within a specified appropriate range, the selected first image candidate point and second image candidate point can be excluded as not corresponding to the same point in the three-dimensional coordinates.

A third method of extracting space candidate points is described next.

The first method is effective for detecting an error of stereo matching in the direction around the axis being the straight line connecting the two cameras. In the case of distinguishing eyeball reflection from the pupil, accuracy is required because glasses reflection often appears in close proximity to the pupil. However, in the first method, the displacement is represented as an angle around the axis, and the distance from the axis to the subject's face cannot be taken into consideration. For example, even when the distance between the pupil and glasses reflection is the same in actual measurement, a threshold value should vary depending on the distance from the axis; however, it is not possible in the first method because the distance in the Z axis direction is not calculated.

In the third method, not only the distance in the Z axis direction that can be calculated in the second method but also the distance between object candidate points obtained by each camera at that distance can be obtained. Using those distances, it is determined whether stereo matching is correct or not. A calculation method is described hereinbelow.

Figure 7:
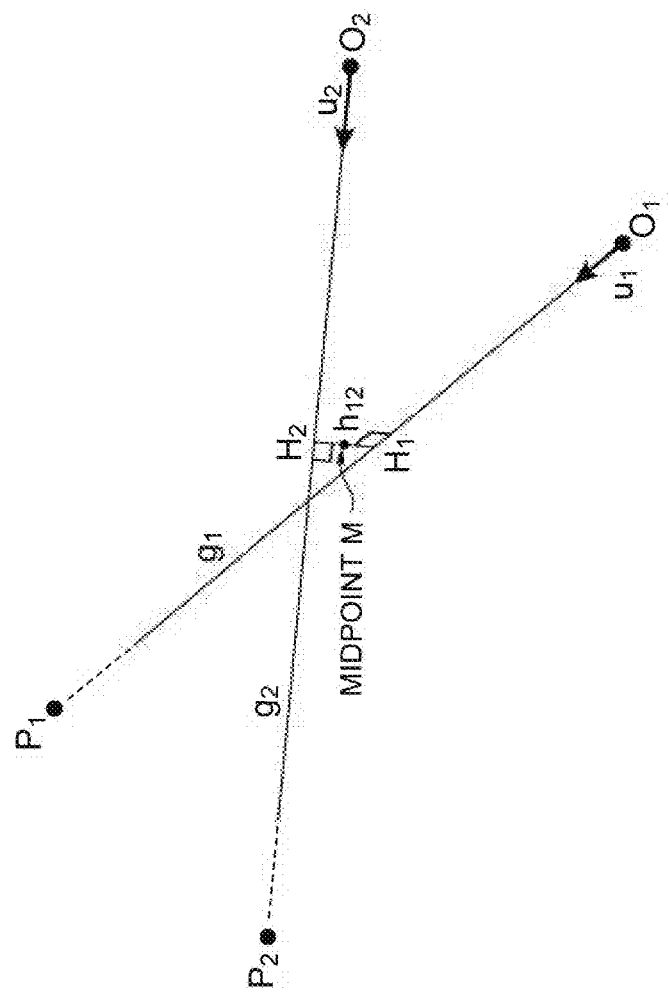
FIG. 7 is a view showing the positional relationship of left and right cameras and an object taken by the cameras.

The following is the description in the world coordinate system. In FIG. 7, there are two cameras, which are placed at points $O_1$ and $O_2$, for example. The camera at the point $O_1$ takes an object candidate point $P_1$, and the camera at the point $O_2$ takes an object candidate point $P_2$. The straight line connecting the point $O_1$ and the object candidate point $P_1$ is $g_1$ (first line), and the straight line connecting the point $O_2$ and the object candidate point $P_2$ is $g_2$ (second line). The vectors of the two lines $g_1$ and $g_2$ are $u_1 = (L_1, M_1, N_1)$ and $u_2 = (L_2, M_2, N_2)$, respectively. Those correspond to the vector $O_C P_u$ in FIG. 2. Further, the coordinates of the points $O_1$ and $O_2$ are $O_1 = (x_1, y_1, z_1)$ and $O_2 = (x_2, y_2, z_2)$, respectively.

The equations of the two lines $g_1$ and $g_2$ are represented as the following Equations (28) and (29), respectively.

[Math28]
$$g_1: \frac{x-x_1}{L_1} = \frac{y-y_1}{M_1} = \frac{z-z_1}{N_1} \tag{28}$$

[Math29]
$$g_2: \frac{x-x_2}{L_2} = \frac{y-y_2}{M_2} = \frac{z-z_2}{N_2} \tag{29}$$

A straight line (common perpendicular line) $h_{12}$ that is perpendicular to both of the lines $g_1$ and $g_2$ is given by the following Equation (30).

[Math30]
$$h_{12}: \frac{x-a_1}{M_1N_2 - N_1M_2} = \frac{y-b_1}{N_1L_2 - L_1N_2} = \frac{z-c_1}{L_1M_2 - M_1L_2} \tag{30}$$

The point $(a_1, b_1, c_1)$ is a point on the common perpendicular line and also a point on the line $g_1$, which is $H_1$. When the value of Equation (28) is t, the following Equation (31) is established.

[Math31]
$$\begin{cases} a_1 = L_1 t + x_1 \\ b_1 = M_1 t + y_1 \\ c_1 = N_1 t + z_1 \end{cases} \tag{31}$$

By substitution of Equation (31) into Equation (30), Equation (30) can be represented by the following Equation (32).

[Math32]
$$h_{12}: \frac{x-(L_1 t + x_1)}{M_1 N_2 - N_1 M_2} = \frac{y-(M_1 t + y_1)}{N_1 L_2 - L_1 N_2} = \frac{z-(N_1 t + z_1)}{L_1 M_2 - M_1 L_2} \tag{32}$$

Generally, the condition for the two lines $g_1$ and $g_2$ that are represented by Equations (28) and (29) to intersect with each other is establishment of the following Equation (33).

[Math33]
$$\begin{vmatrix} x_1 - x_2 & y_1 - y_2 & z_1 - z_2 \\ L_1 & M_1 & N_1 \\ L_2 & M_2 & N_2 \end{vmatrix} = 0 \tag{33}$$

Accordingly, the condition for the line $g_2$ represented by Equation (29) to intersect with the line $h_{12}$ represented by Equation (32) is establishment of the following Equation (34).

[Math34]
$$\begin{vmatrix} L_1 t + x_1 - x_2 & M_1 t + y_1 - y_2 & N_1 t + z_1 - z_2 \\ L_2 & M_2 & N_2 \\ M_1 N_2 - N_1 M_2 & N_1 L_2 - L_1 N_2 & L_1 M_2 - M_1 L_2 \end{vmatrix} =$$

$$(L_1 t + x_1 - x_2)\{M_2(L_1 M_2 - M_1 L_2) - N_2(N_1 L_2 - L_1 N_2)\} +$$
$$(M_1 t + y_1 - y_2)\{N_2(M_1 N_2 - N_1 M_2) - L_2(L_1 M_2 - M_1 L_2)\} +$$
$$(N_1 t + z_1 - z_2)\{L_2(N_1 L_2 - L_1 N_2) - M_2(M_1 N_2 - N_1 M_2)\} = 0 \tag{34}$$

$t = t_1$, and the following Equation (35) is given.

[Math35]
$$\begin{cases} A_1 = M_2(L_1 M_2 - M_1 L_2) - N_2(N_1 L_2 - L_1 N_2) \\ B_1 = N_2(M_1 N_2 - N_1 M_2) - L_2(L_1 M_2 - M_1 L_2) \\ C_1 = L_2(N_1 L_2 - L_1 N_2) - M_2(M_1 N_2 - N_1 M_2) \end{cases} \tag{35}$$

From Equation (34) and the Equation (35), the following Equation (36) is obtained.

[Math36]
$$t_1 = -\frac{A_1(x_1 - x_2) + B_1(y_1 - y_2) + C_1(z_1 - z_2)}{A_1 L_1 + B_1 M_1 + C_1 N_1} \tag{36}$$

By substitution of $t_1$ into Equation (31), the coordinates $(a_1, b_1, c_1)$ of $H_1$ are obtained as the following Equation (37).

[Math37]
$$H_1 = (a, b, c) = (L_1 t_1 + x_1, M_1 t_1 + y_1, N_1 t_1 + z_1) \tag{37}$$

Likewise, when the intersection point between the line $g_2$ (Equation (29)) and the common perpendicular line $h_{12}$ is $H_2 = (a_2, b_2, c_2)$, the following Equations (38) to (40) are obtained as the equations corresponding to the above-described Equations (35) to (37).

[Math38]
$$\begin{cases} A_2 = M_1(L_2 M_1 - M_2 L_1) - N_1(N_2 L_1 - L_2 N_1) \\ B_2 = N_1(M_2 N_1 - N_2 M_1) - L_1(L_2 M_1 - M_2 L_1) \\ C_2 = L_1(N_2 L_1 - L_2 N_1) - M_1(M_2 N_1 - N_2 M_1) \end{cases} \tag{38}$$

[Math39]
$$t_2 = -\frac{A_2(x_2 - x_1) + B_2(y_2 - y_1) + C_2(z_2 - z_1)}{A_2 L_2 + B_2 M_2 + C_2 N_2} \tag{39}$$

[Math40]
$$H_2 = (a_2, b_2, c_2) = (L_2 t_2 + x_2, M_2 t_2 + y_2, N_2 t_2 + z_2) \tag{40}$$

Finally, the distance $|H_1 H_2|$ between $H_1$ and $H_2$, which is, the shortest distance of the two lines $g_1$ and $g_2$, can be calculated from Equations (35) to (37), Equations (38) to (40) and the following Equation (41).

[Math41]
$$|H_1 H_2| = \sqrt{(a_1 - a_2)^2 + (b_1 - b_2)^2 + (c_1 - c_2)^2} \tag{41}$$

Further, the midpoint M of $H_1$ and $H_2$ can be easily obtained from the following Equation (42).

[Math42]
$$M = (x_M, y_M, z_M) = \left(\frac{a_1 + a_2}{2}, \frac{b_1 + b_2}{2}, \frac{c_1 + c_2}{2}\right) \quad (42)$$

If stereo matching is correct, the distance $|H_1H_2|$ is a small value, and the Z coordinate of the midpoint M is within the range where a subject exists. Therefore, by the third method, it can be determined whether the object candidate points $P_1$ and $P_2$ are the pupils or not. To be specific, it can be determined that stereo matching is correct based on the conditions that the calculated $|H_1H_2|$ is a specified threshold or less or the Z coordinate of the midpoint M is between a specified lower limit and a specified upper limit, or both of them.

Note that, although it is described in the description of the first method that the displacement of $P_L$ and $P_R$ in the lengthwise direction can be detected but the displacement of $P_L$ and $P_R$ in the crosswise direction cannot be detected when the cameras are arranged horizontally in the first method, the third method has the same problem.

(Method of Selecting Space Candidate Points Based on Distance Between Two Points)

Hereinafter, the seventh step of selecting a pair of two space candidate points among the extracted space candidate points and calculating the distance between the selected pair of two space candidate points for a plurality of pairs of space candidate points and the eighth step of excluding a pair of space candidate points where the calculated distance between the pair of space candidate points is not within a specified range are described. Note that, in this specification, this method is sometimes referred to as a fourth method.

The first to third methods for performing the fifth and sixth steps described above mainly aim at determining whether stereo matching is done correctly for each of the image candidate points. Then, in order to make sure that the space candidate points calculated from the image candidate points selected by the two cameras are actually the points obtained by taking the pupils of the subject, two space candidate points are paired up in this method, and it is determined whether the distance between the pair of space candidate points is a value within an appropriate range as the human inter-pupil distance, thereby determining whether the candidate pair of pupils are an actual pair of pupils. Further, this method is effective for detecting a pair of pupils of each subject or distinguishing between subjects in the case where two or more subjects are photographed.

Assume that a plurality of space candidate points are extracted by the process up to the sixth step. Two of the plurality of space candidate points are selected and combined as a pair. Then, the distance l between the combined pair of space candidate points is calculated based on the three-dimensional coordinates of the pair of space candidate points. This calculation of the distance l is performed for all pairs that can be combined. The distance l is represented by the following Equation (43). $P_1$ and $P_2$ are the three-dimensional coordinates of the combined pair of space candidate points, and $P_1$ and $P_2$ are different points.

[Math43]
$$l = |P_1 - P_2| \quad (43)$$

The number of space candidate points that can be combined as pupil pair candidates is given by the following Equation (44) when the number of space candidate points is N.

[Math44]
$$_NC_2 = \frac{N(N-1)}{2} \quad (44)$$

The pair of space candidate points where the calculated distance l is a value that is not appropriate as the human inter-pupil distance is determined not to be a pair of pupils, and that pair of pupils (both candidates for pupils) is excluded from the pupil pair candidates. On the other hand, the pair of space candidate points where the distance l is appropriate is determined to be the true pair of pupils, and each pupil candidate in the pupil pair is determined as the pupil. Generally, the human inter-pupil distance is about 65 mm. Thus, an appropriate range as the distance l is set to a specified range including 65 mm, taking variations in the inter-pupil distance due to individual differences or convergence into account. For example, when the distance l is not between 55 mm to 70 mm, the selected pair of space candidate points can be determined not to be the true pair of pupils and excluded from the pupil pair candidates.

Note that, in the case where two or more pairs of space candidate points remain after the above-described process is done, a pair of space candidate points may be determined as the pupils of a subject based on human behavioral characteristics, for example. For example, the pair of space candidate points where the angle of the line connecting the two space candidate points with respect to the horizontal plane is small may be determined as a pair of pupils on the assumption that there is no case where the line connecting two pupils is not significantly inclined with respect to the horizontal plane by leaning one's head to the side. Further, the pair of space candidate points that are similar to pupils in size, lightness and the like may be selected by image processing based on characteristics of the original image.

(Experiment of Pupil Detection Method)

A result of pupil detection experiment by the pupil detection method that combines the above-described methods is described hereinbelow.

The experimental environments and method were as follows. The experiment was conducted under the condition that, in a fluorescent lighted room, a subject wearing glasses sat at the position of about 80 cm from a camera, and light was applied to the face of the subject by an electric bulb. The reason for applying the light from the electric bulb is to induce false detection by reducing the pupils to the size close to glasses reflection. The illuminance near the subject's eyes was 366 to 751 lx.

The subject's head was not particularly fixed, and the subject was instructed to open and close the eyes several times during 300 frames, images were taken during that, and then pupil detection was conducted by the pupil detection method according to related art and the pupil detection method according to this embodiment.

Figure 8:
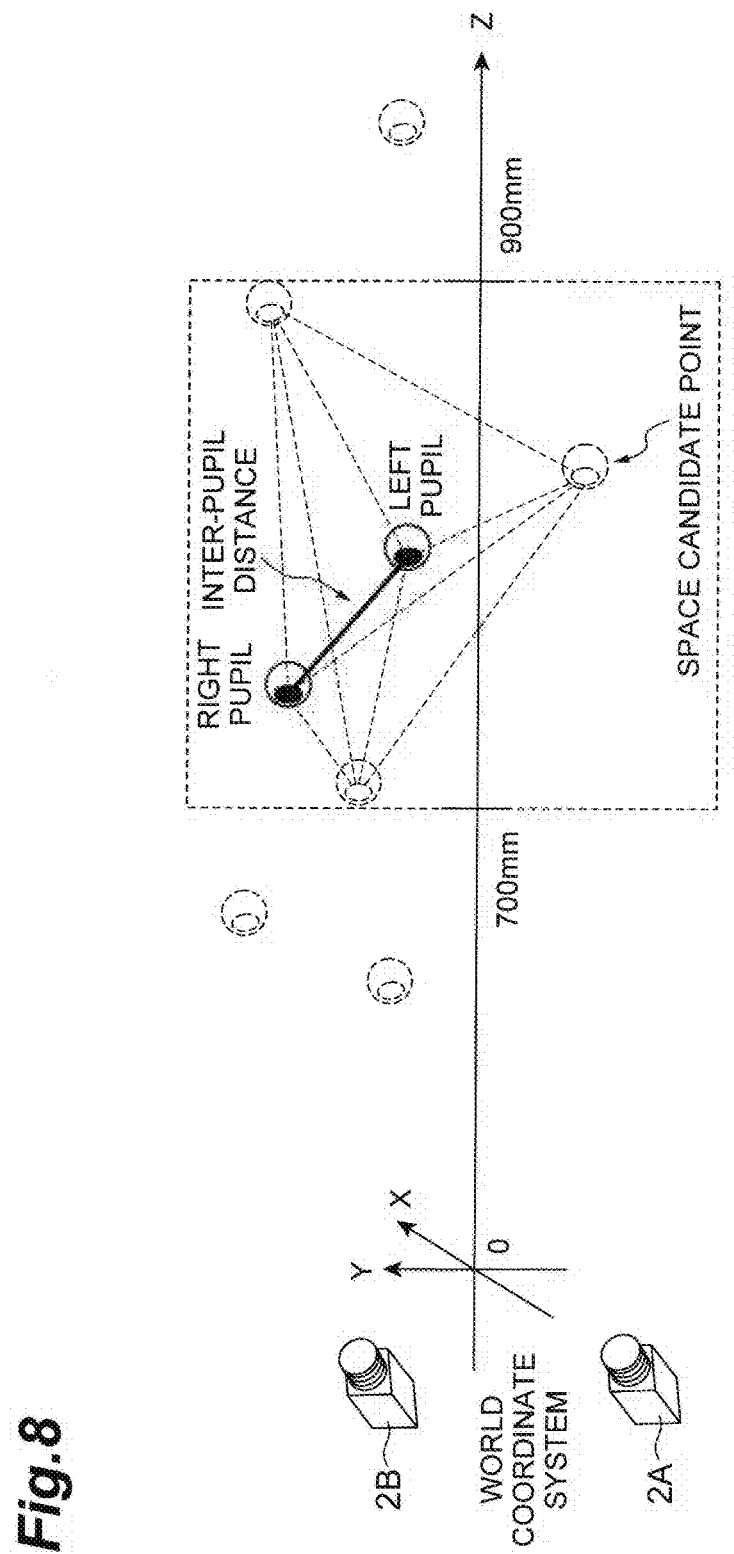
FIG. 8 is a view showing a method of detecting a pair of left and right pupils based on an inter-pupil distance and coordinates.

A specific process of the pupil detection method according to this embodiment in this experiment is described with reference to FIG. 8. First, up to fifth image candidate points were detected by image processing using each of two cameras. Next, the detected image candidate points by the two cameras were respectively combined into a pair, and stereo matching was performed by the second method using the pair of image candidate points, and the three-dimensional coordinates of the space candidate points corresponding to the pair of image candidate points were calculated. Assuming that the subject's face was at a distance of about 80 cm from the camera, when the Z coordinate along the Z axis extending away from the camera among the three-dimensional coordinates was not within the range of 70 cm to 90 cm, it was determined that the pairing of image candidate points was wrong, and the pair of image candidate points were excluded. After that, a pair of space candidate points which satisfied the condition for the distance in the Z axis direction and where the distance between the two space candidate points was between 63 to 70 mm were determined as the true pupils.

Figure 9:
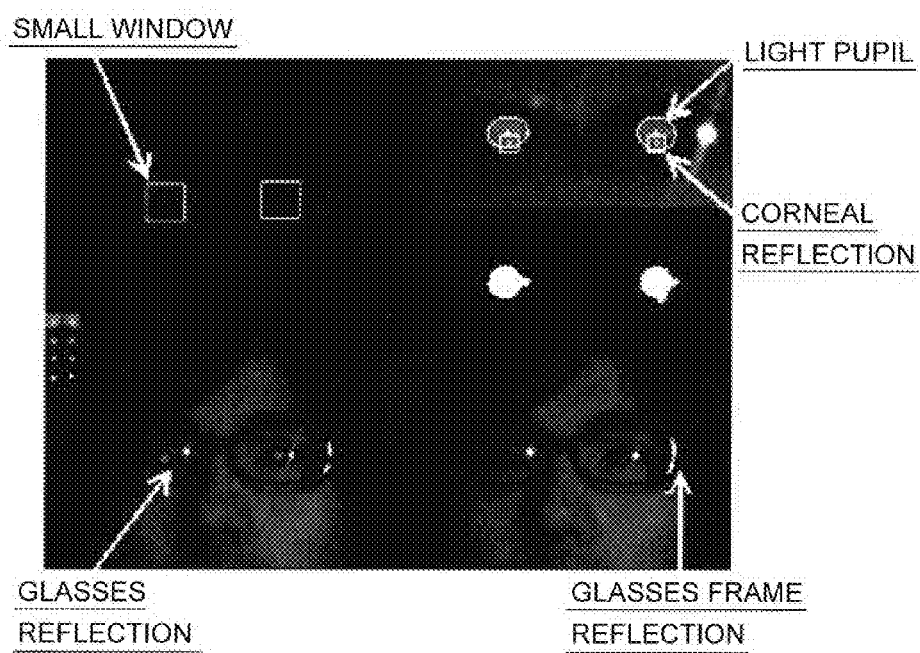
FIG. 9 is a view showing a pupil detection result by a pupil detection method according to this embodiment.

FIG. 9 is a picture showing an image taken in this experiment and a result of conducting various processing on the image. FIG. 9 is largely divided into a lower left part, a lower right part, an upper left part and an upper right part, and the upper right part is further divided into an upper half and a lower half. The lower left part of FIG. 9 is a light pupil image in which the pupils of a subject appear light. The lower right part of FIG. 9 is a dark pupil image in which the pupils of a subject appear dark. The upper left part of FIG. 9 is a difference image created by taking differences in pixel values between the light pupil image and the dark pupil image. The upper half of the upper right part of FIG. 9 is a light pupil image created by enlarging the pupil parts of the subject and converting it into high-resolution. The lower half of the upper right part of FIG. 9 is an image created by binarizing the high-resolution light pupil image in the upper half of the upper right part of FIG. 9. Note that the images are arranged in the same manner in FIGS. 10, 11 and 26 described later.

In the light pupil image in the lower left part of FIG. 9 and the dark pupil image in the lower right part of FIG. 9, glasses reflection that is reflection of light by the lens of glasses and glasses frame reflection that is reflection of light by the frame of glasses appears. Such glasses reflection is removed to a certain degree in the difference image. Further, because the lightness of the pupils of the subject is largely different between the light pupil image and the dark pupil image, the parts corresponding to the pupils of the subject appear light in the difference image in the upper left part of FIG. 9.

Then, based on the image features such as the lightness, size and the like of the light parts, the image processing device 1 detects that there are pupils in those parts and displays small windows (small regions) in the pupil parts. The small windows are to estimate the positions of pupils and limit target regions to search for pupils when performing a pupil tracking process, which is described later. The image processing device 1 searches for a figure that is considered to be a pupil in this small window and thereby performs the pupil tracking process. In the upper right part of FIG. 9, almost circular figures are displayed at the positions overlapping the light pupils of the target. Note that the small square figures displayed in the upper right part of FIG. 9 indicate corneal reflection, which is reflection of light by the corneas of the subject. Detection of corneal reflection is described later.

Figure 10:
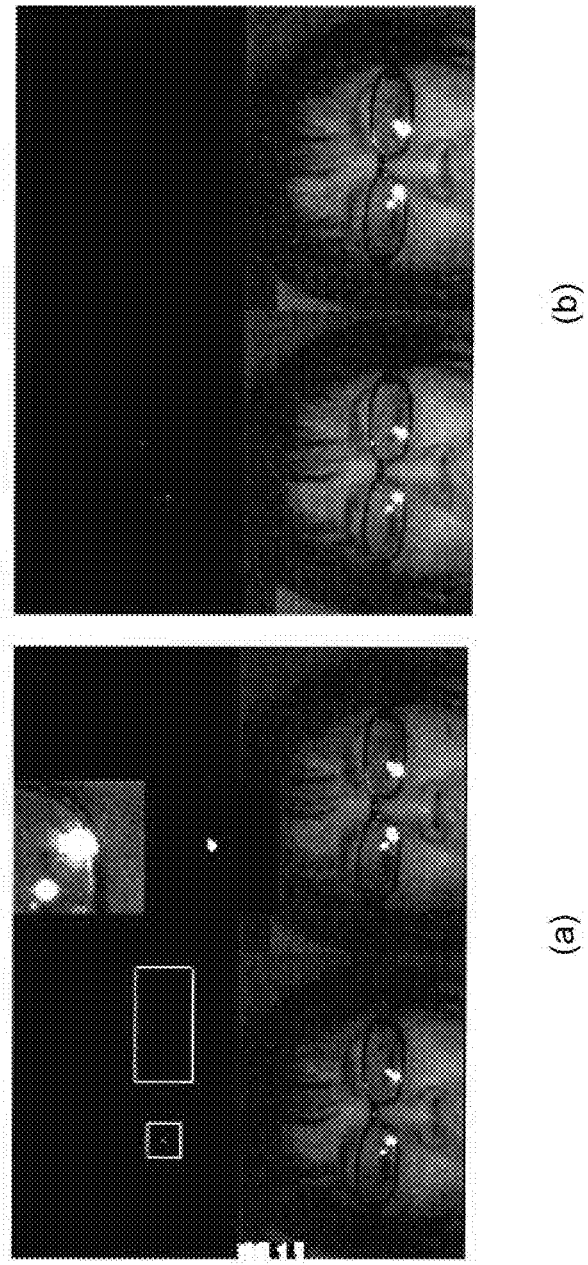
FIG. 10 is a view showing comparison between a pupil detection result by a pupil detection method according to related art and a pupil detection result by a pupil detection method according to this embodiment.

FIG. 10 show processing images when a subject closes the eyes. FIG. 10(a) is a processing image by the pupil detection method according to related art, and FIG. 10(b) is a processing image by the pupil detection method according to this embodiment. In both of FIGS. 10(a) and 10(b), glasses reflection by the right eye lens part of glasses remains as a white point in the difference image. In FIG. 10(a), the white point by glasses reflection is misdetected as a pupil, and a small square is displayed in this part. On the other hand, in FIG. 10(b), the white point by glasses reflection is not detected as a pupil and undetected.

Figure 11:
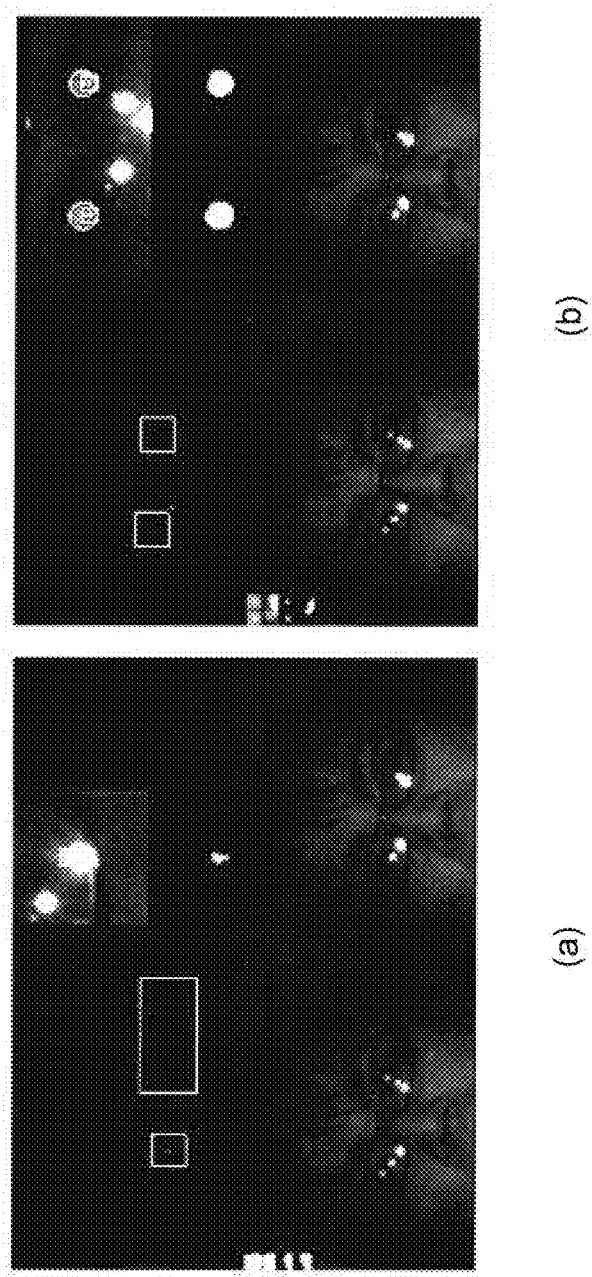
FIG. 11 is a view showing comparison between a pupil detection result by a pupil detection method according to related art and a pupil detection result by a pupil detection method according to this embodiment.

FIG. 11 show processing images immediately after the subject opens the eyes, which is later than FIG. 10. FIG. 11(a) is a processing image by the pupil detection method according to related art, and FIG. 11(b) is a processing image by the pupil detection method according to this embodiment. In FIG. 11(a), glasses reflection is misdetected as a pupil, just like in FIG. 10(a). On the other hand, in FIG. 11(b), pupils whose image can be now taken by the camera because the subject open the eyes are detected correctly.

Figure 12:
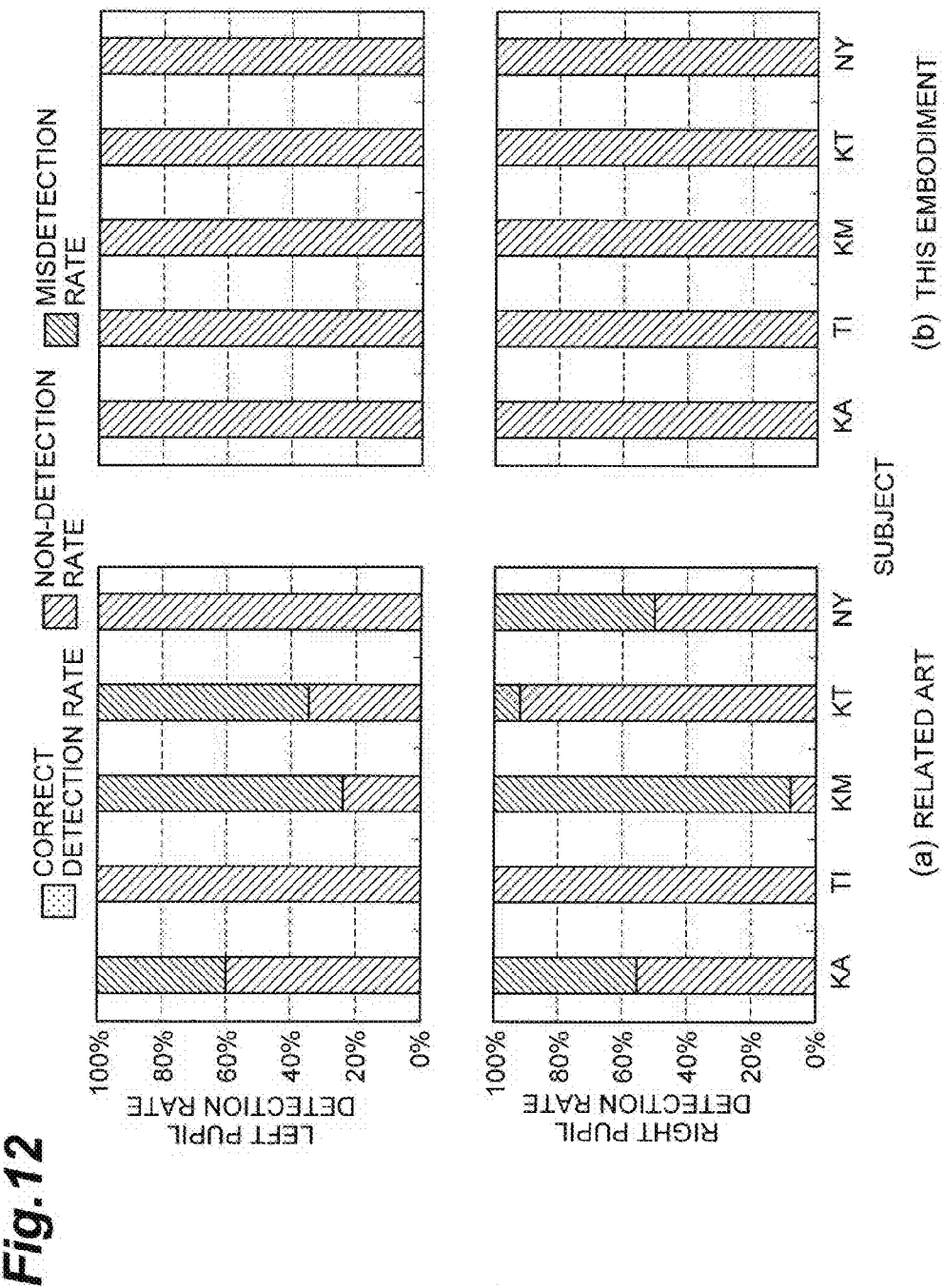
FIG. 12 is a view showing comparison between a pupil detection rate by a pupil detection method according to related art and a pupil detection rate by a pupil detection method according to this embodiment.

FIG. 12 show the pupil detection rate by the left camera when a subject closes the eyes. FIG. 12(a) shows the pupil detection rate by the pupil detection method according to related art. FIG. 12(b) shows the pupil detection rate by the pupil detection method according to this embodiment. Both of FIGS. 12(a) and 12(b) show the detection rate of each of the left and right pupils of five subjects. The correct detection rate indicates the percentage of cases where pupils can be detected correctly. The non-detection rate indicates the percentage of cases where the positions of pupils are not detected. The misdetection rate indicates the percentage of cases where those other than pupils, such as glasses reflection, are misdetected as pupils. Once misdetection is done, in the tracking of the pupils using the pupil tracking method, which is described later, the wrongly detected glasses reflection is tracked, misrecognizing that it is the pupil, and therefore the pupils cannot be detected for a long time. Thus, misdetection is not preferable.

In the case where a subject closes the eyes, the pupils do not appear in the camera image. Thus, it is correct that the pupils are not detected. Therefore, when a subject closes the eyes, it is preferred that the correct detection rate is 0%, the non-detection rate is 100%, and the misdetection rate is 0%. In the case of using the pupil detection method according to related art shown in FIG. 12(a), misdetection occurs for many subjects. On the other hand, in the case this embodiment shown in FIG. 12(b), misdetection does not occur for all subjects. Note that, for the right camera also, substantially the same pupil detection rate as for the left camera is obtained.

Figure 13:
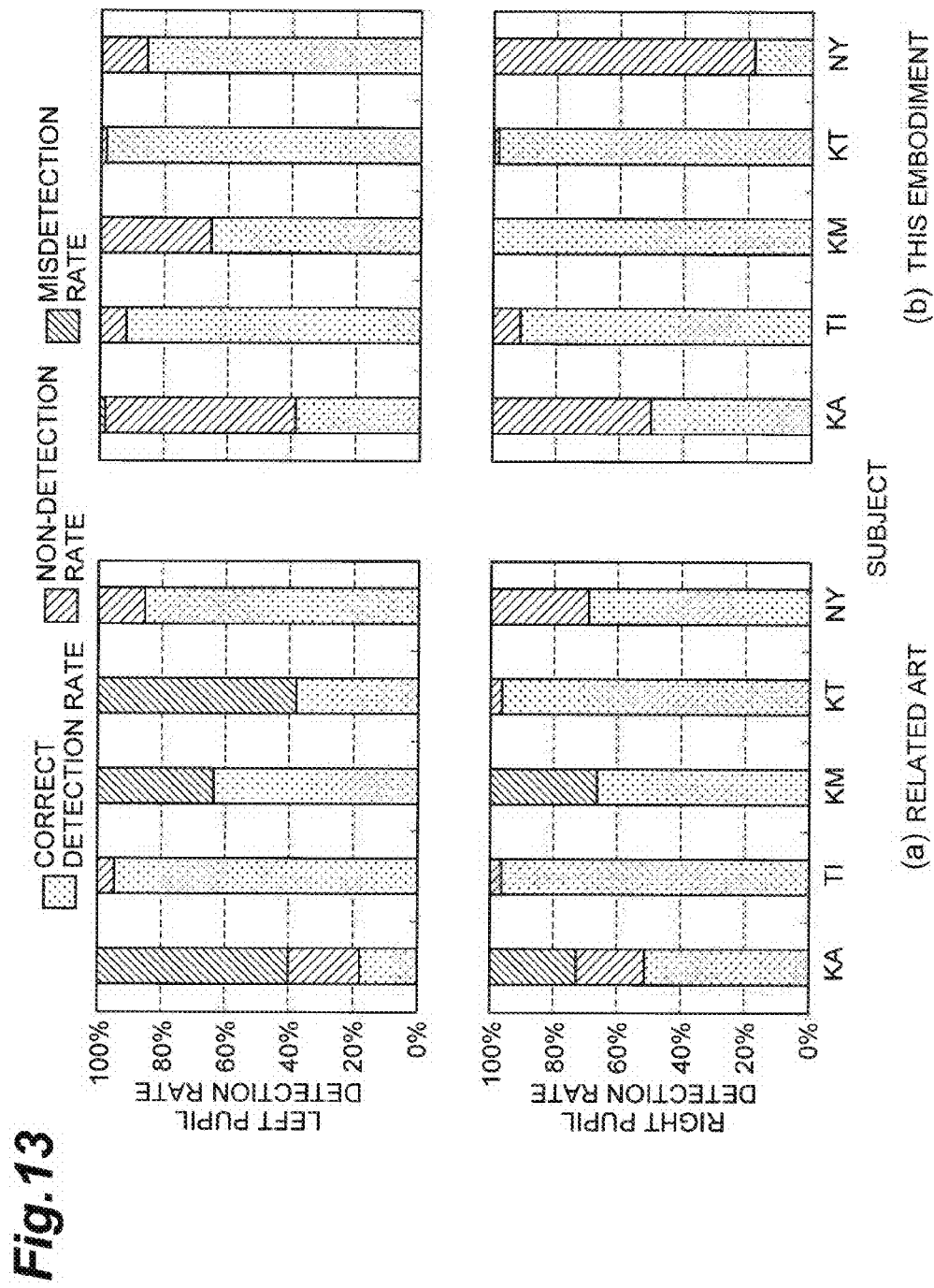
FIG. 13 is a view showing comparison between a pupil detection rate by a pupil detection method according to related art and a pupil detection rate by a pupil detection method according to this embodiment.

FIG. 13 show the pupil detection rate by the left camera when a subject opens the eyes. FIG. 13(a) shows the pupil detection rate by the pupil detection method according to related art. FIG. 13(b) shows the pupil detection rate by the pupil detection method according to this embodiment. In the case when a subject opens the eyes also, while misdetection occurs in a certain percentage in the pupil detection method according to related art, misdetection does not substantially occur in the pupil detection method according to this embodiment.

(Method of Detecting Pupil Pairs of Several Persons)

A case of detecting pairs of pupils of a plurality of persons is described hereinafter.

In the case of detecting pupil pairs of a plurality of persons also, pupil pairs of a plurality of persons can be detected by the method that extracts space candidate points by the above-described first to third methods and then selects space candidate points based on the distance between two points. For example, inappropriate image candidate points are deleted by the first method, then inappropriate image candidate points among the image candidate points that have not been deleted are determined and deleted by the second method, the three-dimensional coordinates corresponding to the remaining image candidate points are calculated, and determination is made by selecting the two points whose calculated three-dimensional coordinates are within a specified range, thereby detecting pairs of pupils of a plurality of persons.

Figure 14:
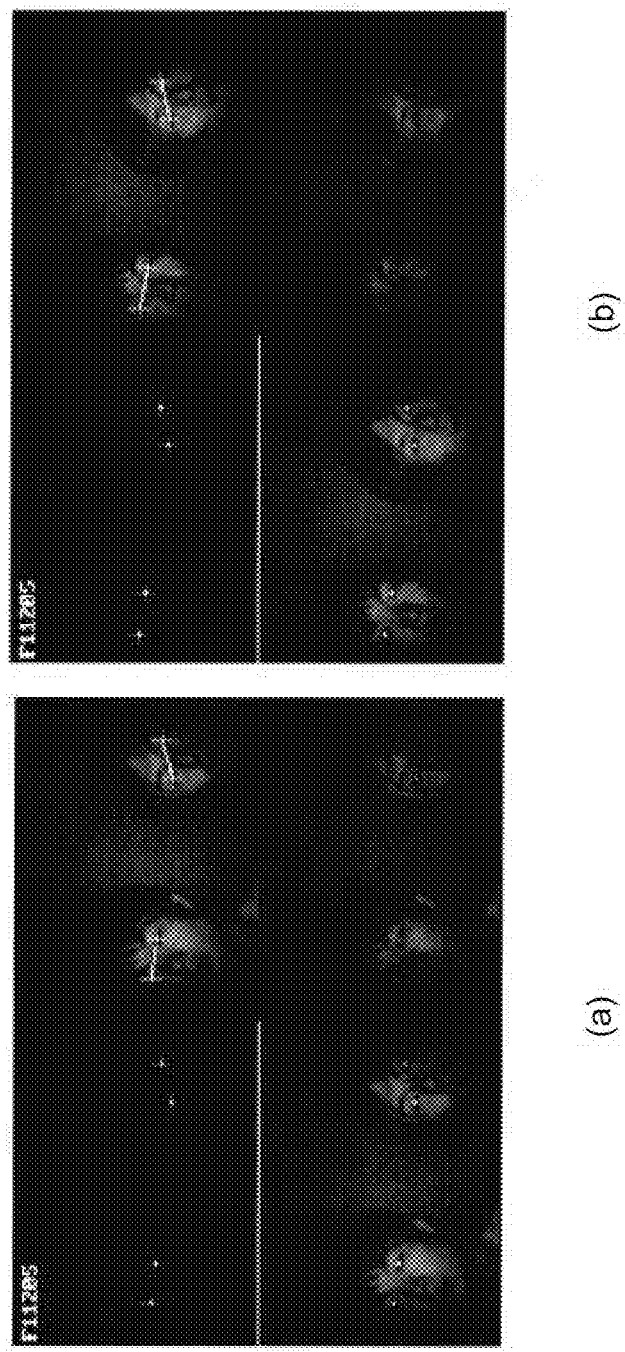
FIG. 14 is a view showing a detection result of a pair of pupils of two persons by a pupil detection method according to this embodiment.

FIG. 14 shows an experimental result in the case of conducting pupil detection on two subjects by performing the method of selecting space candidate points based on the distance between two points after sequentially performing the first and second methods. FIG. 14(a) shows an image taken by the left camera. FIG. 14(b) shows an image taken by the right camera. Each of FIG. 14(a) and FIG. 14(b) is composed of four images. The lower left image is a light pupil image acquired by taking an image of a subject. The lower right image is a dark pupil image acquired by taking an image of the subject. The upper left image is a difference image created by taking differences in pixel values between the light pupil image and the dark pupil image. In the upper left image, the white cross figures indicate the positions of pupils detected by the pupil detection process. The upper right image shows a result of detecting a pair of left and right pupils of the same person. In the upper right image, the white cross figures indicate the positions of pupils detected by the pupil detection process. Further, the white straight line connecting the white cross figures is a line connecting the points detected as a pair of left and right pupils of the same person.

Note that, in the case of detecting pupils of a large number of subjects, all of the subjects are not always standing in line at the positions of the same depth from the camera. Thus, if the pupil candidate points whose Z coordinate is not within a certain range is excluded by the second method or the pupil candidate points whose Z coordinate of the midpoint M is not within a certain range is excluded by the third method, pupil pairs of all subjects cannot be detected in some cases. Therefore, in such a case, pupil pairs of subjects are determined by sequentially carrying out extraction of space candidate points by performing the first method and the third method using the shortest distance between two lines and selection of space candidate points according to the distance between two points. In this case, either one of the first method or the third method can be omitted.

(Corneal Reflection Detection Method)

A corneal reflection detection method according to this embodiment is described hereinafter.

Figure 15:
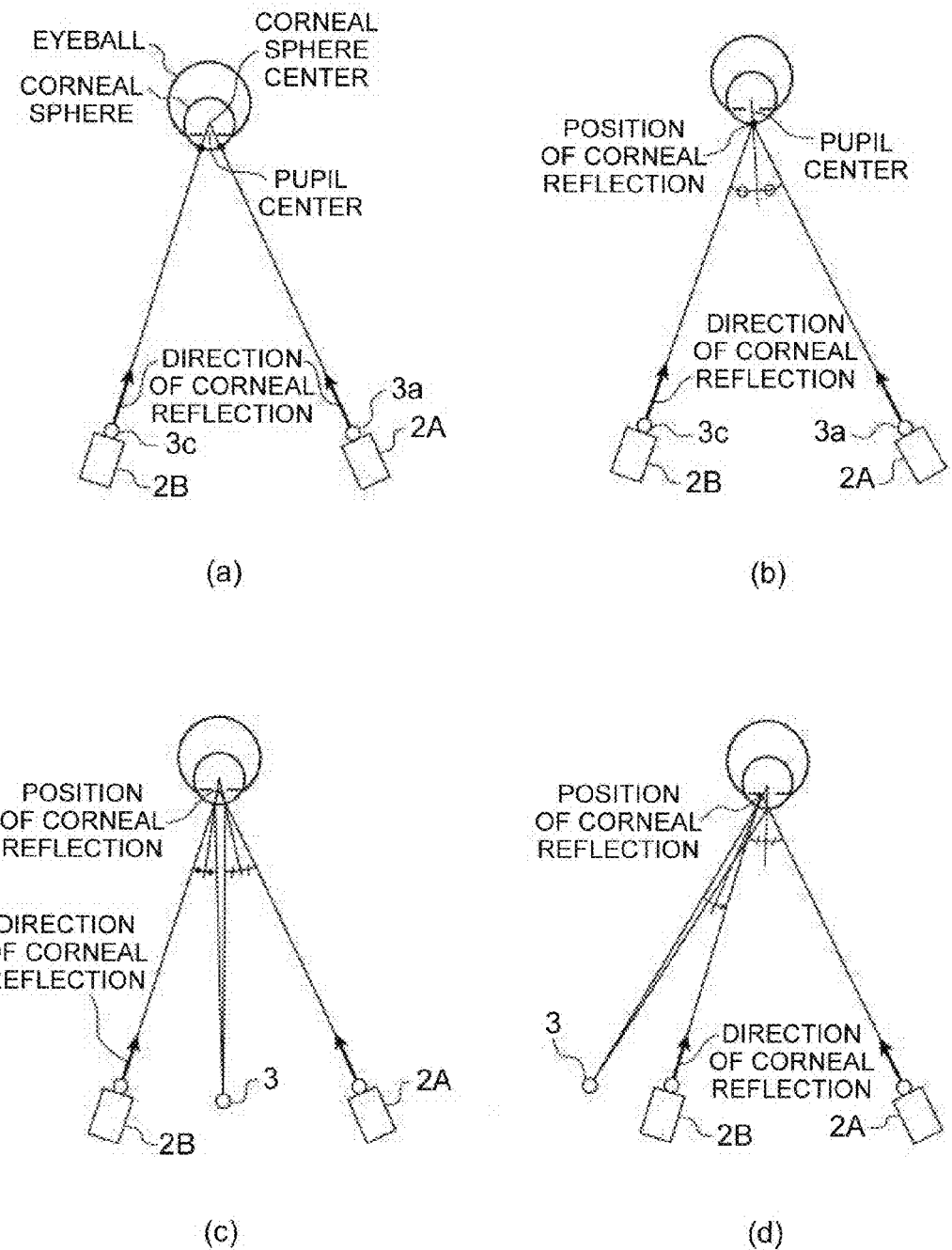
FIG. 15 is a view showing a corneal reflection detection method according to this embodiment.

FIG. 15 is a view schematically showing a device for performing a corneal reflection detection method according to this embodiment and the eyeball of a subject. In this corneal reflection detection method, a left camera 2A, a right camera 2B, and a light source 3 (3a and 3c) are used. Further, prior to detecting the cornea, the above-described pupil detection method is performed using the left camera 2A and the right camera 2B to detect the three-dimensional coordinates of the pupils. The method is described hereinafter for each case where the positions of the left camera 2A, the right camera 2B, and the light source 3 (3a and 3c) are different.

First, the case of FIG. 15(a) is described. In this case, the light source 3a is placed in close proximity to the camera 2A. Further, the light source 3c is placed in close proximity to the camera 2B.

A first image is acquired by the left camera 2A, applying light from the light source 3a to the eyeball. Further, a second image is acquired by the right camera 2B, applying light from the light source 3c to the eyeball. Then, corneal reflection of light from the light source 3a on the cornea appears in the first image, and corneal reflection of light from the light source 3c on the cornea appears in the second image. The shape of the cornea is spherical, called a corneal sphere. Therefore, the corneal reflection appearing in each of the first image and the second image appears as if it is emitted from a light source at the center of the corneal sphere.

Thus, when one or more first image corneal reflection candidate points, which are candidates for corneal reflection of the subject, are extracted from the first image, one or more second image corneal reflection candidate points, which are candidates for corneal reflection of the subject, are extracted from the second image, one point is selected from each of the first and second corneal reflection candidate points, and the three-dimensional coordinates are calculated by the above-described second or third method using the image coordinates of the selected points, the results are obtained as if there is a light source at the center of the corneal sphere. After obtaining the three-dimensional coordinates that serve as a candidate for corneal reflection, it is determined that the obtained candidate for corneal reflection is actual corneal reflection when the obtained three-dimensional coordinates of the corneal reflection candidate is within a specified range from the previously detected three-dimensional coordinates of the pupil, such as within a range of several mm, for example.

In the case of FIG. 15(b), the positions of the light sources 3a and 3b are the same as in the case of FIG. 15(a). However, the light source used when taking an image is different from that of FIG. 15(a). Specifically, a first image is acquired by the left camera 2A, applying light from the light source 3c to the eyeball, and a second image is acquired by the right camera 2B, applying light from the light source 3a to the eyeball. After that, the three-dimensional coordinates that serve as a candidate for corneal reflection are obtained in the same manner as in FIG. 15(a). Then, the obtained three-dimensional coordinates are on the surface of the corneal sphere. In this case also, it can be determined that the obtained corneal reflection candidate is actual corneal reflection when the distance between three-dimensional coordinates of the corneal reflection candidate and the three-dimensional coordinates of the pupil is within a range of several mm.

In the case of FIG. 15(c) and FIG. 15(d), one light source 3 is used instead of the light sources 3a and 3b. Thus, light from the light source 3 is applied to the subject's eyeball both when acquiring a first image by the left camera 2A and when acquiring a second image by the right camera 2B. In this case, the obtained position of corneal reflection differs depending on the position of the light source 3. In any case, it can be determined that the obtained corneal reflection candidate is actual corneal reflection when the distance between three-dimensional coordinates of the corneal reflection candidate and the three-dimensional coordinates of the pupil is within a range of several mm.

(Method of Detecting Pupils Using Three or More Cameras)

The method of detecting pupils using two cameras only is described above. However, the pupil detection method using two cameras described above may be performed by taking a facial image of a subject using at least three cameras, selecting at least two sets of the first camera and the second camera among those cameras, and using each of the selected sets of the first camera and the second camera.

To perform the first to fourth methods described above, it is necessary that the image candidate points of pupils are detected by both of the left camera 2A and the right camera 2B. However, in the case where the pupil and glasses reflection overlap in the image taken by one camera, the pupil cannot be detected as the image candidate point in the image taken by that camera, and the above-described first to fourth methods cannot be appropriately performed in some cases. It is thus preferable to use three or more cameras. In the case of using three cameras, even when the image candidate points of pupils cannot be detected by the image that is taken by one of those cameras, the above-described first to fourth methods can be performed if the image candidate points of pupils are detected using the images that are taken by the other two cameras. It is thereby possible to conduct pupil detection more reliably.

Figure 16:
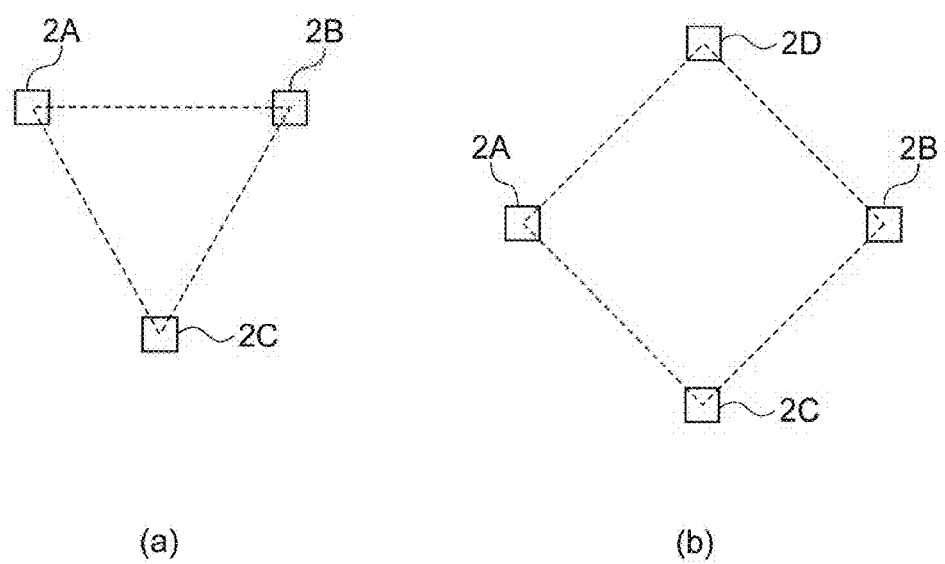
FIG. 16 is a view showing an example of arrangement of three or four cameras.

FIG. 16 shows an example of arrangement of three or more cameras. FIG. 16(a) shows an example of arrangement of three cameras 2A to 2C. The third camera 2C is preferably placed at the position away from the straight line connecting the first camera 2A and the second camera 2B. In the case of using the above-described first method or third method, it is difficult to exclude the case where images of two different points located on the plane including the axis being the straight line connecting the two cameras are taken by different cameras. For example, in the case where the first camera 2A and the second camera 2B are arranged in line along the horizontal direction, when the first camera 2A and the second camera 2B detect two different points distant from each other in the horizontal plane as image candidate points, it is difficult to exclude such a set of image candidate points. Thus, by placing the third camera 2C at the position away from the straight line connecting the first camera 2A and the second camera 2B, it becomes easy to exclude an inappropriate set of image candidate points. The three cameras 2A to 2C are preferably placed at the positions corresponding to the vertices of a regular triangle. Further, in consideration of the problem that glasses reflection and pupils overlap in the image, particularly, it is preferred that the three cameras 2A to 2C are placed at a distance of at least 10 degrees from each other when viewed from a subject.

FIG. 16(b) shows an example of arrangement of four cameras 2A to 2D. In the case of placing four cameras also, the third camera 2C and the fourth camera 2D are preferably placed at the positions away from the straight line connecting the first camera 2A and the second camera 2B. It is more preferred that the cameras 2A to 2D are placed at the positions corresponding to the vertices of a rectangle. Particularly, it is preferred that the cameras 2A to 2D are placed at the positions corresponding to the vertices of a square.

Note that, in this case, a pupil detection result is obtained for each set of two cameras. Then, one pupil detection result may be obtained by performing calculation to obtain an arithmetic average of coordinate values, for example, on the pupil detection result for each set of the cameras.

In the case of using three cameras as described above, the positions of a pair of pupils of a subject can be obtained more accurately in the following way. The three cameras are cameras 1 to 3. Among the three cameras, pairs of two cameras (camera pairs) are determined. Three camera pairs are thereby obtained. A pair of the camera 1 and the camera 2 is referred to as a camera pair 1-2, a pair of the camera 2 and the camera 3 is referred to as a camera pair 2-3, and a pair of the camera 3 and the camera 1 is referred to as a camera pair 3-1. Note that the number of cameras used is not limited to three, and it may be at least three. Further, the number of camera pairs is also not limited to three, and it may be at least three.

In this method, pupil pair candidates are determined for each camera pair. To be specific, for each of at least three camera pairs determined in advance, one of the camera pair is the first camera, the other one of the camera pair is the second camera, and a pair of pupils of a subject are determined as pupil pair candidates by the pupil detection method including the above-described first to ninth steps. To be more specific, space candidate points are acquired, the space candidate points where the angle θ (see Equation (20)) satisfies Equation (21) are left by the first method, and further, the three-dimensional coordinates of the space candidate points are calculated by the second method or the third method. Then, by the fourth method, a pair of two space candidate points where the distance between the two space candidate points is an inappropriate value as the human inter-pupil distance are determined not to be the pupil pair of the subject and thus excluded. A pair of space candidate points that remain without being excluded is left as a candidate for a pupil pair of the subject.

Figure 17:
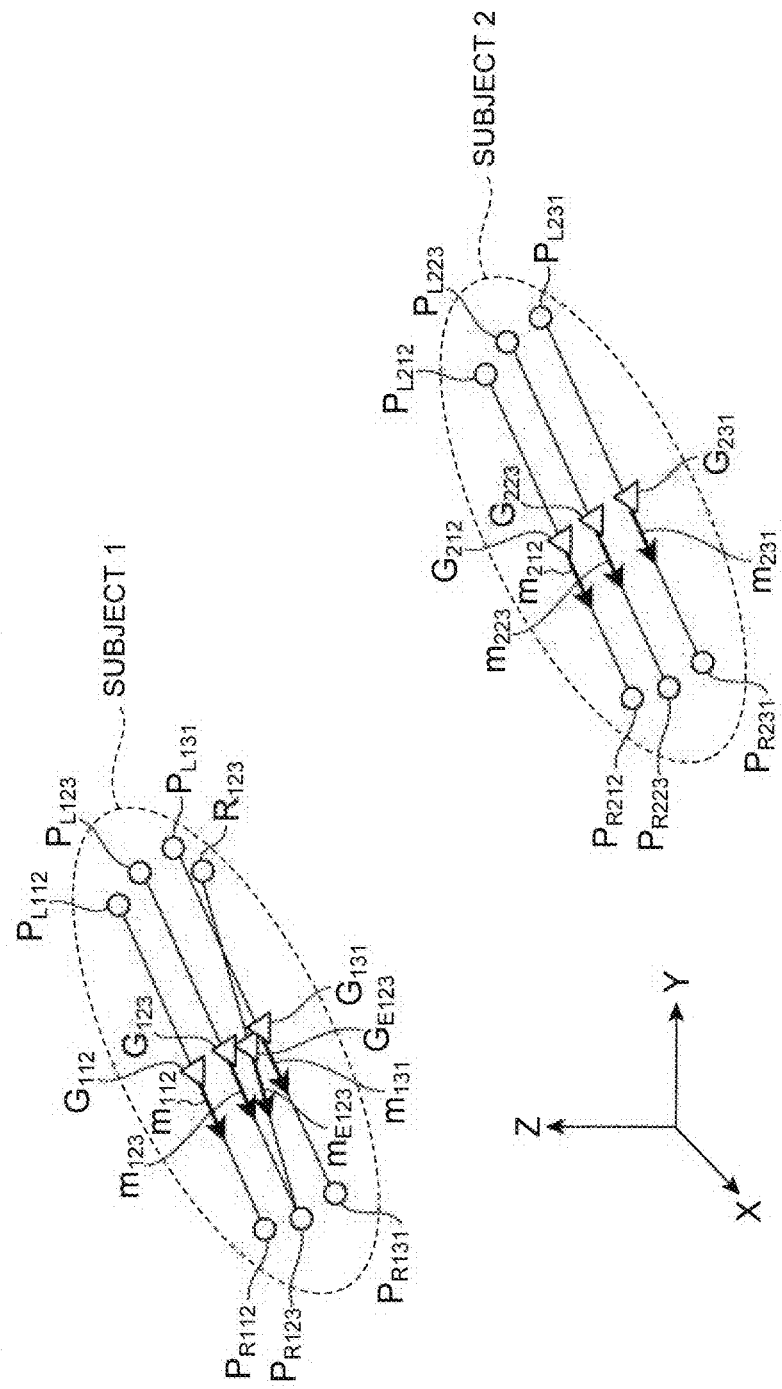
FIG. 17 is a view showing a detection result of a pair of pupils of two persons by three cameras.

As an example, when detecting pupil pairs of two subjects, a subject 1 and a subject 2, as shown in FIG. 17, it is assumed that a pupil candidate $P_{L112}$ of the left eye of the subject 1, a pupil candidate $P_{R112}$ of the right eye of the subject 1, a pupil candidate $P_{L212}$ of the left eye of the subject 2, and a pupil candidate $P_{R212}$ of the right eye of the subject 2 are obtained by the camera pair 1-2. Further, it is assumed that a first pupil candidate $P_{L123}$ of the left eye of the subject 1, a second pupil candidate $R_{123}$ of the left eye of the subject 1, a pupil candidate $P_{R123}$ of the right eye of the subject 1, a pupil candidate $P_{L223}$ of the left eye of the subject 2, and a pupil candidate $P_{R223}$ of the right eye of the subject 2 are obtained by the camera pair 2-3. Furthermore, it is assumed that a pupil candidate $P_{L131}$ of the left eye of the subject 1, a pupil candidate $P_{R131}$ of the right eye of the subject 1, a pupil candidate $P_{L231}$ of the left eye of the subject 2, and a pupil candidate $P_{R231}$ of the right eye of the subject 2 are obtained by the camera pair 3-1. Note that the second pupil candidate $R_{123}$ of the left eye of the subject 1 obtained by the camera pair 2-3 is actually a glasses reflection image of the subject 1 and different from the actual pupil of the subject 1. The other pupil candidates correspond to the actual pupils of the subject 1.

Next, for each of the pupil pair candidates determined above, the direction vector of the vector connecting both pupils (one and the other one of the pupil pair candidate) and the midpoint of both pupils are obtained. In FIG. 17, the direction vector of the vector connecting the pupil candidates $P_{L112}$ and $P_{R112}$ is $m_{112}$, and the midpoint is $G_{112}$. The direction vector of the vector connecting the pupil candidates $P_{L123}$ and $P_{R123}$ is $m_{123}$, and the midpoint is $G_{123}$. The direction vector of the vector connecting the pupil candidates $R_{123}$ and $P_{R123}$ is $m_{E123}$, and the midpoint is $G_{E123}$. The direction vector of the vector connecting the pupil candidates $P_{L131}$ and $P_{R131}$ is $m_{131}$, and the midpoint is $G_{131}$. The direction vector of the vector connecting the pupil candidates $P_{L212}$ and $P_{R212}$ is $m_{212}$, and the midpoint is $G_{212}$. The direction vector of the vector connecting the pupil candidates $P_{L223}$ and $P_{R223}$ is $m_{223}$, and the midpoint is $G_{223}$. The direction vector of the vector connecting the pupil candidates $P_{L231}$ and $P_{R231}$ is $m_{231}$, and the midpoint is $G_{231}$.

For the pupil pair of the same subject, the direction vectors respectively obtained by the three camera pairs form an angle of approximately 0 with one another. Further, the midpoints respectively obtained by the three camera pairs are in close proximity to one another. Using such characteristics, it is possible to determine which pupil pair candidate corresponds to the pupils of which subject for pupil pairs of a plurality of subjects, and it is possible to obtain a correct pupil pair by eliminating misdetected pupil candidates. In other words, when the direction of the direction vector obtained for a pupil pair candidate determined by one camera pair forms an angle of a threshold or more with the direction of the direction vector obtained for pupil pair candidates determined by the other plurality of camera pairs, the pupil pair candidate determined by one camera pair is deleted.

In the example of FIG. 17, the midpoints $G_{112}$, $G_{123}$, $G_{131}$ and $G_{E123}$ are in close proximity to one another. The midpoints $G_{212}$, $G_{223}$ and $G_{231}$ are in close proximity to one another and distant from the midpoints $G_{112}$, $G_{123}$, $G_{123}$, $G_{131}$ and $G_{E123}$. Based on this fact, it can be determined that the midpoints $G_{112}$, $G_{123}$, $G_{131}$ and $G_{E123}$ are the midpoints of pairs of pupil candidates of one subject (the subject 1), and the midpoints $G_{212}$, $G_{223}$ and $G_{231}$ are the midpoints of pairs of pupil candidates of the other subject (the subject 2).

Further, the direction vector $m_{E123}$ forms a large angle with the direction vectors $m_{112}$, $m_{123}$ and $m_{131}$. It is thereby possible to determine that the pupil candidate $R_{123}$ that is used for obtaining the direction vector $m_{E123}$ does not correspond to the true pupil of the subject.

Based on such characteristics, it is possible to more correctly estimate the positions of pupils by calculating the average of the coordinates of the pupil pair candidates remaining without being deleted due to the direction of the direction vector and determining the average as the final positions of pupils. To be specific, in the case of using three cameras, it is possible to correctly estimate the positions of pupils by selecting two camera pairs where their midpoints are in closer proximity and the angle between their direction vectors is small, calculating the average of the coordinates of the pupil candidates obtained based on the two cameras included in the selected camera pairs, and determining the average as the final positions of pupils. After correctly estimating the positions of pupils in this manner, windows for limiting target regions to search for pupils at the time of pupil tracking may be given by projecting the estimated positions of pupils onto the camera image.

Note that the pupil positions detected by different camera pairs are not the same in FIG. 17 because of errors in camera calibration (stereo calibration). However, in many cases, the directions of the lines connecting the pupil candidates obtained by different camera pairs (which are the directions of the direction vectors) are substantially parallel if the pupil candidates correspond to the actual pupils. On the other hand, in the case where a glasses reflection image is misdetected as a pupil candidate, the direction of the line connecting the pupil pair including the glasses reflection (which is the direction of the direction vector) is not parallel.

Further, there is a case where, when there are three cameras, a glasses reflection image overlaps with a pupil image in one of the three cameras, and the pupil cannot be thereby detected. In this case, a pupil pair can be obtained only in one camera pair composed of two cameras excluding the above one camera. Thus, only one pupil pair can be obtained, and it is not possible to use the above-described method of selecting a correct pupil pair by using the midpoints of the pupil pairs and the direction vectors connecting the pupil pairs obtained by the three camera pairs. Therefore, in the case of assuming that a glasses reflection image and a pupil image overlap in one camera, the number of cameras is preferably at least four. In the case where only one pupil pair candidate is obtained using the above method (specifically, the method of extracting a pupil pair candidate using the inter-pupil distance, the direction of the direction vector between pupils, and the midpoint between pupils) in the system with only three cameras, the pupil pair candidate is likely to be the true pupil pair of the subject. Thus, when only one pupil pair candidate is obtained, the pupil pair candidate may be trusted as the true pupil pair. However, in the case where misdetection that detects a point which is not the true pupil (for example, a glasses reflection image) as a pupil candidate point occurs in either camera of one camera pair among the three cameras, two sets of pupil pair candidates, which are a pupil pair candidate including the pupil candidate point that is not the true pupil and a pupil pair candidate including the pupil candidate point that is the true pupil, are detected, and it is not possible to determine which of the two sets of pupil pair candidates is the true pupil pair. Thus, both of the two sets of pupil pair candidates are excluded, and no pupil pair can be detected as a result. Thus, the detection rate decreases while misdetection is avoidable. This is the same for the case of two cameras.

Note that, in FIG. 17, at the time when space candidate points are merely extracted as pupil candidate points, it is not possible in practice to distinguish that a certain pupil candidate point is the pupil of the subject 1 or the pupil of the subject 2, and that a pair of two pupil candidate points are the pupil pair of the subject 1 or the pupil pair of the subject 2. Therefore, a pair of the pupil candidate $P_{L112}$ and the pupil candidate $P_{R212}$ and a pair of the pupil candidate $P_{R123}$ and the pupil candidate $P_{L223}$, for example, are also detected as pupil pair candidates. For those pupil pair candidates, the one where the distance between pupil candidates is not an appropriate value as the inter-pupil distance can be excluded by using the fourth method. Further, the pupil pair candidate that cannot be the true pupil pair can be excluded in the following way.

Specifically, the distance between pupil candidate points is calculated on a round-robin system among the pupil candidate points remaining after the process up to the previous step is done. Then, the pupil candidate points whose calculated distance is a specified threshold or less are grouped into one group. Although the specified threshold can be set arbitrarily according to the accuracy of stereo calibration by each camera pair, it needs to be a smaller value than the value that can be the human inter-pupil distance. The specified threshold may be 4.5 cm, for example. By such grouping, the pupil candidate points are divided into four groups, which are a candidate point for the right pupil of the subject 1, a candidate point for the left pupil of the subject 1, a candidate point for the right pupil of the subject 2, and a candidate point for the left pupil of the subject 2, in the example of FIG. 17. There is a case where a candidate point based on misdetection of a glasses reflection image or the like cannot be deleted as a result of the process up to the previous step, and the candidate point based on misdetection is included in any group. In this case, the candidate point based on misdetection is excluded to detect a pupil pair by the above-described method using the inter-pupil distance and the direction vector between pupils (the midpoint between pupils may be used in addition). However, by performing the grouping first, it is possible to significantly reduce the number of pupil pair candidates for which the distance between candidate points, the direction vector between candidate points and the midpoint between candidate points are calculated in the method of using the inter-pupil distance and the direction vector between pupils. Further, in the case where there are three or more cameras and stereo calibration of each camera is done correctly, it is possible to minimize the misdetection of glasses reflection in the process up to the previous step. Therefore, it is possible to independently detect one pupil, not a pupil pair, by the grouping.

(Pupil Tracking Method)

A pupil tracking method for tracking pupils after detecting the positions of a pair of pupils of a subject by the above-described pupil detection method is described hereinafter.

Under the constraint that the three-dimensional inter-pupil distance of both eyes of a subject is constant, the following method is used to track two pupils as one lump. It is assumed that the three-dimensional inter-pupil distance is l, which is known. Actually, however, once the pupil detection process is done and the three-dimensional coordinates of both pupils are detected, l can be determined based on the detected three-dimensional coordinates of pupils. In the following pupil tracking process, the value of l determined in this manner is used.

Figure 18:
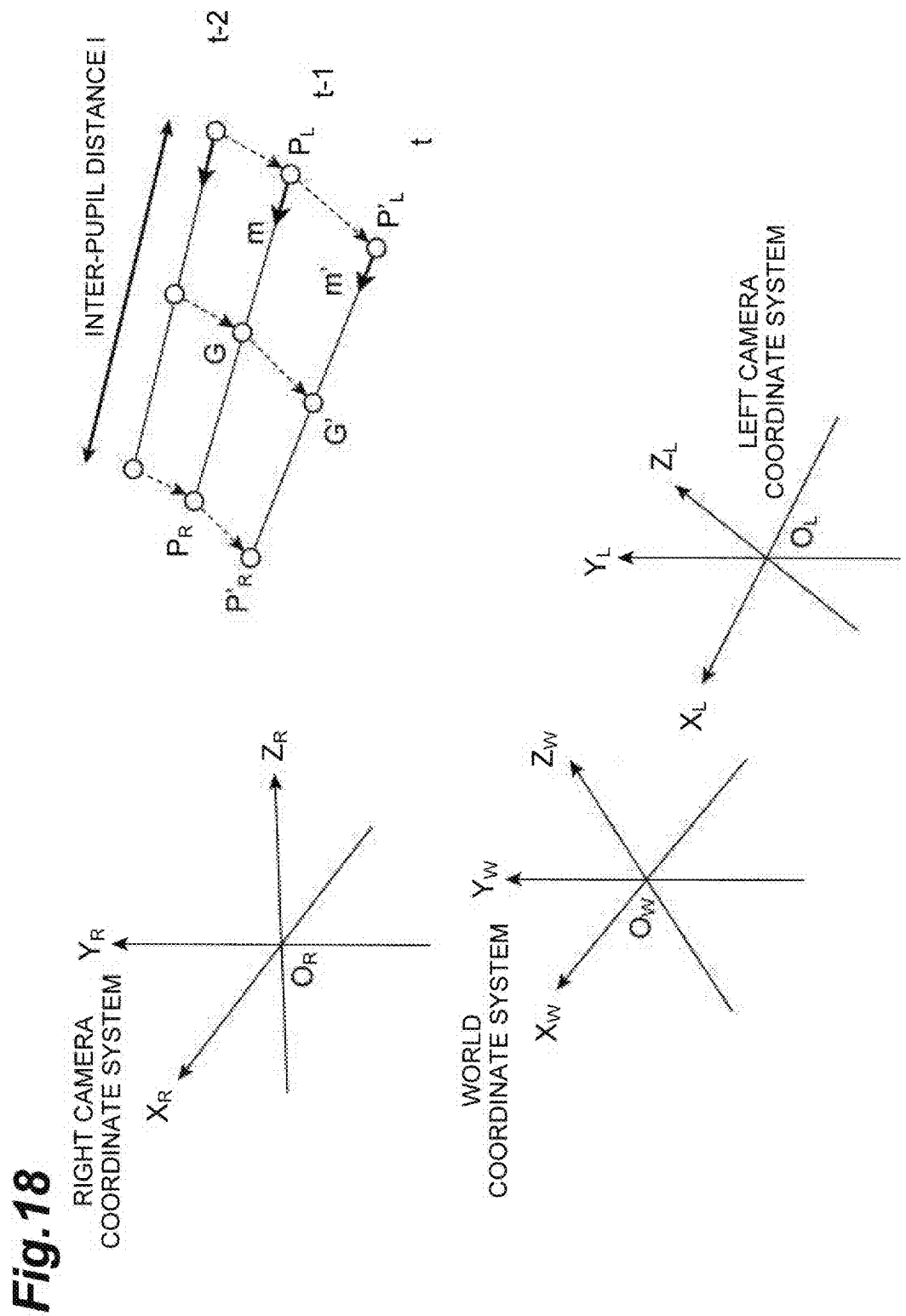
FIG. 18 is a view showing a pupil tracking method based on an inter-pupil distance according to this embodiment.

FIG. 18 shows the state where two pupils are moving as a user's head is moving in the situation where a plurality of cameras after camera calibration are placed. The three-dimensional coordinates of the left pupil $P_L$ and the right pupil $P_R$ are generally obtained by stereo matching using two or more cameras after camera calibration, and the following pupil tracking process is performed based on the obtained three-dimensional coordinates of the left pupil $P_L$ and the right pupil $P_R$. FIG. 18 shows only two cameras, which are the left camera and the right camera, and shows the left camera coordinate system with the origin point $O_L$ and the right camera coordinate system with the origin point $O_R$. Note that, however, even when the pupils cannot be detected by one camera, because the three-dimensional coordinates of both pupils can be estimated by a method different from stereo matching as described later, it is possible to perform the same pupil tracking process based on the estimated three-dimensional coordinates of the left pupil $P_L$ and the right pupil $P_R$ in such a case as well.

When the left pupil three-dimensional position, the right pupil three-dimensional position and those gravity center positions which are determined in the previous frame (t-1) to the current frame (t) are $P_L$, $P_R$ and G respectively, and the unit vector from $P_L$ to G is m, the center of gravity G of both pupils and the inter-pupil unit direction vector m are represented by the following Equations (45) and (46).

[Math45]
$$G = \frac{P_L + P_R}{2} \tag{45}$$

[Math46]
$$m = \frac{P_R - P_L}{\|P_R - P_L\|} \tag{46}$$

From the center of gravity G of both pupils, the inter-pupil unit direction vector m and the inter-pupil distance l, the absolute position and the relative position of the pupil pair are determined. The center of gravity G of both pupils and the inter-pupil unit direction vector m are composed of three elements, respectively (($G_x, G_y, G_z$) and ($m_x, m_y, m_z$)). For each of those six elements, the prediction model represented by the following Equations (47) and (48) is applied. It is assumed in this example that each element changes at a certain speed.

[Math47]
$$w[t] = w[t-1] + w'[t] \cdot \Delta T \tag{47}$$

[Math48]
$$w'[t] = \frac{w[t-1] - w[t-2]}{\Delta T} \tag{48}$$

$\Delta T$ indicates time between frames, t indicates time of the current frame, t-1 indicates the previous frame, and t-2 indicates the second previous frame.

Note that the Kalman filter may be used as the prediction model. Assuming the case where there is missing of an image or an image is acquired irregularly, the following method is effective. When the time (actual time) of the second previous frame and the previous frame is $t_{-2}$ and $t_{-1}$ and the time of the current frame is $t_0$, the following Equation is established if it is assumed that each element changes at a certain speed.

[Math49]
$$\frac{w(t_0) - w(t_{-1})}{t_0 - t_{-1}} = \frac{w(t_{-1}) - w(t_{-2})}{t_{-1} - t_{-2}} \tag{49}$$

$w(t_{-2})$, $w(t_{-1})$ and $w(t_0)$ are the values of each element at each time. The value of each element at the current time is given by the following Equation (50) by transforming the Equation (49).

[Math50]
$$w(t_0) = \{w(t_{-1}) - w(t_{-2})\}\frac{t_0 - t_{-1}}{t_{-1} - t_{-2}} + w(t_{-1}) \tag{50}$$

More strictly, for the unit direction vector m, it is more appropriate to assume that m rotates in a certain direction at a certain speed, rather than assuming that each element independently changes at a certain speed. Specifically, it is assumed that the unit direction vectors m of the second previous frame and the previous frame, which are $m(t_{-2})$ and $m(t_{-1})$ respectively, rotate on the same plane. The angle $\xi$ between $m(t_{-2})$ and $m(t_{-1})$ is given from the inner product of $m(t_{-2})$ and $m(t_{-1})$. The sign of the angle $\xi$, which is the direction of rotation of m, is given from the sign of the Z coordinate of the outer product of $m(t_{-2})$ and $m(t_{-1})$ in the orthogonal coordinate system where the plane including both of $m(t_{-2})$ and $m(t_{-1})$ is the X-Y plane. Thus, $m(t_0)$, which is m of the current frame, can be obtained by the condition (the following Equation (51)) that the rotation angular velocity $\omega(t_{-1})$ from $m(t_{-2})$ to $m(t_{-1})$ matches the rotation angular velocity $\omega(t_0)$ from $m(t_{-1})$ to $m(t_0)$, assuming uniform rotation of m.

[Math51]
$$\frac{\omega(t_0)}{t_0 - t_{-1}} = \frac{\omega(t_{-1})}{t_{-1} - t_{-2}} \tag{51}$$

By Equations (47) and (48), based on G and the vector m of the second previous frame and the previous frame, the center of gravity G of both pupils and the inter-pupil unit direction vector m of the current frame are predicated (which are G' and m', respectively). For the predication of the center of gravity G of both pupils and the inter-pupil unit direction vector m, Equations (49) and (50) may be used or Equations (51) may be used instead of Equations (47) and (48). Further, using the predicted center of gravity G' of both pupils and the inter-pupil unit direction vector m', the three-dimensional coordinates $P'_L$ and $P'_R$ of the left and right pupils in the current frame are obtained by the following Equations (52) and (53).

[Math52]

$$P'_L = G' - \frac{l}{2}m' \quad (52)$$

[Math53]

$$P'_R = G' + \frac{l}{2}m' \quad (53)$$

Assuming that the three-dimensional coordinates of pupils are obtained also in the previous frame by the same method as above, points where the coordinates are projected onto each camera image plane correspond to the pupils in the image. Specifically, by projecting the obtained three-dimensional coordinates of pupils onto the camera image plane, the image coordinates of pupils can be obtained. Using the image coordinates, the image of the pupil part in the previous frame (the image in the small window) is shifted to the predicted position in the current frame and then subtraction is carried out.

Note that, however, the inter-pupil distance l given by Equations (52) and (53) is not constant in practice, and the inter-pupil distance l can vary slightly if the accuracy of camera calibration is low. Therefore, the prediction model of Equations (47) and (48) may be used also for l, and Equations (54) and (55) may be given by predicting l' from the inter-pupil distance of the previous frame. Note that, for predication of the inter-pupil distance l also, the prediction model of Equations (49) and (50) may be used or the prediction model of Equation (51) may be used instead of the prediction model of Equations (47) and (48).

[Math54]

$$P'_L = G' - \frac{l'}{2}m' \quad (54)$$

[Math55]

$$P'_R = G' + \frac{l'}{2}m' \quad (55)$$

Further, because it is difficult to deal with rapid translational motion or speed up or slow down of rotation of a head in the prediction model of Equations (47) and (48), it is preferred to perform the subtraction position correction method using the amount of movement of corneal reflection disclosed in Patent Literature 8. In the case of using the prediction model by Equations (49) and (50) or the prediction model by Equation (51) as well, it is preferred to perform the subtraction position correction method using the amount of movement of corneal reflection disclosed in Patent Literature 8. Note that, however, because corneal reflection does not always exist depending on the angle of the line of sight, when there is no corneal reflection, subtraction position correction is performed as it is using the subtraction position correction method using the inter-pupil distance described above. After the two-dimensional coordinates of pupils are obtained in the image of each camera, the three-dimensional coordinates of pupils in the current frame are obtained by stereo matching, and then the same processing is repeated after that.

Although the corneal reflection detection method is described earlier with reference to FIG. 15, another method of detecting corneal reflection is described hereinbelow. In any case of FIGS. 15(a) to 15(d), if the three-dimensional coordinates of corneal reflection obtained from both of two cameras are the three-dimensional coordinates of actual corneal reflection, the distance between two (left and right) corneal reflections of a subject is a value that is substantially constant at all times, just like the distance between two pupils. Thus, corneal reflection can be detected also using the same technique as the pupil detection method according to this embodiment.

A specific procedure is as follows. First, facial images of a subject are taken by the left and right cameras, and the images are thereby acquired. Next, image corneal reflection candidate points that serve as candidates for corneal reflection of the subject are extracted from the acquired image. In general, because the corneal reflection cannot be detected when the pupils cannot be detected due to eyes being closed or the like, it is effective to extract corneal reflection candidate points from small windows (small regions) having the detected pupils at the center. Then, one image corneal reflection candidate point is selected from each of the images acquired by the left and right cameras and paired with each other, and the above-described method of extracting space candidate points and the method of selecting space candidate points based on the distance between two points are applied to this pair, thereby calculating the three-dimensional coordinates of the left and right corneal reflections of the subject.

Then, based on the calculated position of the calculated three-dimensional coordinates of the corneal reflection, assuming that the pupil exists within a range of several mm from the corneal reflection, a small window (small region) is set in the region within the image corresponding to the range of several mm from the center of the corneal sphere. Then, subtraction processing is performed in this small window, thereby determining the position of the pupil and calculating the image coordinates of the pupil.

Further, by conducting subtraction position correction by the corneal reflection, the robustness and the position detection accuracy of pupil detection can be maintained even when the head has moved. Because the robustness and the position detection accuracy of corneal reflection detection can be enhanced by detecting the corneal reflection based on the condition that the distance between corneal reflections is constant as described above, it is possible to increase the robustness and the position detection accuracy of pupil detection both when detecting pupils from the whole image and when detecting pupils after subtraction position correction using the amount of movement of corneal reflections.

Further, regarding a pupil pair detected under the condition that the distance between pupils is constant, when glasses reflection exists in close proximity to one pupil, for example, two pupil pairs are obtained in some cases (for example, one is a pupil pair including the true pupil of the left eye and the true pupil of the right eye and the other is a pair including the true pupil of the left eye and the glasses reflection near the right eye). In such a case, small windows are applied to the pupil candidate points in the image that form the both pupil pairs, and corneal reflection pairs are obtained therein. A plurality of corneal reflection pairs are obtained in some cases. In such a case, it is determined which of pairs of the obtained pupil pair candidates and corneal reflection pair candidates are closest in three-dimensional distance. For each of the left eye and the right eye, the pupil included in the determined pupil pair candidate, and the corneal reflection included in the determined corneal reflection pair candidate, are determined as the true pupil and the true corneal reflection.

As described above, by combining the pupil detection where the inter-pupil distance is constant and the corneal reflection detection where the inter-corneal reflection distance is constant, it is possible to increase the robustness and the position detection accuracy of both of the pupil detection and the corneal reflection detection.

Next, a method for estimating the three-dimensional coordinates of pupils in the next frame is described for each case where the left and right pupils are detected or not detected by each camera based on the pupil detection result.

Figure 19:
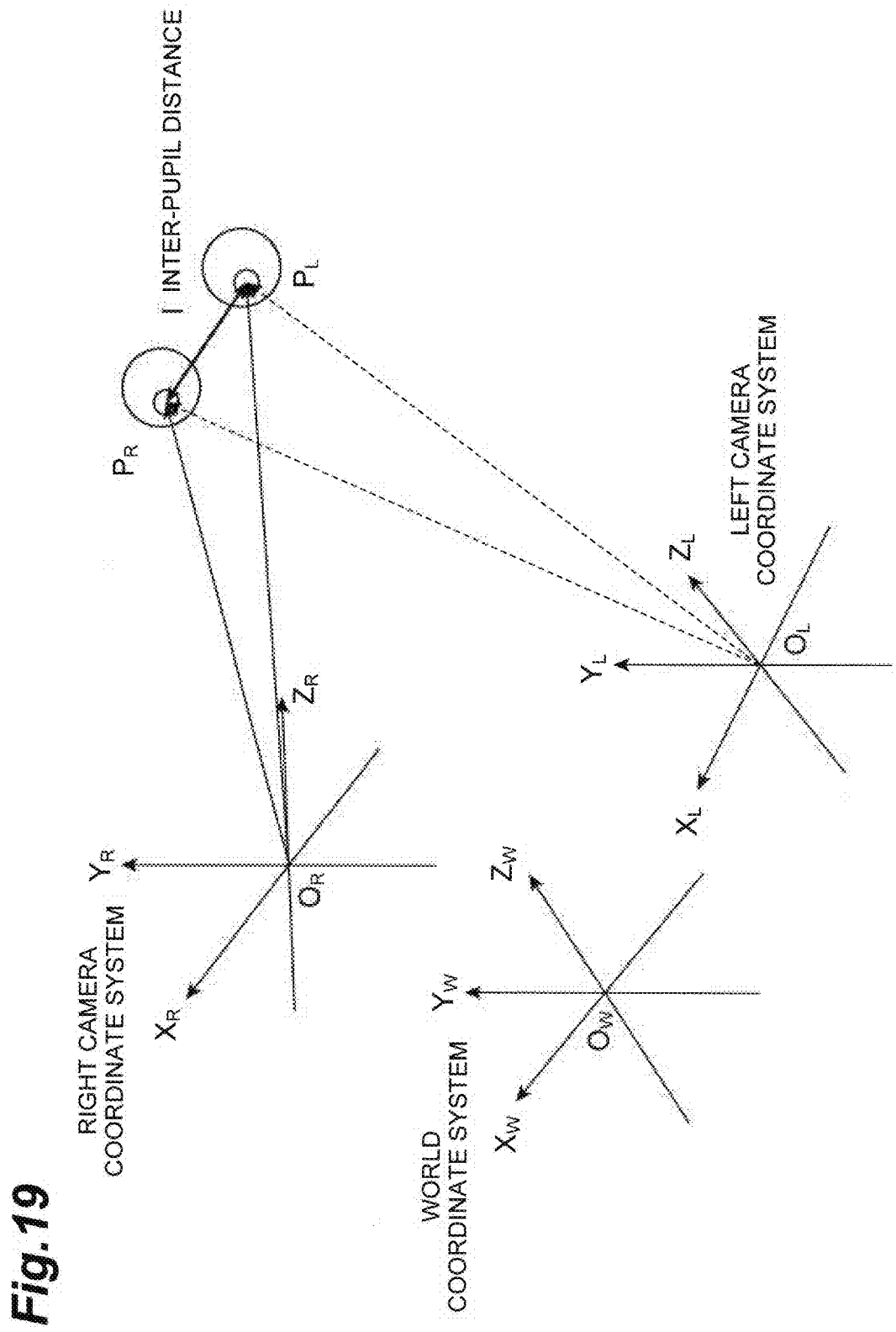
FIG. 19 is a view showing a pupil tracking method when both pupils are detected by both cameras.

First, the case where both of the two pupils are detected by two or more cameras is described. Assume that there are two cameras $O_L$ and $O_R$ on which camera calibration has been performed as shown in FIG. 19. The case where both of the two pupils, the left pupil $P_L$ and the right pupil $P_R$, are detected by both of the two cameras is considered in this example.

In this case, the method described earlier is used. In the past two frames, the three-dimensional coordinates of the pupils in the current frame are estimated using Equations (45) to (53) from the center of gravity G of both pupils and the inter-pupil unit direction vector m that have already been obtained. Based on this, the pupil position of each pupil in the image of the current frame is estimated by each camera. The two-dimensional positions of the two pupils are calculated by shifting the image near the already-calculated pupil position (within the small window) in the previous frame to the estimated pupil position in the current frame and performing subtraction.

After that, the pupils in the image are detected, and the three-dimensional positions of the pupils are calculated. Further, the center of gravity G of both pupils and the inter-pupil unit direction vector m are obtained from the results, and the three-dimensional positions of the left and right pupils are calculated again by Equations (52) and (53) or Equations (54) and (55). Those information are used in the next frame as the three-dimensional positions of the left and right pupils, the center of gravity G of both pupils and the inter-pupil unit direction vector m in the previous frame. In this manner, in the case where the two pupils are detected by both of the two cameras, the positional information of the both pupils are treated equally.

Figure 20:
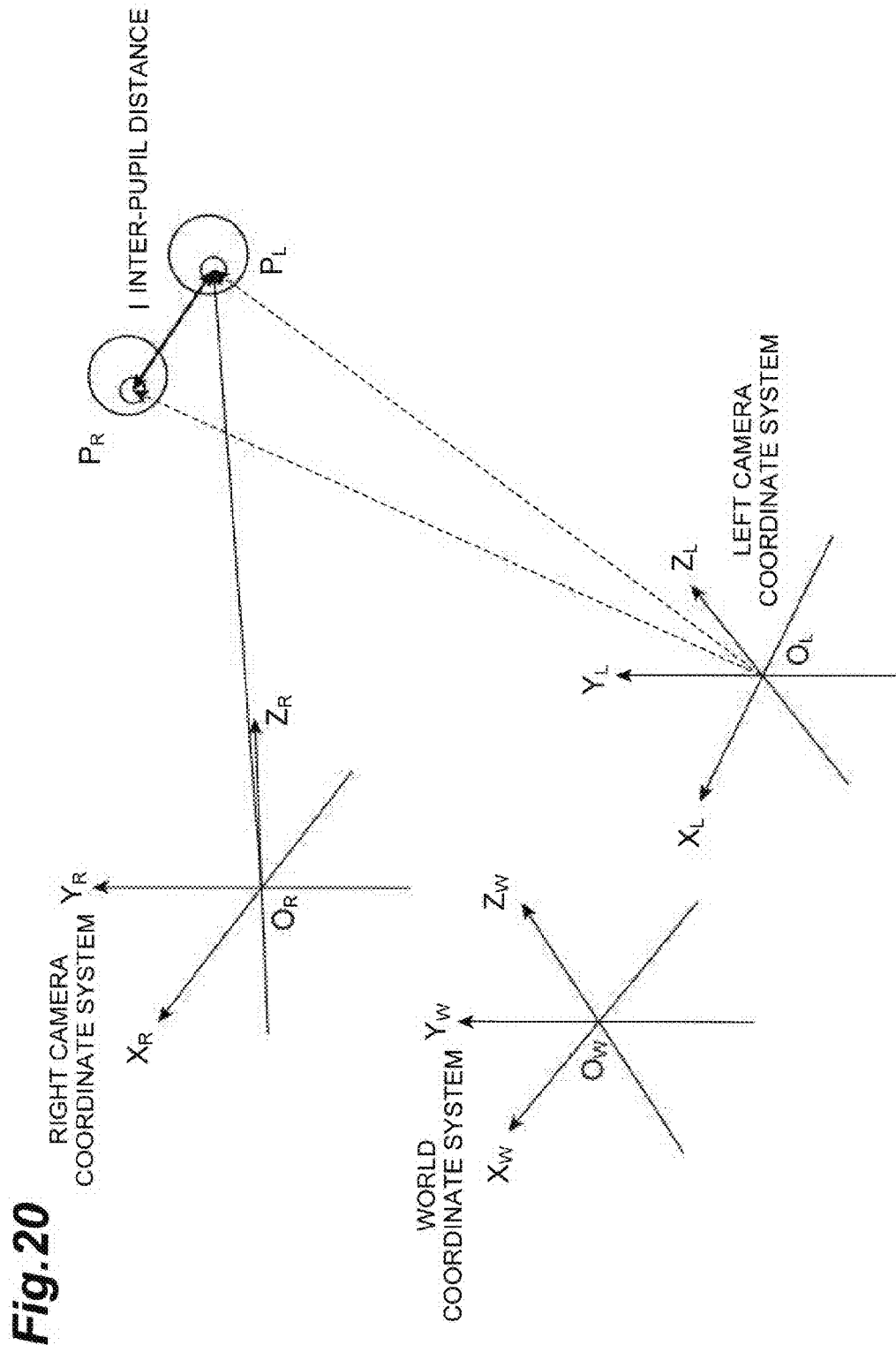
FIG. 20 is a view showing a pupil tracking method when only one pupil is detected by one camera.

Next, the case where one of the two pupils is detected by two or more cameras and the other one is detected only by one camera is described. In this example, the case where, as a result of performing pupil detection by subtraction position correction after estimating the three-dimensional positions of the left and right pupils in the current frame as stated above in the description of the case where the two pupils are detected by two or more cameras, the both pupils are detected by one camera and one pupil is detected by the other camera as shown in FIG. 20 is described. In the example of FIG. 20, the case where both of the left pupil $P_L$ and the right pupil $P_R$ are detected by the left camera $O_L$, and only the left pupil $P_L$ is detected by the right camera $O_R$ is shown.

In this case, because the left pupil $P_L$ is detected by both cameras, the three-dimensional position of the left pupil $P_L$ is calculated by stereo matching, assuming that a specific image on the right camera image and a specific image on the left camera image are $P_L$. On the other hand, because the right pupil $P_R$ is not detected by the right camera $O_R$, the three-dimensional position of $P_R$ is unknown. Note that, however, because the right pupil $P_R$ is detected by the left camera $O_L$, the right pupil $P_R$ exists on the line $O_L P_R$. Thus, the three-dimensional position of $P_R$ is calculated from the condition that the right pupil $P_R$ exists on the line $O_L P_R$ and the condition that the length of the line $P_L P_R$ is equal to the three-dimensional distance l between the pupils.

Figure 21:
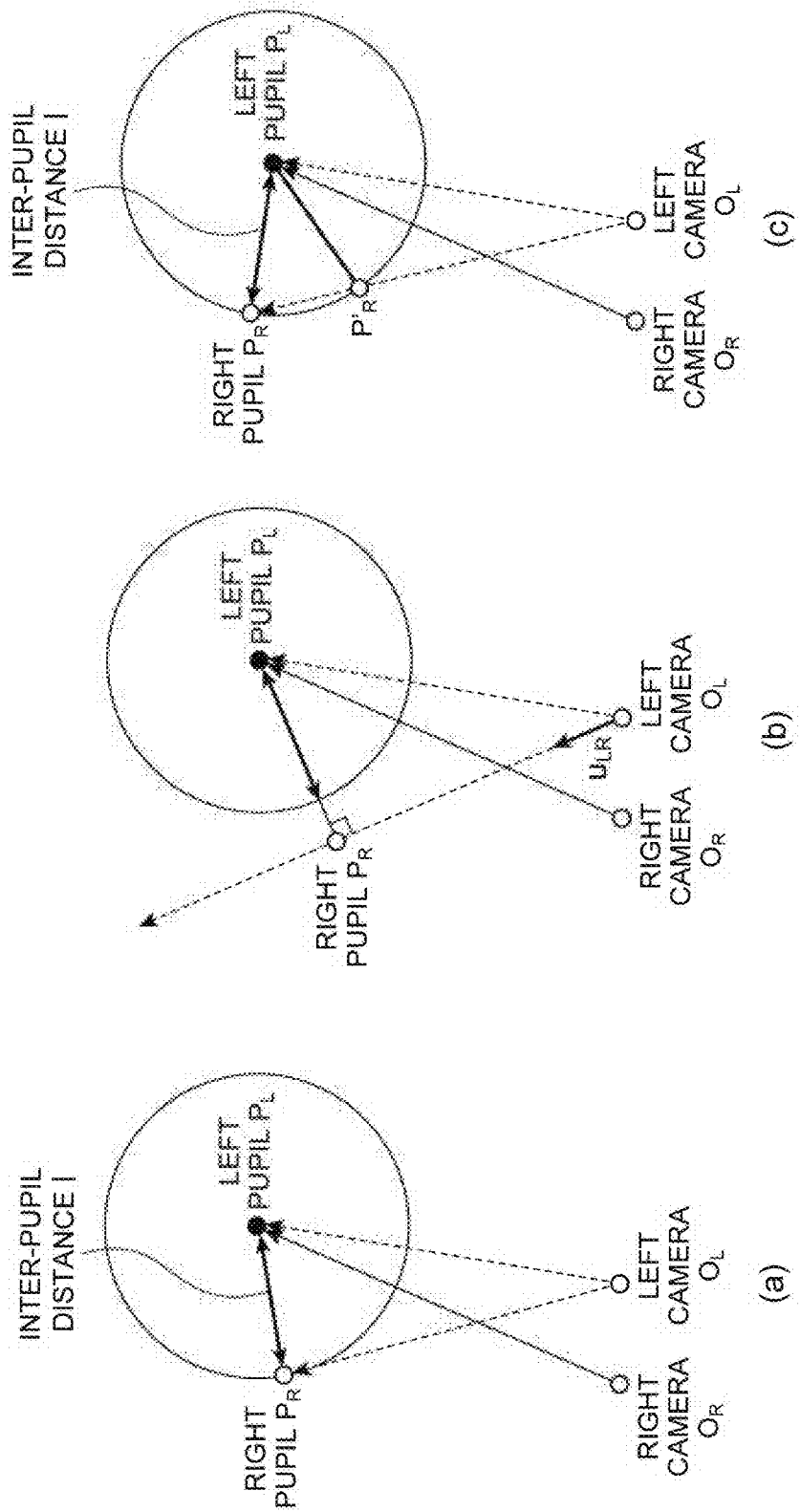
FIG. 21 is a view showing a pupil tracking method when only one pupil is detected by one camera.

Specifically, as shown in FIG. 21, it is assumed that $P_R$ exists on a sphere centering on $P_L$ with a radius l. A method of calculating $P_R$ is specifically described hereinbelow. When the three-dimensional position of $P_L$ in the world coordinate system is $(P_x, P_y, P_z)$, the equation of the sphere centering on $P_L$ with the radius l is represented by the following Equation (56).

[Math56]

$$(x-P_x)^2 + (y-P_y)^2 + (z-P_z)^2 = l^2 \tag{56}$$

Further, the equation of the straight line $O_L P_R$ connecting the camera $O_L(x_0, y_0, z_0)$ and the right pupil $P_R$ in the world coordinate system is given by the following Equation (57) by using the unit direction vector $u_{LR}(u_x, u_y, u_z)$ from $O_L$ to $P_R$.

[Math57]

$$\frac{x - x_0}{u_x} = \frac{y - y_0}{u_y} = \frac{z - z_0}{u_z} \tag{57}$$

Setting the value of Equation (57) as a parameter t and representing the values of x, y and z using the parameter t, the following Equation (58) is given.

[Math58]

$$\begin{cases} x = x_0 + u_x t \\ y = y_0 + u_y t \\ z = z_0 + u_z t \end{cases} \tag{58}$$

Substitution of Equation (58) into Equation (56) gives the following Equation (59).

[Math59]

$$(u_x^2 + u_y^2 + u_z^2)t^2 + 2\{u_x(x_0 - P_x) + u_y(y_0 - P_y) + u_z(z_0 - P_z)\}t + \tag{59}$$
$$(x_0 - P_x)^2 + (y_0 - P_y)^2 + (z_0 - P_z)^2 - l^2 = 0$$

Solving Equation (59) for t, there are following three cases depending on the solution of t. The first case is when the solution of Equation (59) is one, which is when Equation (59) has a multiple solution. The second case is when the solution of Equation (59) is two conjugate complex numbers. The third case is when the solution of Equation (59) is two different real numbers.

In the first case, which is when Equation (59) has a multiple solution, the intersection point between the sphere centering on the left pupil $P_L$ with the radius 1 and the line $O_L P_R$ is one as shown in FIG. 21(a), and t obtained as the multiple solution by Equation (59) is substituted into Equation (58) to obtain the three-dimensional coordinates of $P_R$. The obtained $P_R$, the already obtained $P_L$, and G and the vector m obtained from those are thereby acquired and used for the next frame.

In the second case, which is when the solution of Equation (59) is conjugate complex numbers (FIG. 21(b)), there is no intersection point between the sphere centering on the left pupil $P_L$ with the radius 1 and the line $O_L P_R$. Thus, the closest proximity point to $P_L$ on the line $O_L P_R$ is obtained as $P_R$.

When $P_R$ is an arbitrary point on the line $O_L P_R$, the vector $\overrightarrow{P_L P_R}$ is given by Equation (60), which is the linear expression for t, from Equation (58).

[Math60]
$$\overrightarrow{P_L P_R} = ((x_0 + u_x t) - P_x, (y_0 + u_y t) - P_y, (z_0 + u_z t) - P_z) \quad (60)$$

The distance between the line $O_L P_R$ and $P_L$ is the shortest when $\overrightarrow{P_L P_R}$ and the straight direction vector $u_{LR}$ are orthogonal to each other, and the inner product between the vector $\overrightarrow{P_L P_R}$ and the vector $u_{LR}$ is 0 as in the following Equation (61).

[Math61]
$$\overrightarrow{P_L P_R} \cdot \overrightarrow{u_{LR}} = \quad (61)$$
$$u_x\{(x_0 + u_x t) - P_x\} + u_y\{(y_0 + u_y t) - P_y\} + u_z\{(z_0 + u_z t) - P_z\} = 0$$

Solving Equation (61) for t, t is obtained as the following Equation (62).

[Math62]
$$t = \frac{u_x(P_x - x_0) + u_y(P_y - y_0) + u_z(P_z - z_0)}{u_x^2 + u_y^2 + u_z^2} \quad (62)$$

The obtained t is substituted into Equation (58) to obtain the three-dimensional coordinates of $P_R$. Further, when the obtained t is substituted into Equation (60), the distance between the two pupils is obtained by the length $|\overrightarrow{P_L P_R}|$ of the vector $\overrightarrow{P_L P_R}$. In this manner, when the solution of Equation (59) is conjugate complex numbers, the inter-pupil distance $|\overrightarrow{P_L P_R}|$ is the following Equation (63).

[Math63]
$$|\overrightarrow{P_L P_R}| > l \quad (63)$$

Thus, appropriate restriction is imposed as in the following Equation (64).

[Math64]
$$l_{max} > |\overrightarrow{P_L P_R}| \quad (64)$$

By imposing the restriction that the distance between the right pupil candidate and the left pupil is a specified threshold or less as in Equation (64), when the right pupil candidate image obtained from the image is a false pupil, it is prevented from being misdetected as a true pupil. Note that $l_{max}$ is the maximum inter-pupil distance, which is set in advance.

Just like the case where Equation (59) has a multiple solution, the obtained $P_R$, the already obtained $P_L$, and G and the vector m obtained from those are acquired and used for the next frame. Note that, in the case where the solution of Equation (59) is conjugate complex numbers, the distance between the obtained left pupil $P_L$ and right pupil $P_R$ is a value different from the inter-pupil distance 1 obtained in advance. To correct this, after G and m are obtained, the left pupil $P_L$ and the right pupil $P_R$ are calculated again using Equations (52) and (53) or Equations (54) and (55) and used for the next frame.

In the third case, which is when the solution of Equation (59) is two different real numbers, by substituting t obtained by Equation (59) into Equation (58), two three-dimensional coordinates are obtained as candidates for $P_R$ ($P_R$ and $P_R'$ in FIG. 21(c)). It is thus necessary to estimate which of the two obtained candidates is the true right pupil. In order to determine which of the two candidates is the right pupil position, it is determined which of the obtained candidates is closer to the three-dimensional position of $P_R$ in the current frame that is predicted by Equations (52) and (53) (or Equations (54) and (52)), and the one of the two candidates that is closer to the position of $P_R$ in the current frame is determined as the true pupil position.

After that, just like the case where Equation (59) has a multiple solution or a complex conjugate solution, the obtained $P_R$, the already obtained $P_L$, and G and the vector m obtained from those are acquired and used for the next frame.

Note that, calculation may be performed by assuming that the right pupil $P_R$ is on the sphere centering on the left pupil $P_L$ with the radius $l_{min}$, instead of the method of assuming that the right pupil $P_R$ is on the sphere centering on the left pupil $P_L$ with the radius l. $l_{min}$ is the minimum possible value as the inter-pupil distance, which is smaller than the predetermined inter-pupil distance l, and it is preferably 75% of the inter-pupil distance measured initially, for example. Note that, because the inter-pupil distance becomes shorter when looking at a nearby object, for example, due to convergence eye movement, a certain allowable range is required for the inter-pupil distance.

Figure 22:
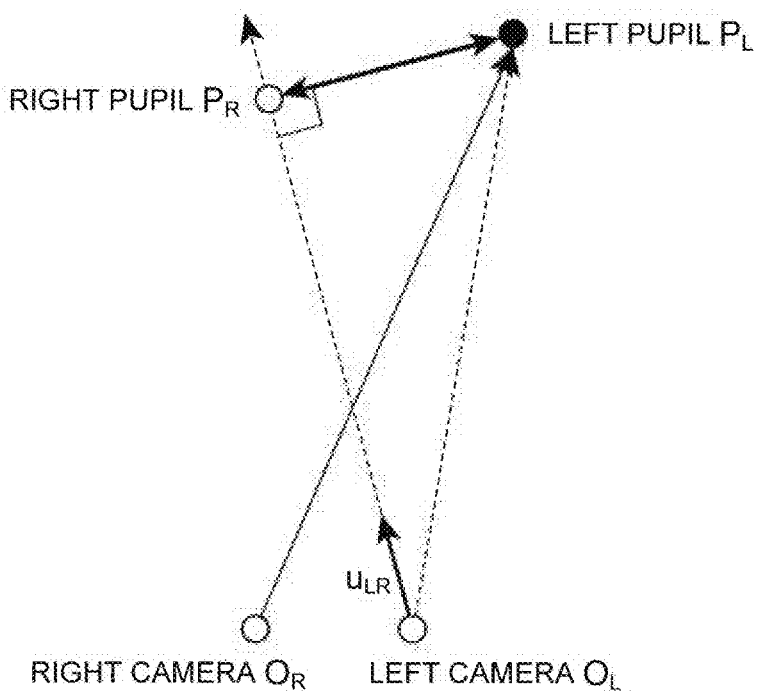
FIG. 22 is a view showing a pupil tracking method when only one pupil is detected by one camera.

In this method, when the right pupil $P_R$ is detected correctly, the distance l between the right pupil $P_R$ and the left pupil $P_L$ is longer than $l_{min}$, and therefore the line $O_L P_R$ and the sphere centering on the left pupil $P_L$ with the radius $l_{min}$ do not have an intersection point. Therefore, the quadratic equation for t where l of Equation (59) is substituted with $l_{min}$ has a complex conjugate solution. Thus, just like the above-described second case, which is when Equation (59) has a complex conjugate solution, the intersection point when dropping a perpendicular line to the line $O_L P_R$ from the left pupil $P_L$ is the right pupil $P_R$ as shown in FIG. 22. The line $\overrightarrow{P_L P_R}$ is the shortest when dropping the perpendicular line.

In this case, it is assumed that the inter-pupil distance $|\overrightarrow{P_L P_R}|$ is obtained, and the right pupil $P_R$ is detected when the obtained inter-pupil distance $|\overrightarrow{P_L P_R}|$ is shorter than $l_{max}$. Then, G and m are obtained, and the left pupil $P_L$ and the right pupil $P_R$ are calculated again using Equations (52) and (53) or Equations (54) and (55) and used for the next frame. Note that, when $|\overrightarrow{P_L P_R}| < l_{min}$ or $|\overrightarrow{P_L P_R}| > l_{max}$, the right pupil $P_R$ is determined not to exist due to closing the eye or the like.

Finally, in any of the above cases, the three-dimensional position of the pupil which is detected by both of the two cameras is determined first, and the pupil which is detected by only one camera is detected secondarily based on the position of the pupil which is detected by both cameras. This is because the reliability of the detected three-dimensional position is considered to be lower for the one detected by only one camera.

Further, in the above-described examples, the case where both of the left pupil $P_L$ and the right pupil $P_R$ are detected by the left camera $O_L$, and only the left pupil $P_L$ is detected by the right camera $O_R$ is shown. In the case where both of the left pupil $P_L$ and the right pupil $P_R$ are detected by the right camera $O_R$, and only the right pupil $P_R$ is detected by the left camera $O_L$ also, the three-dimensional coordinates of the right pupil $P_R$ are obtained first and then the three-dimensional coordinates of the left pupil $P_L$ are obtained after that in the same manner.

Next, the case where different pupils are detected by different cameras is described. Specifically, the case where the left pupil is detected by the left camera and the right pupil is detected by the right camera as shown in FIG. 23(a) and the case where the right pupil is detected by the left camera and the left pupil is detected by the right camera as shown in FIG. 23(b) are described hereinbelow.

Figure 23:
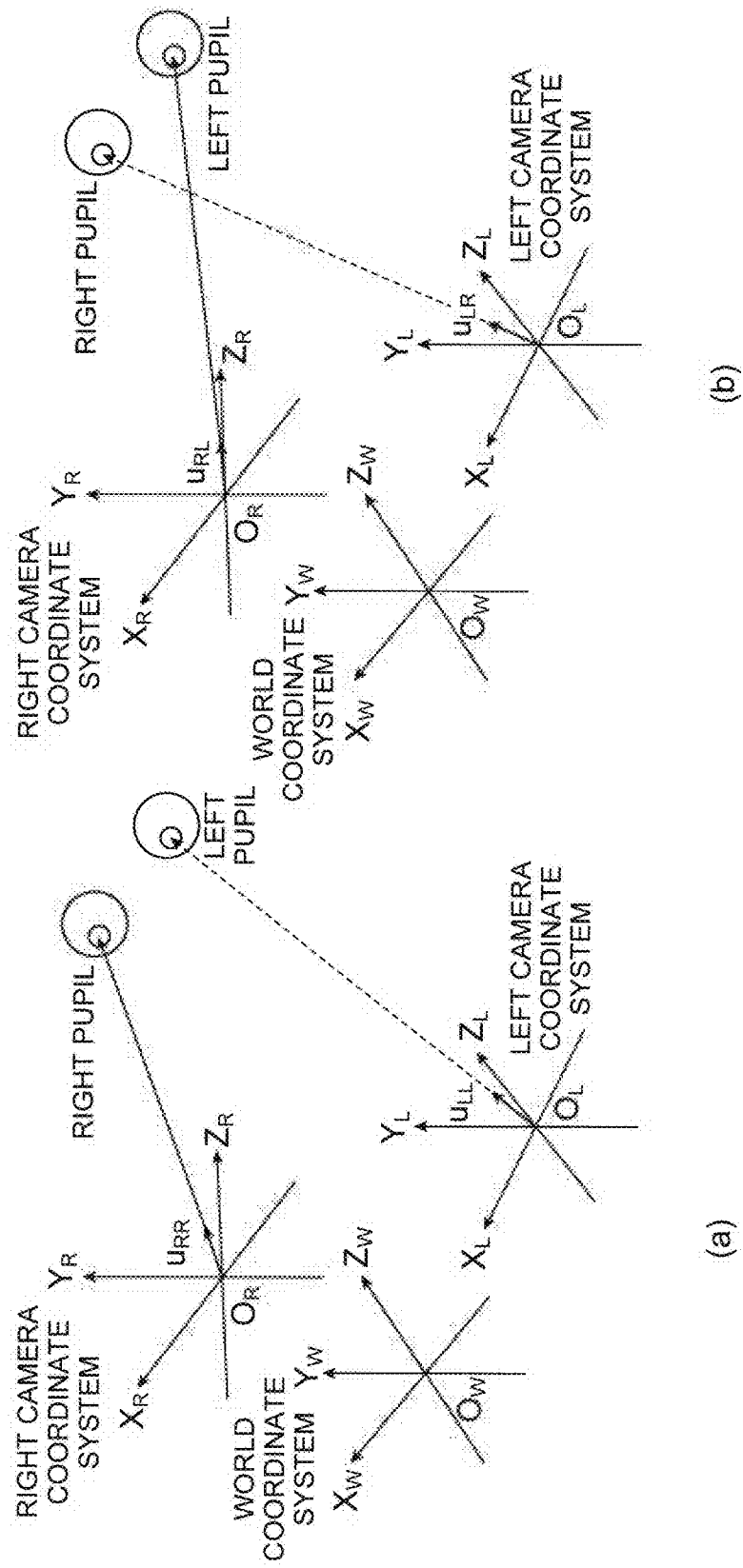
FIG. 23 is a view showing a pupil tracking method when only one pupil is detected by one camera, and only the other pupil is detected by the other camera.
Figure 24:
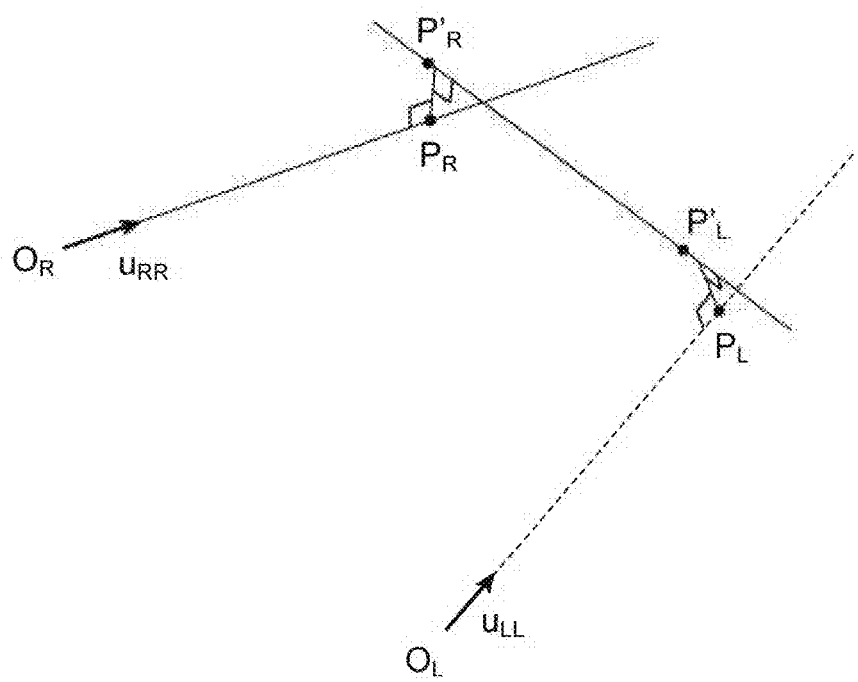
FIG. 24 is a view showing a pupil tracking method when only one pupil is detected by one camera, and only the other pupil is detected by the other camera.

The case shown in FIG. 23(a) is described first. In this case, as shown in FIG. 24, the left pupil exists on the line (third line) that passes $O_L$ and has the unit direction vector $u_{LL}$, derived from the two-dimensional pupil position detected from the left camera image, and the right pupil exists on the line (fourth line) that passes $O_R$ and has the unit direction vector $u_{RR}$, from the right camera image. However, both of the pupils are not detected by both of the two cameras, and therefore the three-dimensional positions of them cannot be estimated by stereo matching Thus, for the left pupil $P_L$, a common perpendicular line of the line $P'_L P'_R$ (fifth line) connecting the left pupil $P'_L$ and the right pupil $P'_R$ in the current frame predicted by Equations (52) and (53) or Equations (54) and (55) and the line that passes $O_L$ and has the unit direction vector $u_{LL}$ is obtained. Then, the intersection point between the obtained common perpendicular line and the line that passes $O_L$ and has the unit direction vector $u_{LL}$ is obtained, and the intersection point is obtained as the three-dimensional coordinate of the left pupil $P_L$. The obtained intersection point is a proximity point that is in close proximity to both of the third line and the fifth line. Further, for the right pupil $P_R$, a common perpendicular line of the line $P'_L P'_R$ connecting the left pupil $P'_L$ and the right pupil $P'_R$ in the current frame predicted by the same method as above and the line that passes $O_R$ and has the unit direction vector $u_{RR}$ is obtained. Then, the intersection point between the obtained common perpendicular line and the line that passes $O_R$ and has the unit direction vector $u_{RR}$ is obtained, and the intersection point is obtained as the three-dimensional coordinate of the right pupil $P_R$. The obtained intersection point is a proximity point that is in close proximity to both of the fourth line and the fifth line. Based on the three-dimensional coordinates of the left pupil and the right pupil obtained in this way, after obtaining G and m, the left pupil $P_L$ and the right pupil $P_R$ are calculated using Equations (52) and (53) or Equations (54) and (55) and used for the next frame. Note that the state where each pupil is detected only by one different camera is generally unstable, and if such a state continues, it becomes impossible to correctly estimate the three-dimensional coordinates of the pupils. In such conditions, if this method is performed continuously for a certain period of time, such as for one second, for example, the subtraction position correction becomes inaccurate or becomes totally unavailable. Thus, when such a state continues for a certain period of time, it is necessary to stop the processing and perform image subtraction in the whole image or in the range where the pupil is likely to exist without applying a small window to the pupil.

This is the same for the case where the right pupil is detected by the left camera and the left pupil is detected by the right camera shown in FIG. 23(b).

Figure 25:
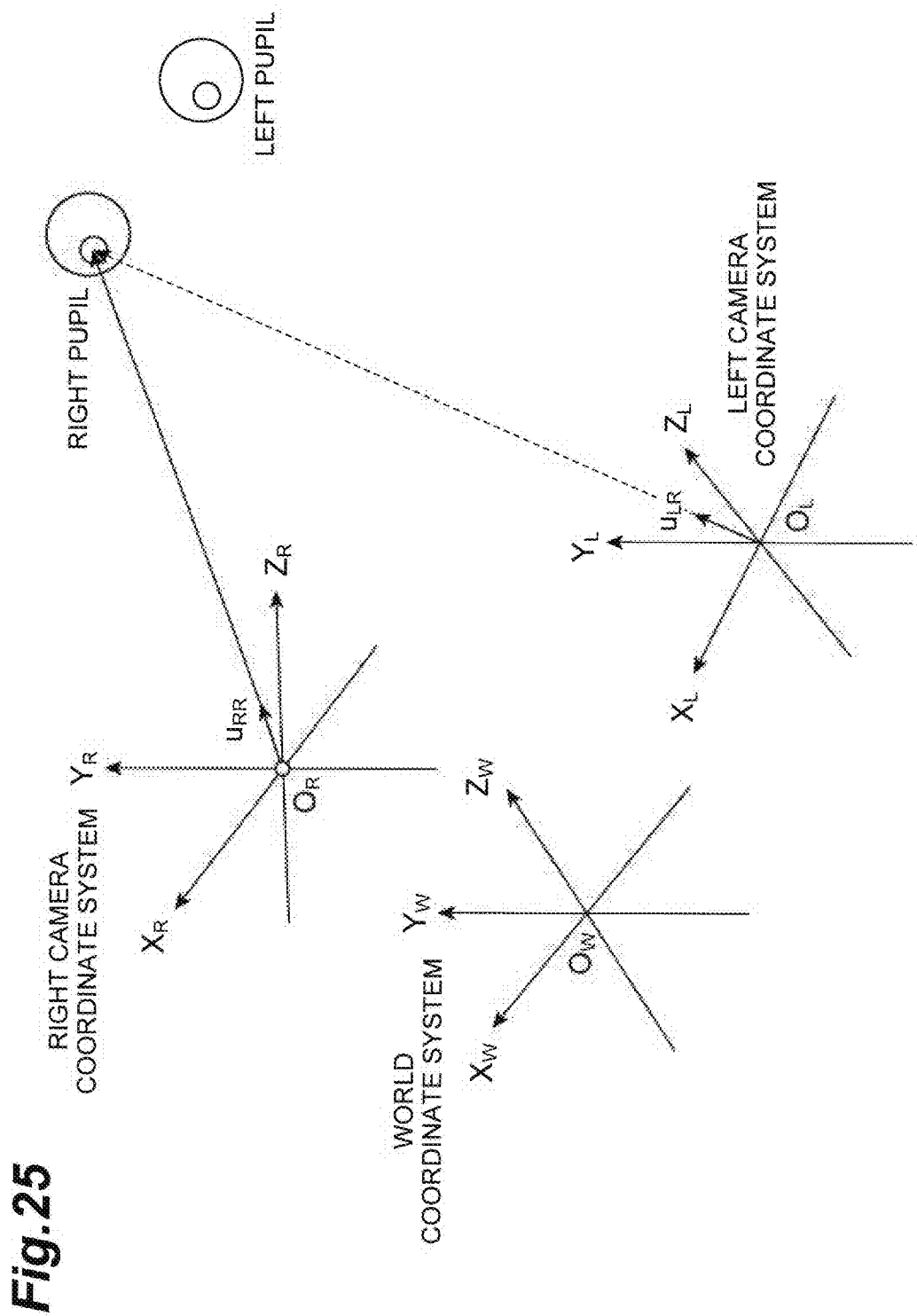
FIG. 25 is a view showing a pupil tracking method when only one pupil is detected by two cameras.

Next, the case where only one pupil is detected by two or more cameras as shown in FIG. 25 is described. It is assumed that the right pupil is detected by two cameras, and the left pupil is not detected by any of the cameras. Such a case occurs when performing an input operation by a wink as an alternative to a mouse click in the field of application such as a pupil mouse, for example.

In the case where one pupil is not detected by any of the cameras, the state is likely to be significantly unstable with the method of using the continuity of G and m, which is often described above. A method of performing the tracking process only for several frames and then removing the window can be employed as a matter of course. However, in such a case, a subject generally closes one eye with the head at rest in order to stop a cursor at a certain position on the screen. Thus, it is considered that the pupil does not move at this time.

Therefore, it is preferred to determine $P'_L$ and $P'_R$ by setting m'=m and l'=l and assuming $P'_R$ to be equal to the position $P_R$ of the right pupil obtained by stereo matching in Equations (52) and (53) or Equations (54) and (55). Note that the subsequent process is the same. l in this case indicates the inter-pupil distance that is obtained in the previous frame.

(Experimental Result of Pupil Tracking Method)

An experimental result of the pupil tracking method according to this embodiment described above is described hereinafter.

This experiment was conducted using a device similar to the pupil detection device 10 shown in FIG. 1. To be more specific, this device is composed of two sets of optical systems having a camera (stereo) structure, a light emitting circuit, a personal computer or the like. Each of the optical systems is composed of a noninterlaced digital camera, a 16 mm lens, a visual light cut filter, and a double ring-shaped near infrared LED. An acquired image of the camera is a 60 fps gray scale image, and the size of one frame is 640×480 pixels.

Using this device, a light pupil image and a dark pupil image were acquired by making the inner LED and the outer LED of the ring-shaped LED light source alternately blink by a flash signal of the camera, and a difference image is obtained from those images. At this time, synchronization between two cameras is shifted by 650 microseconds so that light emitted from one light source does not interfere with another camera.

The experiment was conducted in the situation where four persons wearing glasses sat at the position of about 80 cm from a camera, and light was applied to the faces of the subjects by an electric bulb. The electric bulb was used for reducing the pupils of the subjects who feel glare of the electric bulb and thereby making it difficult to distinguish between the pupil and the glasses reflection, rather than for producing the glasses reflection by the electric bulb. The illuminance around the pupils was 262 to 345 lx. The subjects were instructed to turn the head left and right so as to generate the time period when the pupil and the glasses reflection in the camera image overlap, and 300 frames of images were taken for each subject. In analysis, the obtained images were checked for each frame.

Figure 26:
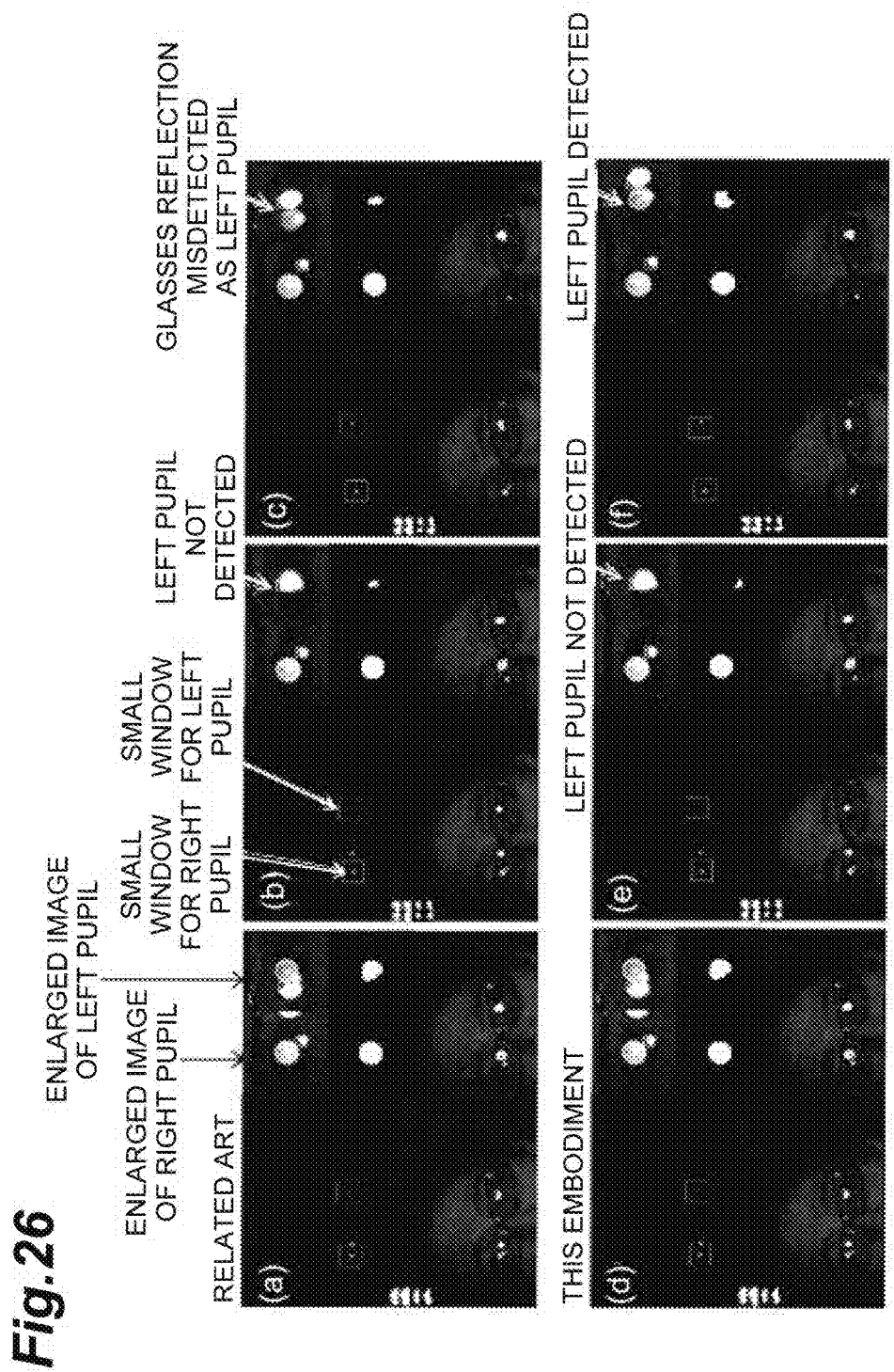
FIG. 26 is a view showing comparison between a pupil tracking result by a pupil tracking method according to related art and a pupil tracking result by a pupil tracking method according to this embodiment.

FIG. 26 shows processing images in the right camera according to related art and this embodiment in the case of turning the head left and right. FIGS. 26(a) to 26(c) are processing images according to related art. FIGS. 26(d) to 26(f) are processing images according to this embodiment. In the related art, as the face of the subject moves from the state shown in (a) to the state shown in (c), when the pupil and the glasses reflection overlap as shown in (b), the tracking of the glasses reflection, not the pupils, is started at the timing shown in (c). In the related art, the left and right pupils are tracked for each of the left and right cameras, and the method performs pupil detection by performing subtraction position correction of the corneal reflection. On the other hand, in the pupil tracking method according to this embodiment, even when the face moves from the state shown in (d) to the state shown in (f) and the pupil and the glasses reflection overlap as shown in (e), the pupils are kept tracked at the timing shown in (f).

Figure 27:
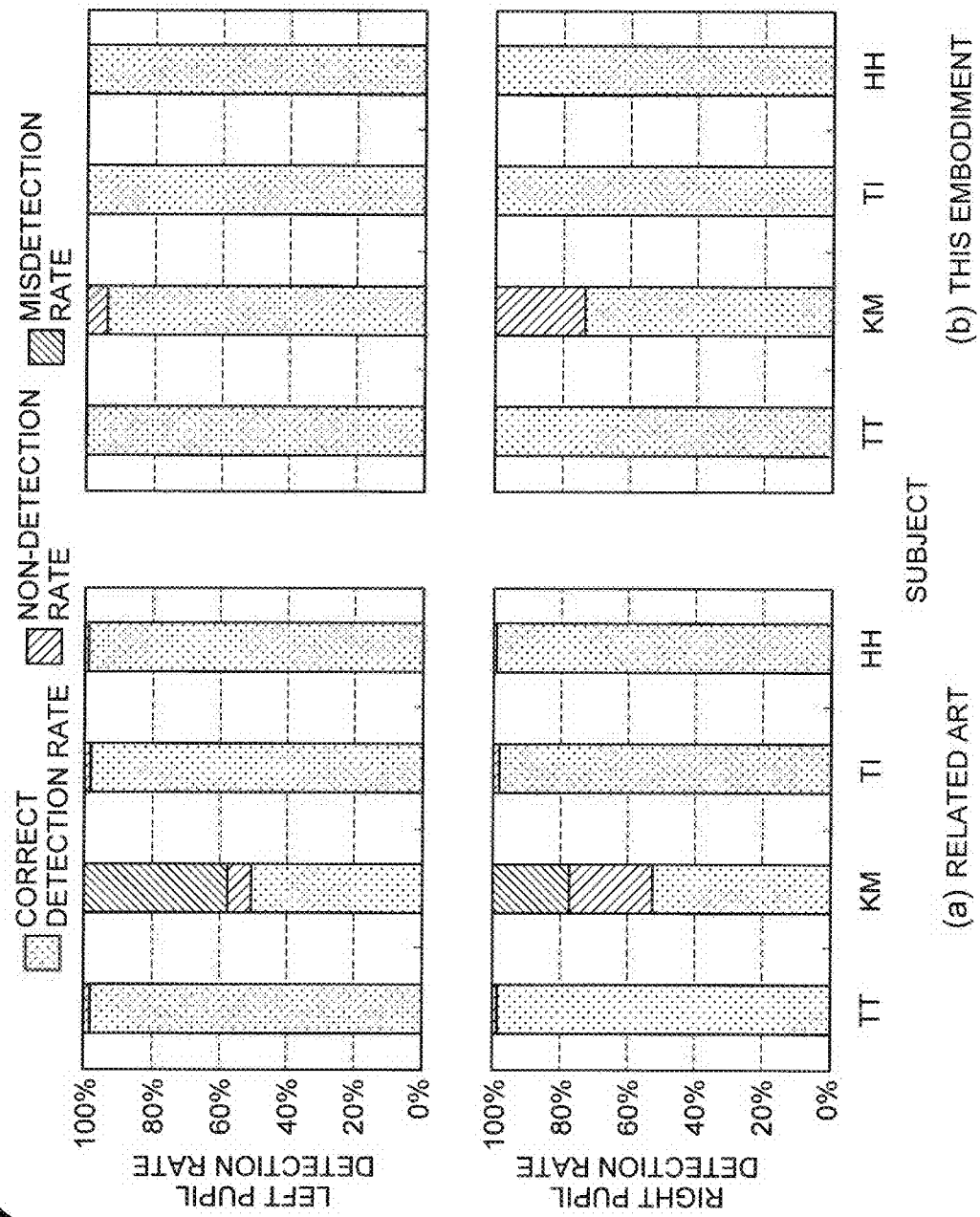
FIG. 27 is a graph showing comparison between a pupil tracking result by a pupil tracking method according to related art and a pupil tracking result by a pupil tracking method according to this embodiment.

FIG. 27 shows the detection rate of the left and right pupils by the right camera. The correct detection rate indicates the cases where pupils can be detected correctly, the non-detection rate indicates the cases where nothing is detected, and the misdetection rate indicates misdetection of those other than pupils as pupils.

For three of the four subjects, because the correct detection rate was high in the related art as well, a difference in the pupil tracking method according to this embodiment was only that the correct detection rate becomes closer to 100%. On the other hand, for the remaining one subject KM, while the misdetection rate was very high in the related art, the misdetection rate decreased to 0 in the pupil tracking method according to this embodiment as shown in the graph on the right of FIG. 27. In the pupil tracking method according to this embodiment also, the non-detection rate was high. However, in the frame where it resulted in non-detection, the glasses reflection overlapped with the pupil and appeared in the camera, and therefore non-detection in this frame was appropriate. This is understandable from the fact that the non-detection rate in the related art and the non-detection in the proposed method are substantially the same. The same result was obtained also for the left camera.

(Facial Posture Detection Method)

A facial posture detection method according to this embodiment is described hereinafter. The facial posture detection method is a method of detecting the facial posture of a subject based on the three-dimensional coordinates of a pair of pupils of a subject that have been detected by the above-described pupil detection method.

By the following method, the left and right rotation of the subject's head and the rotation around the anteroposterior axis can be detected. It is assumed that there are two pupils, the left pupil $P_L$ and the right pupil $P_R$, of one subject in the world coordinate system as shown in FIG. 28(a). The $Y_w$ axis of the world coordinate system is the vertical axis, and the positive direction of the $Y_w$ axis is upward in the vertical direction. Thus, the positive direction of the $Y_w$ axis is upward in the normal head posture of the subject. Further, the $Z_w$ axis is the anteroposterior axis, which is the axis penetrating the subject's head front to rear, and the positive direction is the direction facing backward of the subject's head. FIG. 28(b) shows a method of roughly calculating the inclination of the head rotation about the anteroposterior axis of the subject's head. The dotted line in this figure is the straight line that is parallel to the $X_w$-$Z_w$ plane. The angle $\gamma$ in this figure indicates the inclination of the inter-pupil unit direction vector m from the horizontal plane. The angle $\gamma$ can be represented by the following Equation (65) using the component of the vector m.

[Math65]
$$\gamma = \tan^{-1}\left(\frac{m_y}{\sqrt{m_x^2 + m_z^2}}\right) \tag{65}$$

Further, the angle $\alpha$ of the face in the horizontal direction when viewing the two pupils from above the head can be as shown in FIG. 28(c). The arrow F in the figure indicates the direction normal to the face. The angle $\alpha$ can be represented by the following Equation (66) using the component of the vector m.

[Math66]
$$\alpha = \tan^{-1}\left(\frac{m_z}{m_x}\right) \tag{66}$$

Further, the rotation angle $\delta$ around the anteroposterior axis of the face as the angle viewed from the front (the negative direction of the $Z_w$ axis) in the normal head posture of the subject can be as shown in FIG. 28(d). The angle $\delta$ can be calculated by the following Equation (67).

[Math67]
$$\delta = \tan^{-}\left(\frac{m_y}{m_x}\right) \tag{67}$$

Note that, by defining the center of gravity G of both pupils as the position of the face, the facial posture excluding rotation in the vertical direction can be detected in all cases.

Note that, because this method detects a facial posture using pupil positions only and does not detect nostrils, it is not possible to detect the direction of the face correctly. However, when the camera is placed far below the front of the subject's face, there are many cases where the nostrils appear in the image. Thus, it is feasible to detect the nostrils by image processing and detect the facial direction using the positions of the nostrils by the method disclosed in Patent Literatures 3, 4 and 9. Different facial posture detection methods may be used for the case where the nostrils are detected and the case where the nostrils are not detected.

Although the case of performing subtraction position correction is mainly described in this specification, the need for subtraction position correction is eliminated by dividing the wavelength of reflected light emitted from a dual-wavelength light source and reflected on the face and synchronizing the timing to acquire a light pupil image and a dark pupil image. In such a case, while subtraction position correction is not needed, because the three-dimensional coordinates of the pupils in the current frame are predicted from information obtained from the previous frame and the obtained coordinates are converted into the coordinates on the image in the current frame of each camera before performing subtraction by subtraction position correction, it is possible to apply a small window centering on the coordinates in the same method as the method of the present invention. By applying the small window, the effect of reducing the possibility of misdetection of glasses reflection or the like is obtained. The same applies to the case where a light pupil image and a dark pupil image are obtained for each very short period of time (for example, 0.5 microseconds).

The advantage of the tracking is that it is difficult to distinguish between the left and right pupils by the pupil detection. In a pupil mouse, a right wink and a left wink of a subject correspond to a right click and a left click by a general mouse that is operated by the hand. In this case, at the time when both pupils are detected, the right pupil and the left pupil are specified, and even when one pupil becomes non-detected, whether the pupil that is kept detected is the right pupil or the left pupil is specified from the continuity accompanying the tracking. In the case where the tracking is not performed and the pupil is detected from the whole image for each frame, association between frames is not made, and therefore it is not distinguishable whether the detected pupil is the right pupil or the left pupil in the frame in which one pupils is not detected.

Further, in automobile use, the pupils are small, and the pupils appear dark in the difference image and difficult to be detected even if glasses reflection does not occur. In such a case, when one pupil ceases to be detected due to some reason, because the detected pupil is identified as the right pupil or the left pupil, a relatively large window is applied near the non-detected eye so that search is made only within the window. In this case also, it is important that the detected pupil is identified as right or left.

(Inter-Pupil Distance)

In some of the above-described embodiments, the step of calculating the inter-pupil distance is included. The inter-pupil distance is a value that needs to be accurate in order to determine a pupil pair of a subject. Particularly, when a glasses reflection image of a subject is in close proximity to a pupil image, it is necessary to accurately calculate the inter-pupil distance in order to distinguish between the glasses reflection image and the pupil image.

In the case where camera calibration (stereo calibration) is not correctly done particularly when using two cameras, the inter-pupil distance obtained by calculation is likely to have a large difference from the actual inter-pupil distance according to the distance between the camera and the subject. Thus, even if, when the subject's head is at a specific position, the inter-pupil distance is obtained by correctly stereo-matching the two pupils of the subject and calculating the three-dimensional coordinates of the pupils, the calculated inter-pupil distance changes when the subject's head moves. Therefore, it is difficult to distinguish between the glasses reflection image and the pupil image of the subject. Further, an error can always occur in camera calibration. Therefore, it is effective to detect a correct pupil pair even when there is an error in camera calibration.

Further, the inter-pupil distance varies depending on the angle of convergence of both eyes of a subject. Accordingly, the inter-pupil distance is not always a constant value. As one example, assume the case where a subject is looking at a display, and a camera is mounted on the display. In this case, when the subject's face is close to the display, both eyes of the subject come inward, and the inter-pupil distance becomes shorter. On the other hand, when the subject's face is away from the display, the axis of sighting of both eyes of the subject becomes more parallel, and the inter-pupil distance becomes longer.

It is therefore preferred to correctly calculate the inter-pupil distance according to the distance between the camera and the subject's head. However, when the subject is wearing glasses, the glasses reflection image of the subject is misdetected as the pupil image in some cases, which makes it difficult to correctly calculate the inter-pupil distance. Thus, a method that can obtain the correct inter-pupil distance even when a pupil pair is misdetected is described hereinafter.

This method continuously calculates the inter-pupil distance based on the latest image taken at all times, creates a frequency distribution (histogram) of the obtained inter-pupil distances, updates the frequency distribution as needed and determines the value of the inter-pupil distance corresponding to the peak of the frequency distribution (which is the mode of the inter-pupil distance) as the final value of the inter-pupil distance. The inter-pupil distance that is calculated based on the latest image may be incorrect. The resolution of the inter-pupil distance (which is the width of each section of the frequency distribution) is 0.1 mm, for example. The total of the frequencies of the frequency distribution is 50, for example. Specifically, the values of the inter-pupil distance based on each of the latest 50 frame images are calculated on a steady basis, and a histogram is created by the calculated 50 values of the inter-pupil distance. In this case, when there is a frame for which the inter-pupil distance cannot be calculated due to some reason (for example, including the case where the pupil image cannot be detected due to blinking of the subject) among the latest 50 frames, it is preferred to create a histogram based only on the inter-pupil distance calculated in the frames for which the inter-pupil distance can be calculated out of the period corresponding to the time of the latest 50 frames, and determine the inter-pupil distance indicating the peak of the frequency in this histogram as the final inter-pupil distance. It is feasible to calculate the inter-pupil distance based on 50 frames for which the values of the inter-pupil distance have been able to be calculated by going back from the period corresponding to the time of the latest 50 frames, and create a histogram based on the calculated values of the inter-pupil distance. However, under the condition that the subject's head moves, the values of the inter-pupil distance calculated in the frames at old times are less reliable. Therefore, it is more preferred to create a histogram of the inter-pupil distance by using the images during the time of the latest 50 frames.

The advantage of the method of determining the inter-pupil distance using a histogram is that, even when an incorrect inter-pupil distance is calculated based on the image at a certain time, by creating a histogram and employing the mode, it is less affected by the value of the incorrect inter-pupil distance. Note that, instead of the mode, the frequencies of the histogram may be sequentially added from either of the minimum value and the maximum value of the inter-pupil distance, and a value where a result of the addition is a value that is 50% the total frequencies (which is the median of the inter-pupil distance) may be selected as the final inter-pupil distance.

In the above-described embodiment, the fifth step may include a tenth step of calculating three-dimensional coordinates by stereo matching from a combination of one of the first image candidate points and one of the second image candidate points based on the first image and the second image, and an eleventh step of excluding the combination as not corresponding to the same point in three-dimensional coordinates when the calculated three-dimensional coordinate value is not within a specified range.

Further, the fifth step may include a twelfth step of determining a first line connecting the first image candidate point and the first camera based on coordinates of the first image candidate point in the first image; a thirteenth step of determining a second line connecting the second image candidate point and the second camera based on coordinates of the second image candidate point in the second image, a fourteenth step of determining a common perpendicular line of the first line and the second line, and a fifteenth step of excluding the combination as not corresponding to the same point in three-dimensional coordinates when a length of the common perpendicular line is shorter than a specified threshold and a three-dimensional coordinate value of a midpoint of the common perpendicular line is not within a specified range.

Further, a pupil detection method according to the present invention may include a sixteenth step of taking a facial image of a subject using at least three cameras, a seventeenth step of selecting at least two pairs of the first camera and the second camera from the at least three cameras, and an eighteenth step of detecting pupils of the subject by the above described pupil detection method by using each of the selected pairs of the first camera and the second camera.

Further, pupil pairs of a plurality of persons may be detected by the above-described pupil detection method.

Further, a pupil detection method according to the present invention may include a step of determining at least three camera pairs being a combination of two cameras among at least three cameras, a step of determining a pair of pupils of a subject as a pupil pair candidate by the above-described pupil detection method for each of the determined at least three camera pairs where one camera of the camera pair is a first camera and another camera of the camera pair is a second camera, a step of obtaining a direction vector connecting one pupil and another pupil in the pupil pair candidate for each of pupil pair candidates determined by the at least three camera pairs, a step of deleting a pupil pair candidate determined by one camera pair when a direction of the direction vector obtained for the pupil pair candidate determined by the one camera pair forms an angle of a specified threshold or more with a direction of direction vectors obtained for pupil pair candidates determined by a plurality of other camera pairs, and a step of calculating an average value of coordinates for pupil pair candidates of the subject remaining without being deleted in the deleting step and determining the average value as a final position of the pupil.

Further, a pupil tracking method according to the above-described embodiment may include a thirty-third step of detecting one pupil pair by any of the above-described pupil detection methods, a thirty-fourth step of detecting a first pupil of a subject by both of the first camera and the second camera and detecting a second pupil of the subject by one of the first camera and the second camera at a certain time after the thirty-third step is performed, a thirty-fifth step of calculating three-dimensional coordinates of the first pupil based on image coordinates of the first pupil in each of the first camera and the second camera, a thirty-sixth step of calculating a line passing the one camera and the second pupil based on image coordinates of the second pupil acquired by the one camera, and a thirty-seventh step of determining a point existing on the calculated line and where a distance from the first pupil in a three-dimensional space is a specified value given based on an inter-pupil distance as the second pupil of the subject.

Further, the above-described pupil tracking method may include a thirty-eighth step of detecting one pupil pair of a subject by any of the above-described pupil detection methods, a thirty-ninth step of acquiring images by taking a facial image of the subject using each of the first camera and the second camera, a fortieth step of detecting one pupil pair of the subject at a first time after the thirty-eighth step is performed and at a second time later than the first time, a forty-first step of calculating absolute positions and relative positions of the one pupil pair detected at the first time and the second time, a forty-second step of estimating absolute positions and relative positions of the one pupil pair at a third time later than the second time based on the calculated absolute positions and relative positions of the one pupil pair at the first time and the second time, a forty-third step of estimating three-dimensional coordinates of each pupil of the one pupil pair at the third time based on the estimated absolute positions and relative positions of the one pupil pair at the third time, a forty-fourth step of detecting the first pupil of the subject by one of the first camera and the second camera and detecting the second pupil of the subject by another camera different from the one camera at the third time, a forty-fifth step of calculating a third line passing the one camera and the first pupil based on image coordinates of the first pupil detected by the one camera at the third time, a forty-sixth step of calculating a fourth line passing the other camera and the second pupil based on image coordinates of the second pupil detected by the other camera at the second time; a forty-seventh step of calculating a fifth line connecting the first pupil and the second pupil at the first time, a forty-eighth step of determining a proximity point in close proximity to both of the third line and the fifth line as the first pupil at the second time, and a forty-ninth step of determining a proximity point in close proximity to both of the fourth line and the fifth line as the second pupil at the second time.

Further, the above-described pupil tracking method may include a fiftieth step of detecting one pupil pair by any of the above-described pupil detection methods, a fifty-first step of acquiring images by taking a facial image of a subject using each of the first camera and the second camera, a fifty-second step of acquiring three-dimensional coordinates of each of one pupil pair of the subject at a first time after the fiftieth step is performed, a fifty-third step of calculating relative positions of the one pupil pair at the first time, a fifty-fourth step of calculating three-dimensional coordinates of the other pupil different from the one pupil at a second time later than the first time based on image coordinates of the other pupil in each of the first camera and the second camera at the second time when one of the first pupil and the second pupil of the subject cannot be detected by any of the first camera and the second camera, and a fifty-fifth step of calculating three-dimensional coordinates of the one pupil at the second time based on the relative positions of the one pupil pair at the first time calculated in the fifty-third step and the three-dimensional coordinates of the other pupil at the second time calculated in the fifty-fourth step.

Further, the above-described pupil tracking method may include a fifty-sixth step of detecting one pupil pair by any of the above-described pupil detection methods, a fifty-seventh step of acquiring images by taking a facial image of a subject using each of the first camera and the second camera at a certain time after the fifty-sixth step is performed, a fifty-eighth step of extracting an image corneal reflection candidate point serving as a candidate for corneal reflection of the subject from the images acquired in the fifty-seventh step, a fifty-ninth step of calculating three-dimensional coordinates of left and right corneal sphere centers of the subject based on the image corneal reflection candidate point acquired in the fifty-eighth step, a sixtieth step of setting a small region in each of the images taken by the first camera and the second camera based on positions of the three-dimensional coordinates of the left and right corneal sphere centers of the subject calculated in the fifty-ninth step, and a sixty-first step of determining a position of a pupil by specified image processing in the small region set in the sixtieth step and calculating image coordinates of the pupil.

INDUSTRIAL APPLICABILITY

The present invention is applied to a pupil detection method, a corneal reflection detection method, a facial posture detection method and a pupil tracking method, and it is possible to improve robustness and accuracy without imposing restrictions on the rotation of a user's head and the positions of cameras.

REFERENCE SIGNS LIST

1 . . . image processing device, 2A . . . left camera, 2B . . . right camera, 3,3a,3b,3c,3d . . . light source, 10 . . . pupil detection device

The invention claimed is:

1. A pupil detection method comprising:
a first step of acquiring a first image by taking a facial image of a subject using a first camera;
a second step of acquiring a second image by taking a facial image of the subject using a second camera;
a third step of extracting one or more first image candidate points serving as candidates for a pupil of the subject from the first image;
a fourth step of extracting one or more second image candidate points serving as candidates for a pupil of the subject from the second image;
a fifth step of determining whether a combination of one of the first image candidate points and one of the second image candidate points corresponds to the same point in a three-dimensional space;
a sixth step of extracting two or more space candidate points by setting the point in the three-dimensional space corresponding to the combination of the first image candidate point and the second image candidate point determined as corresponding to the same point in three-dimensional coordinates as the space candidate point;
a seventh step of selecting a pair of two space candidate points among the extracted space candidate points and calculating a distance between the selected pair of two space candidate points for a plurality of pairs of space candidate points;
an eighth step of excluding a pair of space candidate points where the calculated distance between the pair of space candidate points is not within a specified range; and
a ninth step of determining one or more pairs of space candidate points among the pairs of space candidate points having not been excluded and determining that a pair of pupils of the subject exist at positions of the determined one or more pairs of space candidate points.

2. The pupil detection method according to claim 1, wherein the fifth step comprises:
a tenth step of calculating three-dimensional coordinates by stereo matching from a combination of one of the first image candidate points and one of the second image candidate points based on the first image and the second image; and
an eleventh step of excluding the combination as not corresponding to the same point in three-dimensional coordinates when the calculated three-dimensional coordinate value is not within a specified range.

3. The pupil detection method according to claim 1, wherein the fifth step comprises:
a twelfth step of determining a first line connecting the first image candidate point and the first camera based on coordinates of the first image candidate point in the first image;
a thirteenth step of determining a second line connecting the second image candidate point and the second camera based on coordinates of the second image candidate point in the second image;
a fourteenth step of determining a common perpendicular line of the first line and the second line; and
a fifteenth step of excluding the combination as not corresponding to the same point in three-dimensional coordinates when a length of the common perpendicular line is shorter than a specified threshold and a three-dimensional coordinate value of a midpoint of the common perpendicular line is not within a specified range.

4. A pupil detection method according to claim 1, further comprising:
a sixteenth step of taking a facial image of a subject using at least three cameras;
a seventeenth step of selecting at least two pairs of the first camera and the second camera from the at least three cameras; and
an eighteenth step of detecting pupils of the subject by the pupil detection method by using each of the selected pairs of the first camera and the second camera.

5. A pupil detection method according to claim 1, further comprising
a step of detecting pupil pairs of a plurality of persons by the pupil detection method.

6. A pupil detection method according to claim 1, further comprising:
a step of determining at least three camera pairs being a combination of two cameras among at least three cameras;
a step of determining a pair of pupils of a subject as a pupil pair candidate by the pupil detection method for each of the determined at least three camera pairs where one camera of the camera pair is a first camera and another camera of the camera pair is a second camera;
a step of obtaining a direction vector connecting one pupil and another pupil in the pupil pair candidate for each of pupil pair candidates determined by the at least three camera pairs;
a step of deleting a pupil pair candidate determined by one camera pair when a direction of the direction vector obtained for the pupil pair candidate determined by the one camera pair forms an angle of a specified threshold or more with a direction of direction vectors obtained for pupil pair candidates determined by a plurality of other camera pairs; and
a step of calculating an average value of coordinates for pupil pair candidates of the subject remaining without being deleted in the deleting step and determining the average value as a final position of the pupil.

7. A corneal reflection detection method comprising:
a nineteenth step of detecting pupils of a subject by the pupil detection method according to claims 1;
a twentieth step of extracting one or more first image corneal reflection candidate points serving as candidates for corneal reflection of the subject from the first image;
a twenty-first step of extracting one or more second image corneal reflection candidate points serving as candidates for corneal reflection of the subject from the second image;
a twenty-second step of selecting one from each of the extracted first image corneal reflection candidate points and second image corneal reflection candidate points;
a twenty-third step of calculating three-dimensional coordinates corresponding to a combination of the selected first image corneal reflection candidate point and second image corneal reflection candidate point based on image coordinates of the selected first image corneal reflection candidate point in the first image and image coordinates of the selected second image corneal reflection candidate point in the second image; and
a twenty-fourth step of determining the calculated three-dimensional coordinates as corneal reflection of the subject when positions of the calculated three-dimensional coordinates and the detected three-dimensional coordinates of the pupil are within a specified range.

8. A facial posture detection method for detecting a facial posture of a subject based on three-dimensional coordinates of one pair of pupils of a subject detected by the pupil detection method according to claims 1.

9. A pupil detection method according to claim 1, further comprising:
a twenty-fifth step of detecting one pupil pair of a subject by the pupil detection method;
a twenty-sixth step of acquiring images by taking a facial image of a subject using each of the first camera and the second camera;
a twenty-seventh step of detecting one pupil pair of the subject at a first time after the step of detecting one pupil pair is performed and at a second time later than the first time;
a twenty-eighth step of calculating absolute positions and relative positions of the one pupil pair detected at the first time and the second time;
a twenty-ninth step of estimating absolute positions and relative positions of the one pupil pair at a third time later than the second time based on the calculated absolute positions and relative positions of the one pupil pair at the first time and the second time;
a thirties step of estimating image coordinates of each pupil of the one pupil pair at the third time based on the estimated absolute positions and relative positions of the one pupil pair at the third time;
a thirty-first step of setting a small region around the estimated image coordinates of the pupil in each of the images taken by the first camera and the second camera at the third time; and
a thirty-second step of determining a position of a pupil by specified image processing in the set small region and calculating image coordinates of the pupil at the third time in each of the images taken by the first camera and the second camera at the third time.

10. A pupil detection method according to claim 1, further comprising:
a thirty-third step of detecting one pupil pair by the pupil detection method;
a thirty-fourth step of detecting a first pupil of a subject by both of the first camera and the second camera and detecting a second pupil of the subject by one of the first camera and the second camera at a certain time after the thirty-third step is performed;
a thirty-fifth step of calculating three-dimensional coordinates of the first pupil based on image coordinates of the first pupil in each of the first camera and the second camera;
a thirty-sixth step of calculating a line passing the one camera and the second pupil based on image coordinates of the second pupil acquired by the one camera; and
a thirty-seventh step of determining a point existing on the calculated line and where a distance from the first pupil in a three-dimensional space is a specified value given based on an inter-pupil distance as the second pupil of the subject.

11. A pupil detection tracking method according to claim 1, further comprising:
a thirty-eighth step of detecting one pupil pair of a subject by the pupil detection method;
a thirty-ninth step of acquiring images by taking a facial image of the subject using each of the first camera and the second camera;
a fortieth step of detecting one pupil pair of the subject at a first time after the thirty-eighth step is performed and at a second time later than the first time;
a forty-first step of calculating absolute positions and relative positions of the one pupil pair detected at the first time and the second time;
a forty-second step of estimating absolute positions and relative positions of the one pupil pair at a third time later than the second time based on the calculated absolute positions and relative positions of the one pupil pair at the first time and the second time;
a forty-third step of estimating three-dimensional coordinates of each pupil of the one pupil pair at the third time based on the estimated absolute positions and relative positions of the one pupil pair at the third time;
a forty-fourth step of detecting the first pupil of the subject by one of the first camera and the second camera and detecting the second pupil of the subject by another camera different from the one camera at the third time;
a forty-fifth step of calculating a third line passing the one camera and the first pupil based on image coordinates of the first pupil detected by the one camera at the third time;
a forty-sixth step of calculating a fourth line passing another camera and the second pupil based on image coordinates of the second pupil detected by another camera at the second time;
a forty-seventh step of calculating a fifth line connecting the first pupil and the second pupil at the first time;
a forty-eighth step of determining a proximity point in close proximity to both of the third line and the fifth line as the first pupil at the second time; and
a forty-ninth step of determining a proximity point in close proximity to both of the fourth line and the fifth line as the second pupil at the second time.

12. A pupil detection method according to claim 1, further comprising:
a fiftieth step of detecting one pupil pair by the pupil detection method;
a fifty-first step of acquiring images by taking a facial image of a subject using each of the first camera and the second camera;
a fifty-second step of acquiring three-dimensional coordinates of each of one pupil pair of the subject at a first time after the fiftieth step is performed;
a fifty-third step of calculating relative positions of the one pupil pair at the first time;
a fifty-fourth step of calculating three-dimensional coordinates of another pupil different from the one pupil at a second time later than the first time based on image coordinates of another pupil in each of the first camera and the second camera at the second time when one of the first pupil and the second pupil of the subject cannot be detected by any of the first camera and the second camera; and
a fifty-fifth step of calculating three-dimensional coordinates of the one pupil at the second time based on the relative positions of the one pupil pair at the first time calculated in the fifty-third step and the three-dimensional coordinates of another pupil at the second time calculated in the fifty-fourth step.

13. A pupil detection method according to claim 1, further comprising:
a fifty-sixth step of detecting one pupil pair by the pupil detection method;

a fifty-seventh step of acquiring images by taking a facial image of a subject using each of the first camera and the second camera at a certain time after the fifty-sixth step is performed;

a fifty-eighth step of extracting an image corneal reflection candidate point serving as a candidate for corneal reflection of the subject from the images acquired in the fifty-seventh step;

a fifty-ninth step of calculating three-dimensional coordinates of left and right corneal sphere centers of the subject based on the image corneal reflection candidate point acquired in the fifty-eighth step;

a sixtieth step of setting a small region in each of the images taken by the first camera and the second camera based on positions of the three-dimensional coordinates of the left and right corneal sphere centers of the subject calculated in the fifty-ninth step; and a sixty-first step of determining a position of a pupil by specified image processing in the small region set in the sixtieth step and calculating image coordinates of the pupil.

* * * * *